US012691115B2

(12) United States Patent
Li

(10) Patent No.: US 12,691,115 B2
(45) Date of Patent: Jul. 28, 2026

(54) METHODS FOR TREATMENT OF OBESITY, ATHEROSCLEROSIS, AND THROMBOSIS

(71) Applicant: Marshall University Research Corporation, Huntington, WV (US)

(72) Inventor: Wei Li, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 1124 days.

(21) Appl. No.: 17/610,909

(22) PCT Filed: May 14, 2020

(86) PCT No.: PCT/US2020/032920
§ 371 (c)(1),
(2) Date: Nov. 12, 2021

(87) PCT Pub. No.: WO2020/232263
PCT Pub. Date: Nov. 19, 2020

(65) Prior Publication Data

US 2022/0226320 A1 Jul. 21, 2022

Related U.S. Application Data

(60) Provisional application No. 62/847,547, filed on May 14, 2019.

(51) Int. Cl.
*A61K 31/506* (2006.01)
*A61P 3/04* (2006.01)
*A61P 3/10* (2006.01)

(52) U.S. Cl.
CPC .............. *A61K 31/506* (2013.01); *A61P 3/04* (2018.01); *A61P 3/10* (2018.01)

(58) Field of Classification Search
CPC . A61K 31/506; A61K 3/04; A61P 3/04; A61P 3/10
See application file for complete search history.

(56) References Cited

U.S. PATENT DOCUMENTS

| | | | |
|---|---|---|---|
| 5,723,115 | A | 3/1998 | Serrero |
| 6,159,969 | A | 12/2000 | Yano et al. |
| 6,451,571 | B1 | 9/2002 | Loeb et al. |
| 7,612,107 | B2 | 11/2009 | Benbrook et al. |
| 7,652,037 | B2 | 1/2010 | Rahbar et al. |
| 8,703,769 | B2 | 4/2014 | Threadgill et al. |
| 9,808,434 | B2 | 11/2017 | Rahbar et al. |
| 9,943,537 | B2 | 4/2018 | Okabe |
| 2007/0275988 | A1 | 11/2007 | Schramm |
| 2012/0021973 | A1 | 1/2012 | Lau et al. |
| 2018/0282815 | A1 | 10/2018 | Barnell et al. |
| 2018/0338976 | A1 | 11/2018 | Yoshida |

FOREIGN PATENT DOCUMENTS

| | | | |
|---|---|---|---|
| WO | 2008/075077 | A1 | 6/2008 |
| WO | 2013/186233 | A1 | 12/2013 |
| WO | 2016/142486 | A1 | 9/2016 |
| WO | 2017/178428 | A1 | 10/2017 |
| WO | 2017/223243 | A1 | 12/2017 |

OTHER PUBLICATIONS

Pryor, Rosina, and Filipe Cabreiro. "Repurposing metformin: an old drug with new tricks in its binding pockets." Biochemical Journal 471.3 (2015): 307-322. (Year: 2015).*

Ko, Jen-Chung, et al. "Metformin Induces Cytotoxicity by Downn-Regulating Thymidine Phosphorylase and Excision Repair Cross-Complementation 1 Expression in Non-Small Cell Lung Cancer Cells." Basic & clinical pharmacology & toxicology 113.1 (2013): 56-65. (Year: 2013).*

Li, Wei, and Hong Yue. "Thymidine phosphorylase: A potential new target for treating cardiovascular disease." Trends in cardiovascular medicine 28.3 (2018): 157-171. (Year: 2018).*

Rojas, Lilian Beatriz Aguayo, and Marilia Brito Gomes. "Metformin: an old but still the best treatment for type 2 diabetes." Diabetology & metabolic syndrome 5 (2013): 1-15. (Year: 2013).*

Kishton, Rigel J., et al. "AMPK is essential to balance glycolysis and mitochondrial metabolism to control T-ALL cell stress and survival." Cell metabolism 23.4 (2016): 649-662. (Year: 2016).*

Jain, Shweta, Kamla Pathak, and Ankur Vaidya. "Molecular therapy using siRNA: Recent trends and advances of multi target inhibition of cancer growth." International journal of biological macromolecules 116 (2018): 880-892. (Year: 2018).*

Mccarthy CG, et al. Toll-like receptor 9-dependent ampkalpha activation occurs via tak1 and contributes to rhoa/rock signaling and actin polymerization in vascular smooth muscle cells. The Journal of pharmacology and experimental therapeutics. 2018;365:60-71.

Kapelouzou A, et al. Overexpression of toll-like receptors 2, 3, 4, and 8 is correlated to the vascular atherosclerotic process in the hyperlipidemic rabbit model: The effect of statin treatment. J Vasc Res. 2017;54:156-169.

(Continued)

*Primary Examiner* — James H Alstrum-Acevedo
*Assistant Examiner* — Justin Christopher Sanchez
(74) *Attorney, Agent, or Firm* — Stites & Harbison, PLLC; Terry L. Wright

(57) ABSTRACT

Methods for treating obesity, atherosclerosis, and/or thrombosis comprise reducing an expression level or activity of thymidine phosphorylase in a subject in need thereof. Reducing the expression level or activity of thymidine phosphorylase as part of a method for treatment of obesity, atherosclerosis, and/or thrombosis can comprise administering to the subject an effective amount of a thymidine phosphorylase inhibitor. The thymidine phosphorylase inhibitor administered to the subject can be tipiracil, which can be administered alone or in combination with other therapeutic agents, including tissue plasminogen activator and aspirin.

14 Claims, 42 Drawing Sheets

(56) References Cited

OTHER PUBLICATIONS

Cartwright N, et al. Elucidation of toll-like receptor and adapter protein signaling in vascular dysfunction induced by gram-positive *Staphylococcus aureus* or gram-negative *Escherichia coli*. Shock. 2007;27:40-47.
Christian F, et al. The regulation of nf-kappab subunits by phosphorylation. Cells. 2016;5.
Solinas G, et al. JNK at the crossroad of obesity, insulin resistance, and cell stress response. Mol Metab. 2017;6:174-184.
Li H, et al. Emerging role of jnk in insulin resistance. Curr Diabetes Rev. 2013;9:422-428.
Lee YH, et al. C-jun n-terminal kinase (jnk) mediates feedback inhibition of the insulin signaling cascade. The Journal of biological chemistry. 2003;278:2896-2902.
O'neill LA, et al. The history of toll-like receptors—redefining innate immunity. Nat Rev Immunol. 2013; 13:453-460.
Brown V, et al. Binding specificity of toll-like receptor cytoplasmic domains. Eur J Immunol. 2006;36:742-753.
Dallari S, et al. Src family kinases fyn and lyn are constitutively activated and mediate plasmacytoid dendritic cell responses. Nat Commun. 2017;8:14830.
Wang KZ, et al. Traf6 activation of pi 3-kinase-dependent cytoskeletal changes is cooperative with ras and is mediated by an interaction with cytoplasmic src. J Cell Sci. 2006; 119:1579-1591.
Chen K, et al. A specific cd36-dependent signaling pathway is required for platelet activation by oxidized low-density lipoprotein. Circulation research. 2008; 102:1512-1519.
Anto Michel N, et al. Inflammatory pathways regulated by tumor necrosis receptor-associated factor 1 protect from metabolic consequences in diet-induced obesity. Circulation research. 2018;122:693-700.
Fujieda S, et al. Il-10 expression is associated with the expression of platelet-derived endothelial cell growth factor and prognosis in oral and oropharyngeal carcinoma. Cancer letters. 1999;136:1-9.
Schmidt C, et al. Mechanisms of proinflammatory cytokine-induced biphasic nf-kappab activation. Mol Cell. 2003; 12:1287-1300.
White MF. The irs-signalling system: A network of docking proteins that mediate insulin action. Mol Cell Biochem. 1998;182:3-11.
Pessin JE, et al. Signaling pathways in insulin action: Molecular targets of insulin resistance. J Clin Invest. 2000;106:165-169.
Copps KD, et al. Regulation of insulin sensitivity by serine/threonine phosphorylation of insulin receptor substrate proteins irs1 and irs2. Diabetologia. 2012;55:2565-2582.
Peters GJ, et al. Thymidine phoshorylase as a target for antiangiogenesis treatment. Nucleic acids symposium series. 2008:629.
Lee TW, et al. Fyn deficiency promotes a preferential increase in subcutaneous adipose tissue mass and decreased visceral adipose tissue inflammation. Diabetes. 2013;62:1537-1546.
Kim YJ, et al. Gprc5b activates obesity-associated inflammatory signaling in adipocytes. Sci Signal. 2012;5:ra85.
Guo L, et al. Cd163+ macrophages promote angiogenesis and vascular permeability accompanied by inflammation in atherosclerosis. The Journal of clinical investigation. 2018; 128:1106-1124.
Huo Y, et al. Circulating activated platelets exacerbate atherosclerosis in mice deficient in apolipoprotein e. Nat Med. 2003;9:61-67.
Carlucci PM, et al. Neutrophil subsets and their gene signature associate with vascular inflammation and coronary atherosclerosis in lupus. JCI Insight. 2018;3.
Gimbrone MA, Jr., et al. Endothelial cell dysfunction and the pathobiology of atherosclerosis. Circulation research. 2016;118:620-636.
Bennett MR, et al. Vascular smooth muscle cells in atherosclerosis. Circulation research. 2016;118:692-702.
Cleary JM, et al. A phase 1 study of the pharmacokinetics of nucleoside analog trifluridine and thymidine phosphorylase inhibitor tipiracil (components of tas-102) vs trifluridine alone. Invest New Drugs. 2017;35:189-197.
Ali L, et al. Metabolism: The road to inflammation and atherosclerosis. Curr Opin Lipidol. 2018;29:474-480.
Tomas L, et al. Altered metabolism distinguishes high-risk from stable carotid atherosclerotic plaques. Eur Heart J. 2018;39:2301-2310.
Langer HF, et al. Leukocyte-endothelial interactions in inflammation. Journal of cellular and molecular medicine. 2009;13:1211-1220.
Chen MB, et al. Inflamed neutrophils sequestered at entrapped tumor cells via chemotactic confinement promote tumor cell extravasation. Proceedings of the National Academy of Sciences of the United States of America. 2018;115:7022-7027.
Lester EA, et al. Proinflammatory phenotype of endothelial cells after coculture with biomaterial-treated blood cells. J Biomed Mater Res A. 2003;64:397-410.
Scotland RS, et al. C-type natriuretic peptide inhibits leukocyte recruitment and platelet-leukocyte interactions via suppression of p-selectin expression. Proceedings of the National Academy of Sciences of the United States of America. 2005; 102:14452-14457.
Sehnert B, et al. Nf-kappab inhibitor targeted to activated endothelium demonstrates a critical role of endothelial nf-kappab in immune-mediated diseases. Proceedings of the National Academy of Sciences of the United States of America. 2013;110:16556-16561.
Rahaman SO, et al. Vav guanine nucleotide exchange factors regulate atherosclerotic lesion development in mice. Arteriosclerosis, thrombosis, and vascular biology. 2013;33:2053-2057.
Robinet P, et al. Consideration of sex differences in design and reporting of experimental arterial pathology studies-statement from atvb council. Arteriosclerosis, thrombosis, and vascular biology. 2018;38:292-303.
Titterington JS, et al. Growth hormone-releasing peptide-2 suppresses vascular oxidative stress in apoe-/- mice but does not reduce atherosclerosis. Endocrinology. 2009;150:5478-5487.
Laursen JB, et al. Endothelial regulation of vasomotion in apoe-deficient mice: Implications for interactions between peroxynitrite and tetrahydrobiopterin. Circulation. 2001;103:1282-1288.
Sussan TE, et al. Disruption of nrf2, a key inducer of antioxidant defenses, attenuates apoe-mediated atherosclerosis in mice. PLoS One. 2008;3:e3791.
Kuchibhotla S, et al. Absence of cd36 protects against atherosclerosis in apoe knock-out mice with no additional protection provided by absence of scavenger receptor a i/ii. Cardiovasc Res. 2008;78:185-196.
Boschetti E, et al. Liver as a source for thymidine phosphorylase replacement in mitochondrial neurogastrointestinal encephalomyopathy. PloS one. 2014;9:e96692.
Finkenstedt A, et al. Mngie syndrome: Liver cirrhosis should be ruled out prior to bone marrow transplantation. JIMD Rep. 2013;10:41-44.
Farrell GC, et al. Pathogenesis of nash: How metabolic complications of overnutrition favour lipotoxicity and pro-inflammatory fatty liver disease. Advances in experimental medicine and biology. 2018;1061:19-44.
Saponaro C, et al. The subtle balance between lipolysis and lipogenesis: A critical point in metabolic homeostasis. Nutrients. 2015;7:9453-9474.
Hotchkiss KA, et al. Thymidine phosphorylase and 2-deoxyribose stimulate human endothelial cell migration by specific activation of the integrins alpha 5 beta 1 and alpha v beta 3. The Journal of biological chemistry. 2003;278:19272-19279.
Zhou J, et al. Transfection of thymidine phosphorylase cdna to human hepatocellular carcinoma cells enhances sensitivity to fluoropyrimidine but augments endothelial cell migration. Journal of cancer research and clinical oncology. 2005;131:547-551.
Bijnsdorp IV, et al. Increased migration by stimulation of thymidine phosphorylase in endothelial cells of different origin. Nucleosides, nucleotides & nucleic acids. 2010;29:482-487.
Chen K, et al. Vav guanine nucleotide exchange factors link hyperlipidemia and a prothrombotic state. Blood. 2011.
Ghosh A, et al. Platelet cd36 mediates interactions with endothelial cell-derived microparticles and contributes to thrombosis in mice. J Clin Invest. 2008;118:1934-1943.

(56) References Cited

OTHER PUBLICATIONS

Klenotic PA, et al. Molecular basis of antiangiogenic thrombospondin-1 type 1 repeat domain interactions with cd36. Arteriosclerosis, thrombosis, and vascular biology. 2013;33:1655-1662.
United States Patent and Trademark Office, International Search Report and Written Opinion issued in corresponding Application No. PCT/US2020/032920 mailed Jul. 23, 2020.
Pryor, R et al. Repurposing metformin: an old drug with new tricks in its binding pockets. Biochem. J. 471. Oct. 16, 2015, 307-315.
Li, W et al. Thymidine phosphorylase: a potential new target for treating cardiovascular disease. Trends Cardiovasc Med. 28(3). Apr. 2018, 6-10.
Rojas, LBA et al. Metformin; an old but still the best treatment for type 2 diabetes. Diabetology & Metabolic Syndrome, 5(6), Feb. 15, 2013, p. 7.
Chiu, CJ et al. Dietary Hyperglycemia, Glycemic Index and Metabolic Retinal Diseases. Prog retin Eye Res. 30(1). Jan. 2011, 34.
Lu, DY et al. Metformin use in patients with type 2 diabetes mellitus is associated with reduced risk of deep vein thrombosis: a non-randomized, pair-matched cohort study. BMC Cardidovascular Disorders. 14(187). Dec. 15, 2014, 1-5.
Ko, JC et al. Metformin Induces Cytotoxicity by Down-Regulating Thymidine Phosphorylase and Excision Repair Cross-Complementation 1 Expression in Non-Small Cell Lung Cancer Cells. Basic & Clinical Pharmacology & Toxicology. 113. Jan. 2, 2013, 57.
Weber C, et al. Atherosclerosis: Current pathogenesis and therapeutic options. Nat Med. 2011;17:1410-1422.
Boyle JJ, et al. Expression of angiogenic factor thymidine phosphorylase and angiogenesis in human atherosclerosis. J Pathol. 2000;192:234-242.
Li W, et al. Thymidine phosphorylase participates in platelet signaling and promotes thrombosis. Circulation research. 2014;115:997-1006.
Piedrahita JA, et al. Generation of mice carrying a mutant apolipoprotein e gene inactivated by gene targeting in embryonic stem cells. Proc Natl Acad Sci U S A. 1992;89:4471-4475.
Bragg R, et al. Review of pharmacotherapy options for the management of obesity. J Am Assoc Nurse Pract. 2016;28:107-115.
Flegal KM, et al. Trends in obesity among adults in the united states, 2005 to 2014. JAMA. 2016;315:2284-2291.
Franks PW, et al. Gene-lifestyle and gene-pharmacotherapy interactions in obesity and its cardiovascular consequences. Current vascular pharmacology. 2011;9:401-456.
Steinberg D. Atherogenesis in perspective: Hypercholesterolemia and inflammation as partners in crime. Nat Med. 2002;8:1211-1217.
Blum A. The possible role of red blood cell microvesicles in atherosclerosis. Eur J Intern Med. 2009;20:101-105.
Muller F, et al. Platelet polyphosphates are proinflammatory and procoagulant mediators in vivo. Cell. 2009;139:1143-1156.
Barry OP, et al. Modulation of monocyte-endothelial cell interactions by platelet microparticles. The Journal of clinical investigation. 1998;102:136-144.
Desgranges C, et al. Catabolismof thymidine in human blood platelets: Purification and properties of thymidine phosphorylase. Biochimica et biophysica acta. 1981;654:211-218.
Fox SB, et al. Platelet-derived endothelial cell growth factor/ thymidine phosphorylase expression in normal tissues: An immunohistochemical study. J Pathol. 1995;176:183-190.
Van Kuilenburg AB, et al. Determination of thymidine phosphorylase activity in human blood cells and fibroblasts by a nonradiochemical assay using reversed-phase high-performance liquid chromatography. Nucleosides Nucleotides Nucleic Acids. 2006;25:1261-1264.
Ignatescu MC, et al. Expression of the angiogenic protein, platelet-derived endothelial cell growth factor, in coronary atherosclerotic plaques: In vivo correlation of lesional microvessel density and constrictive vascular remodeling. Arteriosclerosis, thrombosis, and vascular biology. 1999;19:2340-2347.
Li W, et al. Thymidine phosphorylase gene transfer inhibits vascular smooth muscle cell proliferation by upregulating heme oxygenase-1 and p27kip1. Arteriosclerosis, thrombosis, and vascular biology. 2005;25:1370-1375.
Yue H, et al. Thymidine phosphorylase inhibits vascular smooth muscle cell proliferation via upregulation of stat3. Biochimica et biophysica acta. 2012;1823:1316-1323.
Somjen D, et al. Platelet-derived endothelial cell growth factor inhibits DNA synthesis in vascular smooth muscle cells. Am J Hypertens. 1999;12:882-889.
Handa M, et al. Adventitial delivery of platelet-derived endothelial cell growth factor gene prevented intimal hyperplasia of vein graft. J Vasc Surg. 2008;48:1566-1574.
Cizek SM, et al. Risk factors for atherosclerosis and the development of preatherosclerotic intimal hyperplasia. Cardiovascular pathology : the official journal of the Society for Cardiovascular Pathology. 2007;16:344-350.
Hamed EA, et al. Vasculopathy in type 2 diabetes mellitus: Role of specific angiogenic modulators. J Physiol Biochem. 2011;67:339-349.
Toyoda Y, et al. Thymidine phosphorylase regulates the expression of cxcl10 in rheumatoid arthritis fibroblast-like synoviocytes. Arthritis and rheumatism. 2013.
Moore KJ, et al. Macrophages in atherosclerosis: A dynamic balance. Nature reviews. Immunology. 2013;13:709-721.
Mayer RJ, et al. Randomized Trial of tas-102 for refractory metastatic colorectal cancer. N Engl J Med. 2015;372:1909-1919.
Yoshino T, et al. Tas-102 monotherapy for pretreated metastatic colorectal cancer: A double-blind, randomised, placebo-controlled phase 2 trial. The lancet oncology. 2012;13:993-1001.
Doi T, et al. Phase i study of tas-102 treatment in japanese patients with advanced solid tumours. British journal of cancer. 2012;107:429-434.
Hong DS, et al. Phase i study to determine the safety and pharmacokinetics of oral administration of tas-102 in patients with solid tumors. Cancer. 2006;107:1383-1390.
Johansson M. Identification of a novel human uridine phosphorylase. Biochem Biophys Res Commun. 2003;307:41-46.
Roosild TP, et al. A novel structural mechanism for redox regulation of uridine phosphorylase 2 activity. J Struct Biol. 2011;176:229-237.
Kubilus J, et al. Purification of thymidine phosphorylase from human amniochorion. Biochimica et Biophysica Acta (BBA)—Enzymology. 1978;527:221-228.
Miyazono K, et al. Purification and properties of an endothelial cell growth factor from human platelets. The Journal of biological chemistry. 1987;262:4098-4103.
Li W, et al. Transmyocardial laser revascularization induced angiogenesis correlated with the expression of matrix metalloproteinases and platelet-derived endothelial cell growth factor. Eur J Cardiothorac Surg. 2001;19:156-163.
Li PG, et al. Caffeic acid inhibits vascular smooth muscle cell proliferation induced by angiotensin ii in stroke-prone spontaneously hypertensive rats. Hypertens Res. 2005;28:369-377.
Li W, et al. Long-term effect of gene therapy for chronic ischemic myocardium using platelet-derived endothelial cell growth factor in dogs. J Gene Med. 2008;10:412-420.
Koukourakis Mi, et al. Platelet-derived endothelial cell growth factor expression correlates with tumour angiogenesis and prognosis in non-small-cell lung cancer. Br J Cancer. 1997;75:477-481.
Akiyama S, et al. The role of thymidine phosphorylase, an angiogenic enzyme, in tumor progression. Cancer Sci. 2004;95:851-857.
Yamada N, et al. Platelet-derived endothelial cell growth factor gene therapy for limb ischemia. J Vasc Surg. 2006;44:1322-1328.
Souza SJ, et al. Lipid profile of hiv-infected patients in relation to antiretroviral therapy: A review. Revista da Associacao Medica Brasileira. 2013;59:186-198.
De Almeida ER, et al. The roles of genetic polymorphisms and human immunodeficiency virus infection in lipid metabolism. BioMed research international. 2013;2013:836790.

(56) References Cited

OTHER PUBLICATIONS

Longenecker CT, et al. Markers of inflammation and cd8 t-cell activation, but not monocyte activation, are associated with subclinical carotid artery disease in hiv-infected individuals. HIV medicine. 2013;14:385-390.
Derrien T, et al. The gencode v7 catalog of human long noncoding rnas: Analysis of their gene structure, evolution, and expression. Genome Res. 2012;22:1775-1789.
Lee YH, et al. Microarray profiling of isolated abdominal subcutaneous adipocytes from obese vs non-obese pima indians: Increased expression of inflammation-related genes. Diabetologia. 2005;48:1776-1783.
Lopez LC, et al. Unbalanced deoxynucleotide pools cause mitochondrial DNA instability in thymidine phosphorylase-deficient mice. Human molecular genetics. 2009;18:714-722.
Yu S, et al. Adipocyte-specific gene expression and adipogenic steatosis in the mouse liver due to peroxisome proliferator-activated receptor gamma1 (ppargamma1) overexpression. The Journal of biological chemistry. 2003;278:498-505.
Inoue M, et al. Increased expression of ppargamma in high fat diet-induced liver steatosis in mice. Biochemical and biophysical research communications. 2005;336:215-222.
Iltzsch MH, et al. Kinetic studies of thymidine phosphorylase from mouse liver. Biochemistry. 1985;24:6799-6807.
Ryden M, et al. Subcutaneous adipocyte lipolysis contributes to circulating lipid levels. Arteriosclerosis, thrombosis, and vascular biology. 2017;37:1782-1787.
Li W, et al. Ferric chloride-induced murine thrombosis models. J. Vis. Exp. 2016;115:e54479.
Li W, et al. Ferric chloride-induced murine carotid arterial injury: A model of redox pathology. Redox Biol. 2013;1:50-55.
Zhang F, et al. Lacteal junction zippering protects against diet-induced obesity. Science. 2018;361:599-603.
Li W, et al. Cd36 participates in a signaling pathway that regulates ros formation in murine vsmcs. J Clin Invest. 2010;120:3996-4006.
Sztalryd C, et al. The perilipin family of lipid droplet proteins: Gatekeepers of intracellular lipolysis. Biochim Biophys Acta Mol Cell Biol Lipids. 2017;1862:1221-1232.
Boukouris AE, et al. Metabolic enzymes moonlighting in the nucleus: Metabolic regulation of gene transcription. Trends Biochem Sci. 2016;41:712-730.
Matsuda S, et al. Nuclear pyruvate kinase m2 complex serves as a transcriptional coactivator of arylhydrocarbon receptor. Nucleic Acids Res. 2016;44:636-647.
Bell CG. The epigenomic analysis of human obesity. Obesity (Silver Spring). 2017;25:1471-1481.
Yu X, et al. Non-metabolic functions of glycolytic enzymes in tumorigenesis. Oncogene. 2017;36:2629-2636.
Liu H, et al. Thymidine phosphorylase exerts complex effects on bone resorption and formation in myeloma. Sci Transl Med. 2016;8:353ra113.
Li W, et al. Gene therapy for chronic myocardial ischemia using platelet-derived endothelial cell growth factor in dogs. Am J Physiol Heart Circ Physiol. 2005;288:H408-415.
Yue H, et al. Cd36 enhances vascular smooth muscle cell proliferation and development of neointimal hyperplasia. Arteriosclerosis, thrombosis, and vascular biology. 2018:ATVBAHA118312186.
Visser M, et al. Elevated c-reactive protein levels in overweight and obese adults. JAMA. 1999;282:2131-2135.
Hotamisligil GS. Inflammation, metaflammation and immunometabolic disorders. Nature. 2017;542:177-185.
Hotamisligil GS, et al. Nutrient sensing and inflammation in metabolic diseases. Nat Rev Immunol. 2008;8:923-934.
Tsimikas S, et al. Oxidized phospholipids, Ip(a) lipoprotein, and coronary artery disease. N Engl J Med. 2005;353:46-57.
Holvoet P, et al. Oxidized Idl and malondialdehyde-modified Idl in patients with acute coronary syndromes and stable coronary artery disease. Circulation. 1998;98:1487-1494.
Upston JM, et al. Disease stage-dependent accumulation of lipid and protein oxidation products in human atherosclerosis. The American journal of pathology. 2002;160:701-710.
Steinberg D, et al. Is the oxidative modification hypothesis relevant to human atherosclerosis? Do the antioxidant trials conducted to date refute the hypothesis? Circulation. 2002;105:2107-2111.
Otsuka F, et al. Pathology of coronary atherosclerosis and thrombosis. Cardiovasc Diagn Ther. 2016;6:396-408.
Toyoda Y, et al. Thymidine phosphorylase regulates the expression of cxcl10 in rheumatoid arthritis fibroblast-like synoviocytes. Arthritis Rheumatol. 2014;66:560-568.
Rahmati M, et al. Granulocyte-colony stimulating factor related pathways tested on an endometrial ex-vivo model. PloS one. 2014;9:e102286.
Eda H, et al. Cytokines induce thymidine phosphorylase expression in tumor cells and make them more susceptible to 5'-deoxy-5-fluorouridine. Cancer chemotherapy and pharmacology. 1993;32:333-338.
Griffiths L, et al. The influence of oxygen tension and ph on the expression of platelet-derived endothelial cell growth factor/thymidine phosphorylase in human breast tumor cells grown in vitro and in vivo. Cancer research. 1997;57:570-572.
Sawada N, et al. Induction of thymidine phosphorylase activity and enhancement of capecitabine efficacy by taxol/taxotere in human cancer xenografts. Clinical cancer research : an official journal of the American Association for Cancer Research. 1998;4:1013-1019.
Endo M, et al. Induction of thymidine phosphorylase expression and enhancement of efficacy of capecitabine or 5'-deoxy-5-fluorouridine by cyclophosphamide in mammary tumor models. International journal of cancer. Journal international du cancer. 1999;83:127-134.
Sawada N, et al. X-ray irradiation induces thymidine phosphorylase and enhances the efficacy of capecitabine (xeloda) in human cancer xenografts. Clinical cancer research : an official journal of the American Association for Cancer Research. 1999;5:2948-2953.
Gatsiou A, et al. Micrornas in platelet biogenesis and function: Implications in vascular homeostasis and inflammation. Curr Vasc Pharmacol. 2012;10:524-531.
Coppinger JA, et al. Insights into the platelet releasate. Curr Pharm Des. 2007;13:2640-2646.
Gawaz M, et al. Platelets in inflammation and atherogenesis. The Journal of clinical investigation. 2005;115:3378-3384.
Tedgui A, et al. Cytokines in atherosclerosis: Pathogenic and regulatory pathways. Physiol Rev. 2006;86:515-581.
Lievens D, et al. Platelets in atherosclerosis. Thromb Haemost. 2011;106:827-838.
Triques K, et al. Characterization of restrictions to human immunodeficiency virus type 1 infection of monocytes. J Virol. 2004;78:5523-5527.
Bijnsdorp IV, et al. The role of platelet-derived endothelial cell growth factor/thymidine phosphorylase in tumor behavior. Nucleosides, nucleotides & nucleic acids. 2008;27:681-691.
Fox SB, et al. Platelet-derived endothelial cell growth factor/thymidine phosphorylase expression in normal tissues: An immunohistochemical study. The Journal of pathology. 1995;176:183-190.
Tabas I, et al. Macrophage phenotype and function in different stages of atherosclerosis. Circulation research. 2016;118:653-667.
Russo L, et al. Properties and functions of adipose tissue macrophages in obesity. Immunology. 2018;155:407-417.
Lumeng CN, et al. Obesity induces a phenotypic switch in adipose tissue macrophage polarization. The Journal of clinical investigation. 2007;117:175-184.
Shi L, et al. Proteomic investigation of the time course responses of raw 264.7 macrophages to infection with salmonella enterica. Infect Immun. 2009;77:3227-3233.
Martinez R, et al. Comparative proteomic analysis of growth hormone secretagogue a233 treatment of murine macrophage cells j774a.2 indicates it has a role in antiviral innate response. Biochem Biophys Rep. 2016;5:379-387.
Bijnen M, et al. Adipose tissue macrophages do not affect atherosclerosis development in mice. Atherosclerosis. 2018;281:31-37.

(56) References Cited

OTHER PUBLICATIONS

Tabata S, et al. Thymidine phosphorylase activates nfkappab and stimulates the expression of angiogenic and metastatic factors in human cancer cells. Oncotarget. 2014;5:10473-10485.
Gao W, et al. Inhibition of toll-like receptor signaling as a promising therapy for inflammatory diseases: A journey from molecular to nano therapeutics. Front Physiol. 2017;8:508.
Kim S, et al. Differential regulation of toll-like receptor-mediated cytokine production by unfolded protein response. Oxid Med Cell Longev. 2018;2018:9827312.
Zimmers TA, et al. Stat3 in the systemic inflammation of cancer cachexia. Semin Cell Dev Biol. 2016;54:28-41.
Yang X, et al. Toll-like receptor 3 signaling evokes a proinflammatory and proliferative phenotype in human vascular smooth muscle cells. Am J Physiol Heart Circ Physiol. 2006;291:H2334-2343.
Yue H, et al. Role of nuclear unphosphorylated stat3 in angiotensin ii type 1 receptor-induced cardiac hypertrophy. Cardiovasc Res. 2010;85:90-99.
Raskob, GE, et al. Thrombosis: A Major Contributor to the Global Disease Burden. J Thromb Haemost. 2014;12(10):1580-1590.
Murray CJ, et al. Disability-adjusted life years (DALYs) for 291 diseases and injuries in 21 regions, 1990-2010: a systematic analysis for the Global Burden of Disease Study 2010. Lancet. 2012;380(9859):2197-2223.
Jackson SP. Arterial thrombosis—insidious, unpredictable and deadly. Nat Med. 2011;17(11):1423-1436.
Ezumi Y, et al. Physical and functional association of the Src family kinases Fyn and Lyn with the collagen receptor glycoprotein VI-Fc receptor gamma chain complex on human platelets. J Exp Med. 1998;188(2):267-276.
Furie BC, et al. Tissue factor pathway vs. collagen pathway for in vivo platelet activation. Blood Cells Mol Dis. 2006;36(2):135-138.
Stegner D, et al. Platelet receptor signaling in thrombus formation. J Mol Med (Berl). 2011;89(2):109-121.
Smyth SS, Woulfe DS, Weitz JI, et al. G-protein-coupled receptors as signaling targets for antiplatelet therapy. Arteriosclerosis, thrombosis, and vascular biology. 2009;29(4):449-457.
Depta JP, et al. New approaches to inhibiting platelets and coagulation. Annual review of pharmacology and toxicology. 2015;55:373-397.
Franchi F, et al. Novel antiplatelet agents in acute coronary syndrome. Nature reviews Cardiology. 2015;12(1):30-47.
Desai NR, et al. The state of periprocedural antiplatelet therapy after recent trials. JACC Cardiovascular interventions. 2010;3(6):571-583.
De Souza Brito F, et al. Novel anti-platelet agents: focus on thrombin receptor antagonists. Journal of cardiovascular translational research. 2013;6(3):415-424.
Chassot PG, et al. Perioperative antiplatelet therapy: the case for continuing therapy in patients at risk of myocardial infarction. Br J Anaesth. 2007;99(3):316-328.
Capodanno D, et al. Antiplatelet therapy: new pharmacological agents and changing paradigms. J Thromb Haemost. 2013;11 Suppl 1:316-329.
Bronckaers A, et al. Identification of aspartic acid-203 in human thymidine phosphorylase as an important residue for both catalysis and non-competitive inhibition by the small molecule “crystallization chaperone” 5'-O-tritylinosine (KIN59). Biochemical pharmacology. 2009;78(3):231-240.
Liekens S, et al. Targeting platelet-derived endothelial cell growth factor/thymidine phosphorylase for cancer therapy. Biochemical pharmacology. 2007;74(11):1555-1567.
Norman RA, et al. Crystal structure of human thymidine phosphorylase in complex with a small molecule inhibitor. Structure. 2004;12(1):75-84.
Schwartz M. Thymidine phosphorylase from Escherichia coli. Properties and kinetics. European journal of biochemistry / FEBS. 1971;21(2):191-198.
Li W, et al. Thymidine phosphorylase participates in platelet signaling and promotes thrombosis. Circulation research. 2014;115(12):997-1006.
Liekens S, et al. Thymidine phosphorylase is noncompetitively inhibited by 5'-O-trityl-inosine (KIN59) and related compounds. Nucleosides, nucleotides & nucleic acids. 2006;25(9-11):975-980.
Pawlowski CL, et al. Platelet microparticle-inspired clot-responsive nanomedicine for targeted fibrinolysis. Biomaterials. 2017;128:94-108.
Ruggeri ZM, et al. Adhesion mechanisms in platelet function. Circulation research. 2007;100(12):1673-1685.
Gupta N, et al. Proteasome proteolysis supports stimulated platelet function and thrombosis. Arteriosclerosis, thrombosis, and vascular biology. 2014;34(1):160-168.
Srikanthan S, et al. Exosome poly-ubiquitin inhibits platelet activation, downregulates CD36 and inhibits pro-atherothombotic cellular functions. J Thromb Haemost. 2014;12(11):1906-1917.
Woulfe DS. Akt signaling in platelets and thrombosis. Expert Rev Hematol. 2010;3(1):81-91.
Adams HP, Jr., et al. Guidelines for the early management of patients with ischemic stroke: A scientific statement from the Stroke Council of the American Stroke Association. Stroke; a journal of cerebral circulation. 2003;34(4):1056-1083.
Burkhart JM, et al. The first comprehensive and quantitative analysis of human platelet protein composition allows the comparative analysis of structural and functional pathways. Blood. 2012;120(15):e73-82.
Wijten P, et al. High precision platelet releasate definition by quantitative reversed protein profiling—brief report. Arteriosclerosis, thrombosis, and vascular biology. 2013;33(7):1635-1638.
Connolly GC, et al. Emerging risk stratification approaches to cancer-associated thrombosis: risk factors, biomarkers and a risk score. Thromb Res. 2010;125 Suppl 2:S1-7.
Demers M, et al. Cancers predispose neutrophils to release extracellular DNA traps that contribute to cancer-associated thrombosis. Proceedings of the National Academy of Sciences of the United States of America. 2012;109(32):13076-13081.
Goldin-Lang P, et al. Effect of ionizing radiation on cellular procoagulability and co-ordinated gene alterations. Haematologica. 2007;92(8):1091-1098.
Nieswandt B, et al. Platelet-collagen interaction: is GPVI the central receptor? Blood. 2003;102(2):449-461.
Kato K, et al. The contribution of glycoprotein VI to stable platelet adhesion and thrombus formation illustrated by targeted gene deletion. Blood. 2003;102(5):1701-1707.
Ungerer M, et al. Novel antiplatelet drug revacept (Dimeric Glycoprotein VI-Fc) specifically and efficiently inhibited collagen-induced platelet aggregation without affecting general hemostasis in humans. Circulation. 2011;123(17):1891-1899.
Schupke S, et al. Revacept, a Novel Inhibitor of Platelet Adhesion, in Patients Undergoing Elective PCI-Design and Rationale of the Randomized ISAR-PLASTER Trial. Thromb Haemost. 2019;119(9):1539-1545.
Kim S, et al. Akt activation in platelets depends on Gi signaling pathways. J Biol Chem. 2004;279(6):4186-4195.
Yue, H. Thymidine Phosphorylase Plays a Mechanistic Role in Obesity and Atherogenesis. 32nd Annual Health Science Research Day. Marshall University, Joan C. Edwards School of Medicine. Mar. 6, 2019.
Zulfiker, A, et al. Targeting Thymidine Phosphorylase with Tipiracil Hydrochloride is a Safe and Effective Antithrombotic Therapy. Blood. Tracking No. BLD-2020-005480.
Bera, H. et al. “Recent discovery of non-nucleobase thymidine phosphorylase inhibitors targeting cancer.” European Journal of Medicinal Chemistry 124(2016):992-1003.
Reigan, Philip, et al. “Aminoimidazolylmethyluracil Analogues as Potent Inhibitors of Thymidine Phosphorylase and Their Bioreductive Nitroimidazolyl Prodrugs.” J. Med. Chem. 2005, 48, 392-402.

* cited by examiner

Box1

| TRAF6 | LFPDNFAKREILSLMWKC---------------------------------------------------- |
|-------|----------------------------------------------------------------------|
| hTLR1 | ----------------------------------------------DTVFENCGHLTELETLILQWM |
| hTYMP | VFPNQEQARELAKTLVGVGASLGLIRVAAALTAMDKPLGRCVGHALEVEEALLCMD |
| MyD88 | --------------------------------------AGITTLDDPLG----HWPERFDAFICY- |
| MAL   | -----------------------------------TTLDDPLG----HWPERFDAFIC- |

METHODS FOR TREATMENT OF OBESITY, ATHEROSCLEROSIS, AND THROMBOSIS

RELATED APPLICATIONS

This application claims priority from U.S. Provisional Application Ser. No. 62/847,547, filed May 14, 2019, the entire disclosure of which is incorporated herein by this reference.

GOVERNMENT INTEREST

This invention was made with government support under grant number R15HL145573 awarded by the National Institutes of Health. The government has certain rights in the invention.

TECHNICAL FIELD

The presently-disclosed subject matter relates to methods for the treatment of obesity, atherosclerosis, and/or thrombosis. In particular, the presently-disclosed subject matter relates to methods for the treatment of obesity, atherosclerosis, and/or thrombosis that includes reducing an expression level or activity of thymidine phosphorylase in a subject.

BACKGROUND

Obesity is a worldwide epidemic and a major contributor to some of the leading causes of death in the U.S., including heart disease, stroke, diabetes and some types of cancer. People with obesity are also more at risk of developing serious respiratory illness with COVID-19, a novel coronavirus that has led to a worldwide pandemic. Two-thirds of Americans are overweight and the amount of overweight American is often higher in under-served states, such as West Virginia, which has the lowest-health rating of 16.2%. Over the past three decades, the prevalence of overweight individuals and obesity has increased consistently, and no one country has successfully fought against obesity to date. In addition to the genetic susceptibility and sedentary lifestyles combined with excess energy intake, studies have implied that a low-grade and persistent inflammation is a potentially modifiable risk factor for obesity. However, the underling mechanism of obesity still remains unclear, which is a bona fide barrier to developing effective and safe therapeutic strategies.

Along these lines, thrombotic events also remain a clinically significant area for new mechanistic and therapeutic discoveries, as they are a major causes of morbidity and mortality both in the U.S. and worldwide. Yet, new antithrombotic agents are not being developed since suitable targets are lacking. Platelet activation and hyper-aggregation at the site of vascular injury is the primary pathogenic component of thrombosis, which can lead to vessel occlusion resulting in myocardial infarction and ischemic stroke. In this context, platelet surface receptor glycoprotein VI (GPVI) confers both platelet adhesion and activation in response to exposed collagens at the site of vascular injury. The adhered and activated platelets release soluble agonists, including adenosine diphosphate (ADP), thrombin, and thromboxane $A_2$ (TXA2), that activate additional platelets locally via G protein coupled receptors (GPCRs), such as ADP-receptor P2Y12 and thrombin receptor PAR1. Consequently, various anti-platelet drugs, such as aspirin (COX inhibitor), clopidogrel (P2Y12 inhibitor), and vorapaxar (PAR1 inhibitor), have been developed and used clinically for the primary or secondary prevention of platelet-mediated thrombotic events. However, due to the systemic effects of their targets, these drugs have major side effects including injury to the gastrointestinal mucosa, thrombocytopenia, and systemic hemorrhage. The permanent inhibition on platelet function is also problematic for patients who need emergent surgery. In addition, some patients do not respond to the current anti-platelet regimens and still have a high incidence of vascular thrombosis. Therefore, there are significant clinical interests in elucidating unique molecular mechanisms of platelet-mediated thrombus formation, which can lead to the development of a novel anti-platelet therapy with minimized systemic risks. Currently, all anti-platelet drugs target platelet surface receptors and drugs that safely inhibit platelet function by targeting intracellular proteins have not been developed. Indeed, even while aspirin irreversibly inhibits the production of thromboxane A2, which activates the platelet thromboxane receptor, it is still the case that the antiplatelet effect of aspirin is via targeting of the platelet surface receptor.

Human thymidine phosphorylase (TYMP) was first isolated from amniochorion and later from human platelets, and is thus also known as platelet-derived endothelial cell growth factor. TYMP is mainly found inside the cell due to the lack of an amino-terminal hydrophobic leader sequence required for cell secretion. TYMP belongs to the family of pyrimidine nucleoside phosphorylase, and its primary function is to drive the salvage pathway of pyrimidine nucleosides. In the presence of inorganic phosphate, TYMP reversibly catalyzes thymidine to thymine and 2-D-deoxyribose-1-phosphate (2DDRP), and the latter is further degraded to 2-D-deoxyribose (2DDR). TYMP also has deoxyribosyl transferase activity through transferring the deoxyribosyl moiety from a pyrimidine nucleoside to another pyrimidine base, resulting in the formation of a new pyrimidine nucleoside. Functional TYMP acts as a homodimer and plays a key role in the pyrimidine nucleoside metabolism, ensuring a sufficient pyrimidine nucleotide pool for DNA repair and replication. Through its proline-rich N-terminus, TYMP also binds to Src family kinases (SFKs) Lyn, Fyn, and Yes. Fyn plays a role in various cellular responses such as insulin signaling, cell growth, and oxidative stress, but also inhibits diet-induced adipogenesis and obesity. Furthermore, several inflammatory cytokines, including TNFα, IL-1, IL-6, IL-8, IL-17, interferon-γ (IFN-γ), and granulocyte-colony stimulating factor (G-CSF) can induce TYMP expression.

Despite the studies into the role of TYMP, however, the role of TYMP in the pathogenesis of obesity, atherosclerosis, and thrombosis still remains unclear. The role of TYMP in platelets, a non-nucleated cell, remains to be fully elucidated and while TYMP is present in the lipid rich core of human atherosclerotic lesions, its function remains unknown. It is appreciated that TYMP possesses signaling function, and TYMP deficiency in mice dramatically reduces platelet activation. However, whether TYMP plays a role in the development of obesity has never been studied and its function in liver biology is not yet known.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes methods for the treatment of obesity, atherosclerosis, and/or thrombosis. In particular, the presently-disclosed subject matter includes methods for the treatment of obesity, atherosclerosis, and/or thrombosis that includes reducing an expression level or activity of thymidine phosphorylase in a subject.

In some embodiments of the presently-disclosed subject matter, a method of treating obesity is provided that comprises reducing an expression level or activity of a thymidine phosphorylase in a subject in need thereof. In some embodiments, reducing the expression level or activity of thymidine phosphorylase comprises administering to the subject an effective amount of a thymidine phosphorylase inhibitor. In some embodiments, the thymidine phosphorylase inhibitor is tipiracil. In some embodiments, the subject is a male subject.

With respect to the treatment of obesity via the reduction in an expression level or activity of thymidine phosphorylase, in some embodiments, reducing the expression level or activity of thymidine phosphorylase reduces an expression level of lipogenesis markers, such as, in certain embodiments, acetyl co-A carboxylase, peroxisome proliferator-activated receptor gamma, and a combination thereof. In some embodiments, reducing the expression level or activity of thymidine phosphorylase reduces an expression level or activity of a mitogen activated protein kinase (MAPK), such as a mitogen activated protein kinase selected from p38, ERK1/2, and JNK2. In some embodiments, reducing the expression level or activity of thymidine phosphorylase increases an expression level of a lipolysis protein, an adipose triglyceride lipase, or combinations thereof. In some embodiments, reducing the expression level or activity of thymidine phosphorylase reduces an activity level of NF-κB.

In some embodiments, reducing the expression level or activity of thymidine phosphorylase reduces an expression level of an inflammatory cytokine, such as TNFα, IL-1, IL-6, IL-8, IL-17, interferon-γ, granulocyte-colony stimulating factor, Toll-like receptor, and combinations thereof. In some embodiments, reducing the expression level or activity of thymidine phosphorylase reduces an expression level or activity of a glycolysis-associated protein, such as, in certain embodiments, fructosebisphosphate aldolase (FBPA), glyceraldehyde-3-phosphate dehydrogenase (GAPDH), and pyruvate kinase muscle isoform M2 (PKM2). In some embodiments, reducing the expression level or activity of thymidine phosphorylase increases an amount of glucose tolerance in the subject. In some embodiments, reducing the expression level or activity of thymidine phosphorylase decreases body weight of the subject, reduces lipid accumulation in a liver of the subject, and/or reduces an amount of atherosclerotic plaques in one or more blood vessels of the subject.

Further provided, in some embodiments of the presently-disclosed subject matter, are methods for treating atherosclerosis. In some embodiments, a method of treating atherosclerosis is provided that comprises reducing an expression level or activity of a thymidine phosphorylase in a subject in need thereof including via the administration of a thymidine phosphorylase inhibitor, such as tipiracil. In some embodiments, reducing the expression level or activity of the thymidine phosphorylase reduces an expression level of lipogenesis markers, such as acetyl co-A carboxylase, peroxisome proliferator-activated receptor gamma, or a combination thereof. In some embodiments, reducing the expression level or activity of the thymidine phosphorylase reduces an expression level of a mitogen activated protein kinases (MAPK), such as p38, ERK1/2, and JNK2. In some embodiments, reducing the expression level or activity of the thymidine phosphorylase reduces a level of active NF-κB (p-p65T254). In some embodiments, reducing the expression level or activity of the thymidine phosphorylase reduces an expression level of an inflammatory cytokine, such as TNFα, IL-1, IL-6, IL-8, IL-17, interferon-γ, granulocyte-colony stimulating factor, Toll-like receptor, and combinations thereof.

Still further provided, in some embodiments of the presently-disclosed subject matter, are methods for treating thrombosis. In some embodiments, a method of treating thrombosis is provided that comprises reducing an expression level or activity of a thymidine phosphorylase in a subject in need thereof. In some embodiments, reducing the expression level or activity of thymidine phosphorylase comprises administering to the subject an effective amount of a thymidine phosphorylase inhibitor to treat the thrombosis. In some embodiments, the thymidine phosphorylase inhibitor is tipiracil.

In some embodiments of the therapeutic methods for the treatment of thrombosis, administering the effective amount of the thymidine phosphorylase inhibitor reduces an amount of platelet activation and aggregation. In some embodiments, the thrombosis is hyperlipidemia-enhanced thrombosis. In some embodiments, the subject has type II diabetes. In some embodiments, the tipiracil can be administered alone or in combination with other therapeutic agents, such as, in certain embodiments, an effective amount of a tissue plasminogen activator (tPA) or an effective amount of aspirin. In some embodiments where tipiracil is co-administered with tPA or aspirin, the effective amount of tPA or aspirin that is administered is reduced as compared to the amount of tPA or aspirin that would be administered when those agents are administered individually for the treatment of thrombosis.

Further features and advantages of the present invention will become evident to those of ordinary skill in the art after a study of the description, figures, and non-limiting examples in this document.

BRIEF DESCRIPTION OF THE DRAWINGS

(FIG. 1A) a schematic diagram showing the results of a search of the EMBL-EBI database for TYMP expression, where the numbers represent TYMP gene expression levels; (FIG. 1B) a graph showing TYMP expression in obese humans (GDS3602); and (FIG. 1C) a graph showing results of a quantitative polymerase chain reaction (qPCR) assay of TYMP mRNA expression in lean and obese human visceral fat tissue.

(FIG. 2A) a graph showing the results of an experiment where eight-week old male WT and $Tymp^{-/-}$ mice were fed with a WD (TD.88137) and body weight was monitored weekly for 8 wks (*<0.05); (FIGS. 2B-2C) graphs showing, at the time of sacrifice, measurements of liver weight and abdominopelvic fat pat weight along with graphs showing the data presented as a ratio to body weight (inset); and (FIGS. 2D-2E) graphs showing plasma levels of HDL and LDL/VLDL (MAK045) as well as liver TAG (MAK266) quantitatively analyzed using assay kits purchased from Millipore-Sigma.

(FIG. 4A) an image showing the whole cell lysates (W) or nuclear extracts (N) that were prepared from VSMC overexpressing TYMP (C2) and used for immunoprecipitation (IP) of TYMP, where IP with normal isotype IgG served as control, where IPs were resolved in SDS-PAGE, and stained with Coomassie blue, and where bands were analyzed by mass spectrometry; (FIG. 4B) an image showing a Western blot assay of the proteins identified by mass spectrometry, where Myocin-9 is non-specific, but Col1A1 is specific; (FIG. 4C) an image showing TYMP expression in liver of age-matched male mice fed chow diet (CD) and WD; (FIG. 4D) an image of a Western Blot showing expression of the indicated proteins in $Tymp^{-/-}$ mice; and (FIG. 4E) an image showing human primary liver cell line, THLE-3 cells were transient transfected with pCDNA6B-hTYMP, and expression of the indicated proteins were examined 48 hrs later by Western blot.

FIG. 12D shows the enlarged thrombi about 10 seconds later.

DESCRIPTION OF EXEMPLARY EMBODIMENTS

Figure 1A:
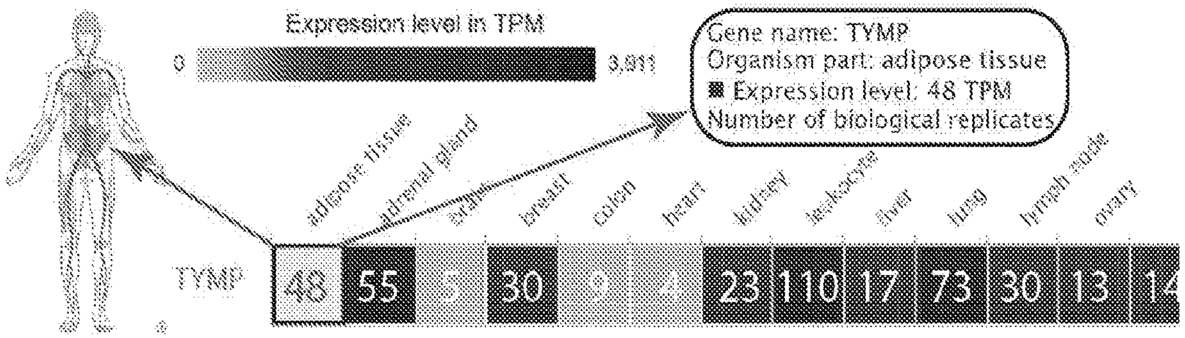
FIGS. 1A-1C include a schematic diagram and graphs showing thymidine phosphorylase (TYMP) expression in obesity, including.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, and in some embodiments 0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the discovery that thymidine phosphorylase (TYMP) has a signaling function, and is necessary for platelet activation and thrombosis. In particular, it was found that TYMP presents in the lipid-rich core of human atherosclerotic lesions and plays a role in obesity and atherogenesis. As described in detail below, it was found that adipose tissue expresses a high level of TYMP, and that TYMP is significantly increased in obese patients. By feeding wild type (WT) and $Tymp^{-/-}$ mice with a western diet (WD, TD.88137, 42% calories from fat), it was found that TYMP deficiency dramatically reduced body weight gain. $Tymp^{-/-}$ mice had less liver and visceral fat weight. TYMP deficiency also dramatically reduced expression of lipogenesis markers and increased expression of lipolysis protein, adipose triglyceride lipase. TYMP deficiency significantly improved glucose tolerance in both male and female subjects. Further, TYMP deficiency significantly reduced WD-induced activation of p38, ERK1/2, and JNK2 in the liver. Overexpression of TYMP in vascular smooth muscle cells (VSMCs) induced constitutive p65 (T254) phosphorylation, which was not seen in the control cells. Toll-like receptor (TLR) 1/2 agonist, Pam3CSK4 had no effect on control cells, however, significantly increased NF-κB activation in TYMP overexpressing VSMCs. Moreover, by pulling down TYMP using nuclear extracts and mass spectrometry analysis, it was found that TYMP co-precipitated with fructosebisphosphate aldolase (FBPA), glyceraldehyde-3-phosphate dehydrogenase (GAPDH), and pyruvate kinase muscle isoform M2 (PKM2), key enzymes in the glycolysis pathway. Gavage feeding of $Apoe^{-/-}$ mice under WD with a TYMP inhibitor likely attenuated lipid deposition in liver and reduced atherosclerotic lesion. Accordingly, it was believed that TYMP plays a key role in regulating glucose and lipid metabolism, inflammation, and, in turn, the development of obesity, which is important for atherogenesis. To that end, the presently-disclosed subject matter thus includes methods for treatment of obesity, atherosclerosis, and/or thrombosis that are based on targeted TYMP-inhibition.

In some embodiments of the presently-disclosed subject matter, a method of treating obesity, atherosclerosis, and/or thrombosis is provided that comprising reducing an expression level or activity of a thymidine phosphorylase in a subject in need thereof. In some embodiments, reducing the expression level or activity of thymidine phosphorylase comprises administering to the subject a thymidine phosphorylase inhibitor. In some embodiments of the therapeutic methods, administering the effective amount of the thymidine phosphorylase inhibitor reduces an amount of platelet activation and aggregation. In some embodiments, the thrombosis is hyperlipidemia-enhanced thrombosis. In some embodiments, the subject has type II diabetes.

With respect to the thymidine phosphorylase inhibitors that can be utilized, in some embodiments, the inhibitor utilized is a genetic inhibitor such as siRNA, miRNA, shRNA, CRISPR, small molecule inhibitors, peptide or protein inhibitors including antibodies. In some embodiments, the thymidine phosphorylase inhibitor is tipiracil, whose chemical structure is provided below.

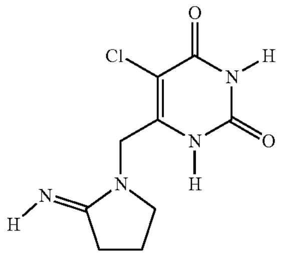

Tipiracil

The term "obesity," as used herein, refers to conditions in which excess body fat has accumulated to the extent that it may have a negative effect on health, which can, in turn, lead to reduced life expectancy and/or increased health problems. In certain instances, a subject can be considered obese when their body mass index (BMI), a measurement obtained by dividing a subject's weight by the square of the person's height, is greater than 20 $kg/m^2$, 21 $kg/m^2$, 22 $kg/m^2$, 23 $kg/m^2$, 24 $kg/m^2$, 25 $kg/m^2$, 26 $kg/m^2$, 27 $kg/m^2$, 28 $kg/m^2$, 29 $kg/m^2$, 30 $kg/m^2$, or more. Obesity can also coincide with conditions such as, but not limited to, hyperinsulinemia, insulin resistance, diabetes, hypertension, and dyslipidemia. Obesity can further be a risk factor for cardiovascular disease. In some instances, obesity can also be characterized by one or more of fasting glucose levels of at least 100 mg/dl, plasma triglyceride levels of at least 150 mg/dl, HDL cholesterol below 40 mg/dl in men and below 50 mg/dl in women, blood pressure of at least 130/85 mm Hg, and abdominal waist circumference of greater than 40 inches for men and greater than 35 inches for women.

The term "diabetes" is used herein to generally refer to a disease wherein a subject's hemoglobin A1C (A1C) is greater than or equal to 6.5%, fasting plasma glucose is greater than or equal to 126 mg/dL, an oral glucose tolerance test two hour blood glucose level is greater than or equal to 200 mg/dL, a casual (i.e. randomly taken) blood glucose level is greater than or equal to 200 mg/dL. In certain instance, "diabetes" also refers to a disease wherein a subject's body is insulin resistant, i.e. no longer responds to insulin.

The term "atherosclerosis" is used herein to refer a disease in which a subject's blood vessel are narrowed, enlarged, or hardened. Such changes in blood vessel integrity may be caused by the buildup of plaque in the vessels or, in other words, the buildup of fat, cholesterol, calcium, and other substances found in the blood. Over time, plaque hardens and narrows the arteries which, in turn, limits the flow of oxygen-rich blood to organs and other parts of a subject's body. In this regard, "atherosclerosis" can, in certain embodiments, be characterized by a weak or absent pulse below the narrowed area of an artery, decreased blood pressure in an affected limb, or whooshing sounds (bruits) over arteries that are heard via stethoscope.

The term "thrombosis" is used herein to refer to the formation of a blood clot inside a blood vessel, which, in turn, obstructs the flow of blood through the blood vessel and circulatory system. Thrombosis can include both venous thrombosis, where the blood clot is located within and blocks the flow of blood through a vein, as well as arterial thrombosis, where the blood clot is located within and blocks the flow of blood through an artery. Such venous thrombi can caused by, among other things, disease or injury to the leg veins, immobility, broken bones, medications, obesity, inherited disorders, or autoimmune disorders, while arterial thrombi are typically caused by a hardening of the arteries, called arteriosclerosis, such as what occurs when plaque buildup in artery walls suddenly burst and are followed by a blood clot.

With respect to the treatment of obesity, atherosclerosis, and/or thrombosis described herein, the terms "treatment" or "treating" are used herein to refer any treatment of a condition of interest (e.g., obesity), including but not limited to prophylactic treatment and therapeutic treatment. As such, the terms "treatment" or "treating" include, but are not limited to: reducing the development or likelihood of development of a condition of interest; inhibiting the progression of a condition of interest; arresting or reducing the further development of a condition of interest; reducing the severity of a condition of interest; ameliorating or relieving symptoms associated with a condition of interest; and causing a regression of a condition of interest or one or more of the symptoms associated with a condition of interest.

For administration of a therapeutic composition as disclosed herein (e.g., a TYMP inhibitor), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/$m^2$. In some embodiments that make use of a TYMP inhibitor, such as tipiracil, the inhibitor is administered to the subject at a dose of about 1 mg/kg/day.

Suitable methods for administering a therapeutic composition in accordance with the methods of the presently-disclosed subject matter include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Regardless of the route of administration, the inhibitors utilized in accordance with the presently-disclosed subject matter are typically administered in amount effective to achieve the desired response. As such, the term "effective amount" is used herein to refer to an amount of the therapeutic composition (e.g., a TYMP inhibitor and a pharmaceutically vehicle, carrier, or excipient) sufficient to produce a measurable biological response (e.g., a decrease in inflammation or body weight). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

In some embodiments of the therapeutic methods for the treatment of obesity, atherosclerosis, and/or thrombosis, the therapeutic agents used in accordance with the presently-disclosed subject matter (e.g., the thymidine phosphorylase inhibitors such as tipiracil) can be used alone or in combination with other therapeutic agents capable of treating obesity, atherosclerosis, and/or thrombosis. In some embodiments, administration of thymidine phosphorylase inhibitor in combination with other therapeutic agents allows for a synergistic effect and/or allows for a lower of dose of each agent to be utilized relative to the dose that would should be required should a single therapeutic agent be administered by itself. For instance, in some embodiments, tipiracil can be administered alone or in combination with other therapeutic agents, such as, in certain embodiments, an effective amount of a tissue plasminogen activator (tPA) or an effective amount of aspirin for the treatment of thrombosis. In some embodiments where tipiracil is co-administered with tPA or aspirin, the effective amount of tPA or aspirin that is administered is reduced as compared to the amount of tPA or aspirin that would be administered when those agents are administered individually for the treatment of thrombosis.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

In some embodiments of the presently-disclosed subject matter, reducing the expression level or activity of TYMP, such as through the administration of a TYMP inhibitor, reduces one or more factors and/or symptoms associated with obesity, atherosclerosis, and/or thrombosis in a subject. For instance, in some embodiments, reducing the expression level or activity of thymidine phosphorylase reduces an expression level of lipogenesis markers, such as in certain embodiments, lipogenesis markers selected from the group consisting of acetyl co-A carboxylase, peroxisome proliferator-activated receptor gamma, and a combination thereof. In some embodiments, reducing the expression level or activity of thymidine phosphorylase reduces expression of a mitogen activated protein kinase (MAPK), such as, in some embodiments, p38, ERK1/2, and/or JNK2. In some embodiments, reducing the expression level or activity of thymidine phosphorylase increases an expression level of a lipolysis protein, an adipose triglyceride lipase, or combinations thereof. In some embodiments, reducing the expression level or activity of thymidine phosphorylase reduces an expression or activity level of NF-κB. In some embodiments, reducing the expression level or activity of thymidine phosphorylase reduces an expression level of an inflammatory cytokine such as, in some embodiments, an inflammatory cytokine selected from the group consisting of: TNFα, IL-1, IL-6, IL-8, IL-17, interferon-γ, granulocyte-colony stimulating factor, Toll-like receptor, and combinations thereof. In some embodiments, reducing the expression level or activity of thymidine phosphorylase improves tolerance to glucose.

Various methods known to those skilled in the art can be used to determine an increase or a reduction in the above-described factors and symptoms associated with obesity, atherosclerosis, and/or thrombosis in a subject. For example, in certain embodiments, the amounts of expression of a lipogenesis marker in a subject can be determined by probing for mRNA or protein of the lipogenesis marker in a biological sample obtained from the subject (e.g., a tissue sample, a urine sample, a saliva sample, a blood sample, a serum sample, a plasma sample, or sub-fractions thereof) using any RNA or protein identification assay known to those skilled in the art. For instance, in some embodiments, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, CA). Because the probes to which the nucleic acid molecules of the sample are bound are known, the molecules in the sample can be identified. In this regard, DNA probes for one or more of the mRNAs of interest can be immobilized on a substrate and provided for use in practicing a method in accordance with the presently-disclosed subject matter.

With further regard to determining increases or reductions in the above-described factors and symptoms associated with obesity, atherosclerosis, and/or thrombosis in samples, and as further examples, chromatography, histology, mass spectrometry, and/or immunoassay devices and methods can also be used to measure the factors, including inflammatory cytokines or chemokines, in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety. Any suitable immunoassay can be utilized, for example, enzyme-linked immunoassays (ELISA), radioimmunoassays (RIAs), competitive binding assays, and the like. Specific immunological binding of the antibody to the inflammatory or other molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

With still further regard to the various therapeutic methods described herein, although certain embodiments of the methods disclosed herein only call for a qualitative assessment (e.g., the presence or absence of lipogenesis markers in a sample), other embodiments of the methods call for a quantitative assessment (e.g., an amount of increase in the level of inflammatory cytokines). Such quantitative assessments can be made, for example, using one of the above mentioned methods, as will be understood by those skilled in the art.

The skilled artisan will also understand that measuring an increase or a reduction in the amount of a certain feature (e.g., body weight or amount of fat) or an improvement in a certain feature (e.g., inflammation) in a subject is a statistical analysis. For example, a reduction in an amount of triglycerides in the subject can be compared to control level of triglycerides, and an amount of triglycerides of less than or equal to the control level can be indicative of a reduction in the amount of triglycerides, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. In some embodiments, the subject is a male subject.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials & Methods for Examples 1-12

Database Search. The EMBL-EBI database-Expression Atlas was searched. The Gene Expression Omnibus (GEO) was also searched using key words "TYMP+obesity" or "TYMP+lipid".

Animals. The $Tymp^{-/-}$ mouse strain has been backcrossed with C57BL6/J wild type mice (WT) for more than 10 generations to produce $Tymp^{-/-}$ animals with a homogeneous nuclear DNA background. This mouse strain does not have observable clinical phenotype under chow diet feeding and when consuming similar food weekly.

Cells. Using a rat vascular smooth muscle cell (VSMC) cell line, C2, which overexpresses human TYMP, TYMP was immunoprecipitated using whole cell lysate or nuclear extract, resolved in SDS-PAGE, and then stained with coomassie blue.

Glucose Tolerance Test. To test the hypothesis that TYMP plays a role in insulin resistance, an intraperitoneal glucose tolerance test (IPGTT) was performed on mice fed with a high fat diet (HFD), which were used for studying the role of TYMP on T2DM-associated thrombotic diathesis. Eight week-old WT and $Tymp^{-/-}$ mice were fasted overnight, and then fasting blood glucose (FBG) levels were measured. The mice were then given an intraperitoneal injection of glucose solution at a concentration of 2 mg/g body weight, and blood glucose levels were measured at the scheduled time points using a Roche AccuCheck Active. The mice were then fed with HFD for 16 weeks, and IPGTT data were collected again with a glucose loading dose at 1 mg/g body weight before they were sacrificed.

Generation of $Tymp^{-/-}/Apoe^{-/-}$ mice. TYMP null mice are on a C57BL6 background, which is resistant to atherosclerotic plaque formation. To directly examine the role of TYMP on atherogenesis, $Tymp^{-/-}$ mice were crossed with $Apoe^{-/-}$ (Jackson Laboratory) mice and a $Tymp^{-/-}/Apoe^{-/-}$ mouse strain was generated. APOE is located on the surface of plasma lipoproteins, functions as a ligand for the LDL receptor (LDLr) and certain LDLr-related proteins, thus playing a central role in the uptake of atherogenic particles from the circulation. Apoe null mice have a markedly altered plasma lipid profile compared to normal mice and rapidly develop atherosclerotic lesions when feed WD. The atherosclerotic lesions in this model resemble human atheroma histologically and the model has been widely used to discover the contributions of specific cells, genes and proteins to atherogenesis. The absence of Tymp and Apoe genes in this new strain was confirmed by RT-PCR. The ratio of each genotype of the offspring matches the Mendel's laws, suggesting that no embryonic death when double knocking out Tymp and Apoe genes. The $Tymp^{-/-}/Apoe^{-/-}$ mice are fertile and there was no apparent phenotype found when they were born. The average body weight of the $Tymp^{-/-}/Apoe^{-/-}$ mice is comparable to the age-matched $Apoe^{-/-}$ mice.

Example 1—Expression of TYMP is Increased in Obesity

Figure 1B:
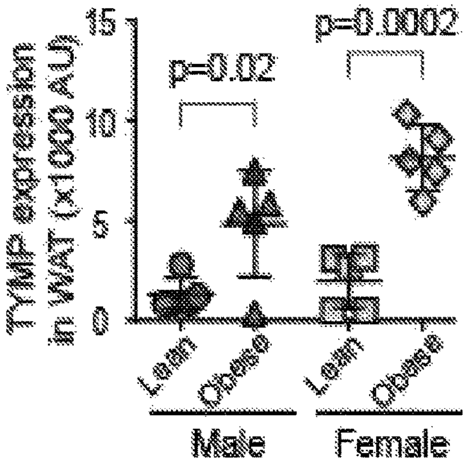
Figure 1C:
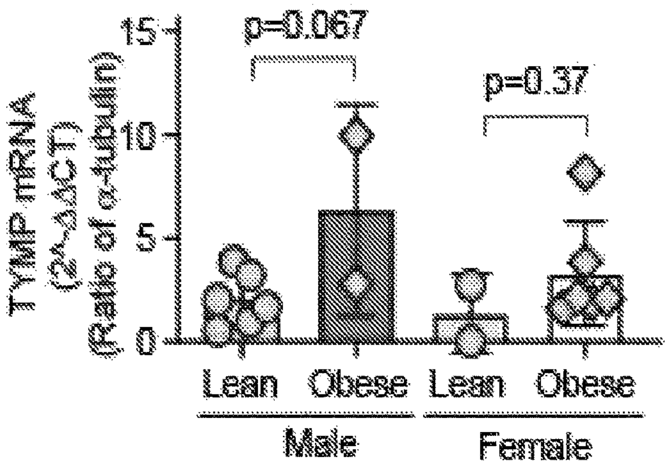

To determine the potential role of TYMP in obesity and dyslipidemia, the EMBL-EBI database-Expression Atlas was searched. As shown in FIG. 1A, white adipose tissue is ranked #4 among tissues that express a high level of TYMP. Further, by searching the *EBI database-Expression Atlas*, it was found that both liver and white adipose tissue have higher TYMP expression. To examine the potential role of TYMP in obesity, the GEO (Gene Expression Omnibus) profile was also searched using the key words "TYMP+obesity" or "TYMP+lipid", and data was found showing that TYMP expression was significantly increased in both male and female obese patients (FIG. 1B). To confirm this observation, TYMP expression was measured in the visceral fat tissues harvested from lean (BMI<25) and obese people (BMI>45). As shown in FIG. 1C, although no significant difference was found between groups due to the low sample size, it was found that TYMP mRNA expression does tend to be increased in the male obese people. GEO data from another study also implied high TYMP level in livers of the obesity-prone rats than in the obesity-resistant animals. These data led to the hypothesis that TYMP contributes to the development of obesity.

Figure 2A:
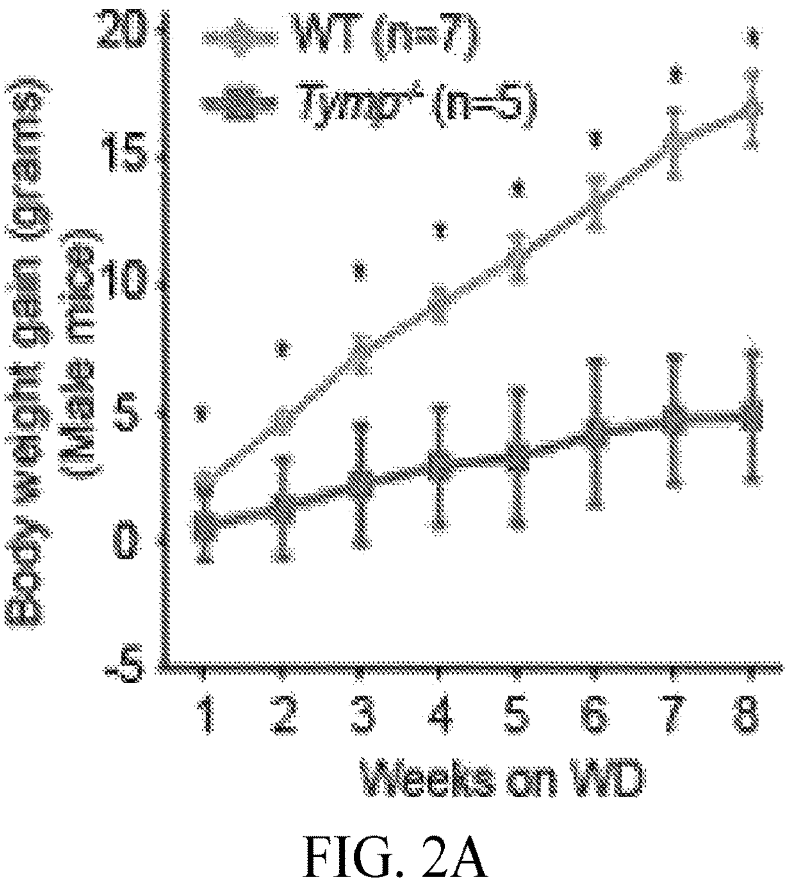
FIGS. 2A-2E include graphs showing that TYMP deficiency inhibits diet-induced obesity in mice, including.
Figure 2B:
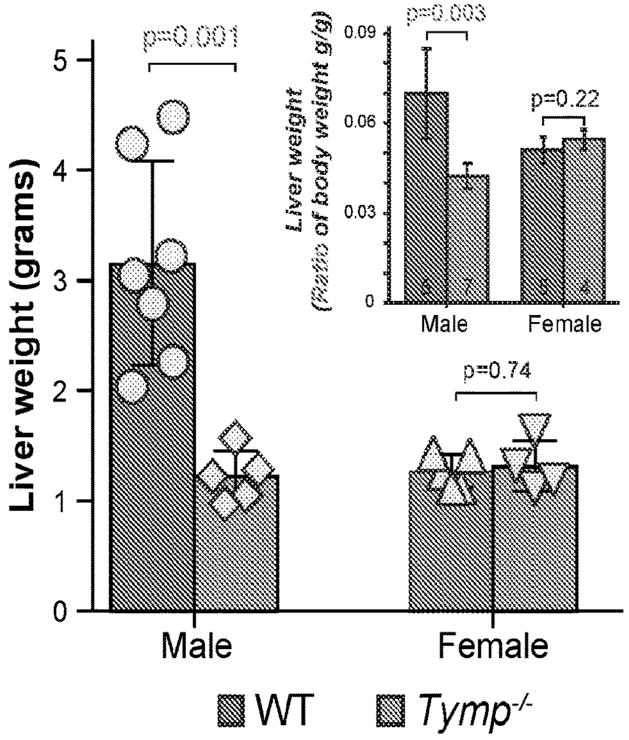
Figure 2C:
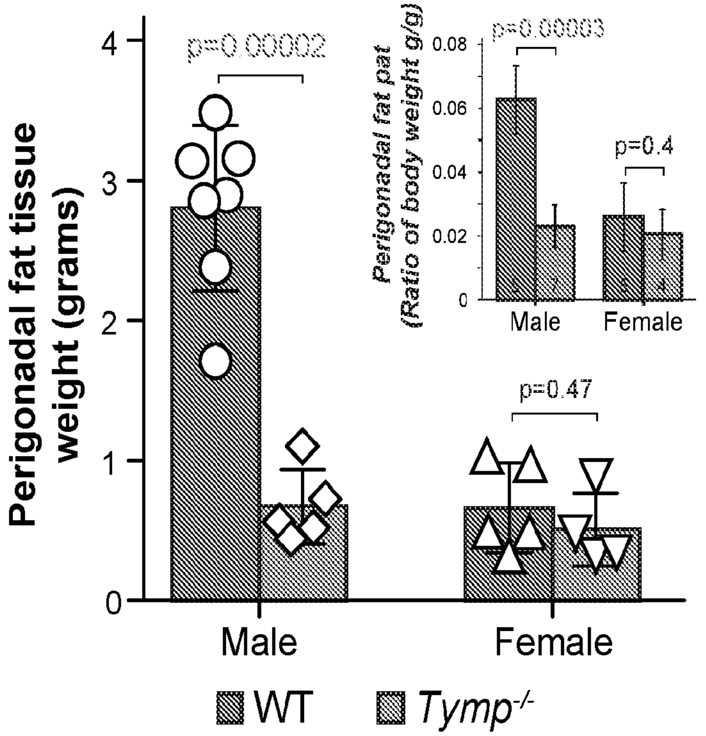
Figure 2D:
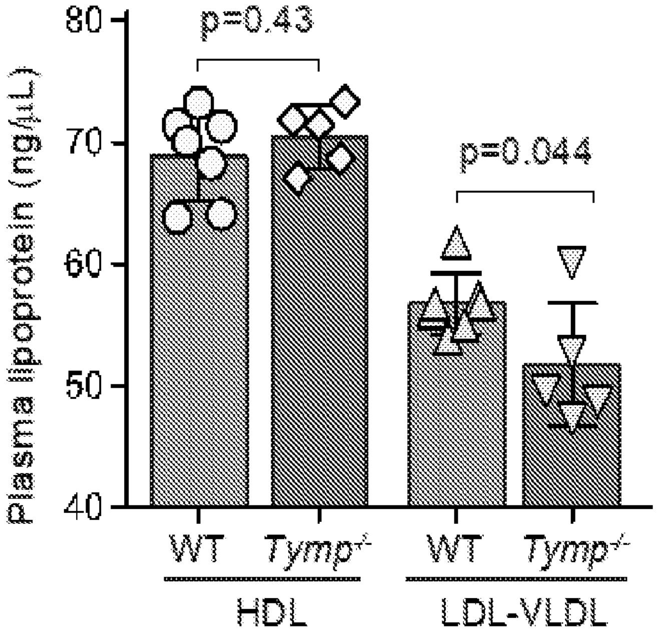
Figure 2E:
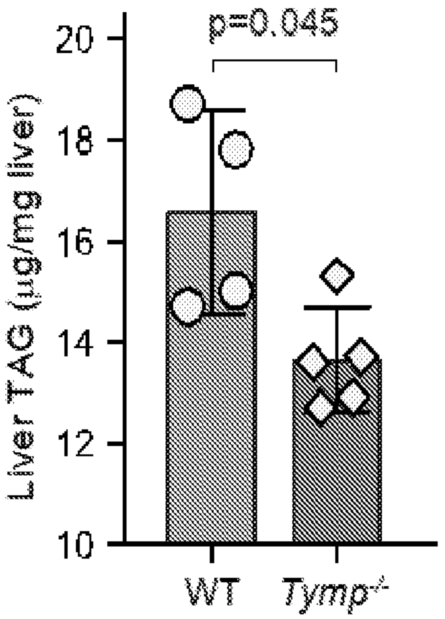

Example 2—TYMP Deficiency Attenuates Gain of Body Weight Upon High Fat Diet Feeding To further examine the hypothesis that TYMP favors the development of obesity, WT and Tymp−/− mice were fed a WD starting from 8 weeks (wks) old. As noted, the $Tymp^{-/-}$ mouse strain has been backcrossed with WT mice for more than 10 generations to produce the $Tymp^{-/-}$ animals with a homogeneous nuclear DNA background. This mouse strain does not have any observable phenotype under chow diet feeding and have normal mitochondrial function. While WD-induced gain of body weight (BW) was similar in female WT and $Tymp^{-/-}$ mice, TYMP deficiency dramatically decreased BW gain of male animals (FIG. 2A). Liver and perigonadal fat weight were also significantly decreased in the male $Tymp^{-/-}$ mice (FIGS. 2B-2C). TYMP deficiency has no effect on plasma level of HDL, but significantly decreased levels of LDL/VLDL (FIG. 2D) and liver TAG (FIG. 2E). These data indicated that TYMP does lead to the development of obesity and may play a role in lipid metabolism.

Figure 3:
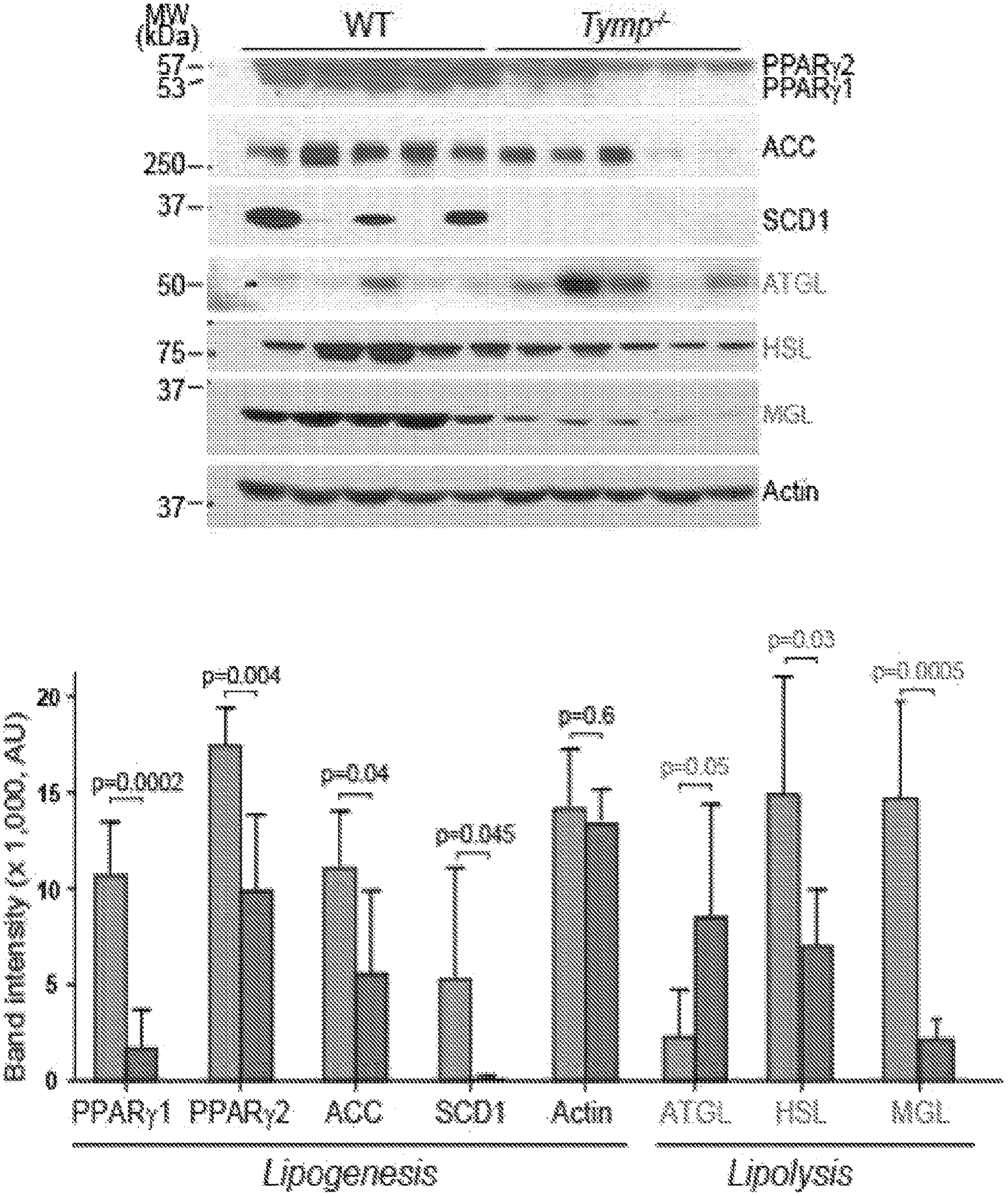
FIG. 3 includes images and a graph showing TYMP deficiency leads to discriminative expression of proteins related to lipid metabolism, where tissue lysates prepared from livers of WT and $Tymp^{-/-}$ mice on WD for 8 weeks were analyzed by Western blot, where band intensity was analyzed by Image J, and t test were used for statistical analysis, and where actin was used as loading control.

Example 3—TYMP Deficiency Changes Expression of Proteins Related to Lipogenesis and Lipolysis To understand the mechanistic role of TYMP that led to the reduced gain of body weight in the $Tymp^{-/-}$ mice, expression of several lipogenesis markers was analyzed using liver lysates prepared from the WD-fed mice by Western blot (FIG. 3). TYMP deficiency dramatically reduced expression of ACC (acetyl Co-A carboxylase) and PPARγ (peroxisome proliferator-activated receptor gamma) 1 and 2, but increased expression of ATGL (adipose triglyceride lipase). ATGL selectively performs the first and rate-limiting step, hydrolyzing triacylglycerols to generate diacylglycerols and free fatty acids (FAA). Overexpression of PPARγ in $PPAR\alpha^{-/-}$ mice induces expression of adipocyte-specific genes and lipogenesis-related genes in the liver and leads to hepatic steatosis. PPARγ signaling pathway also contributes in the high fat diet-induced liver steatosis. The findings indicated that TYMP can enhance lipogenesis in liver and other organs. GAPDH is significantly reduced in the $Tymp^{-/-}$ livers, which grants TYMP another potential function: glycolysis. Taken together, these data clearly indicated that TYMP does play an important role in regulating lipid metabolism.

Figure 4A:
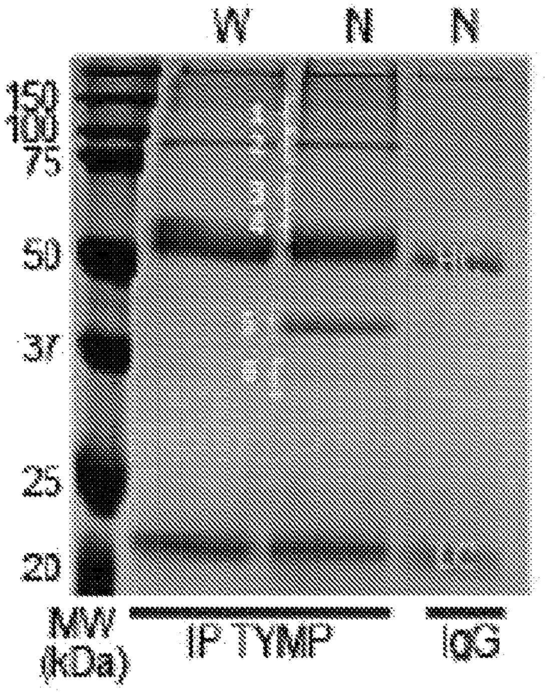
FIGS. 4A-4E are images showing TYMP presents in both cytoplasm and nucleus, and forms associations with or affects expression of a plethora of proteins, including.
Figure 4B:
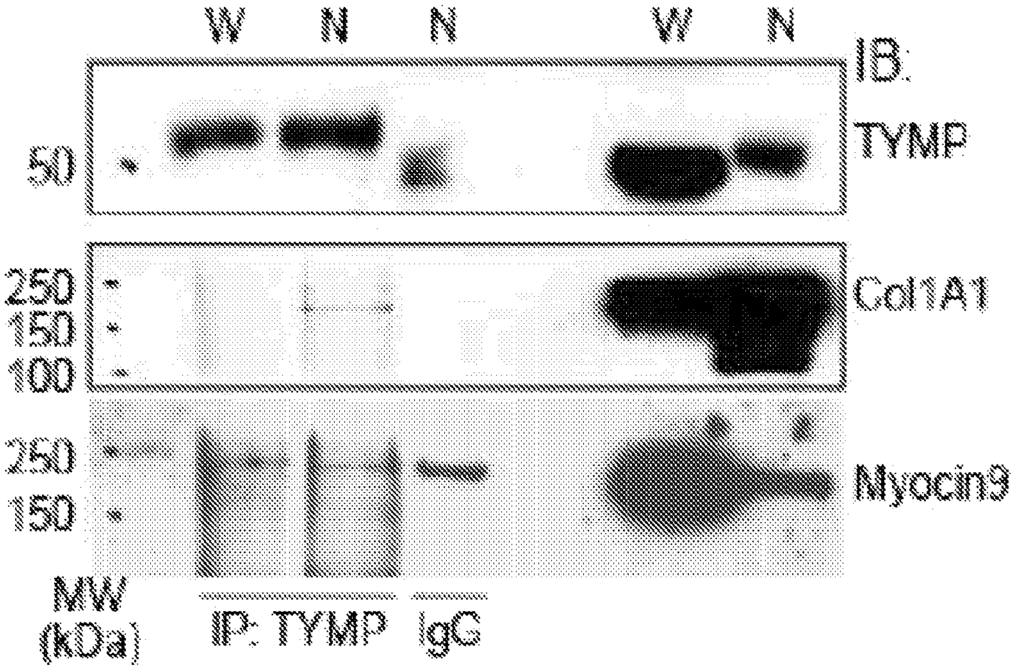

Example 4—TYMP Binds to Plethora of Proteins in Nuclei and Some of them are Enzymes in Glycolysis Pathway TYMP presents in both cytoplasm and nucleus, however its nuclear function is unknown. Using a rat VSMC cell line, C2, which overexpresses human TYMP and immunoprecipitation (IP) of TYMP using whole cell lysate or nuclear extract, resolving the IPs in SDS-PAGE, and then staining the gel with coomassie blue, it was discovered that TYMP associated proteins are more in the nuclei than in the cytoplasm (FIG. 4A). The proteins that were less pulled down by the IgG were analyzed via mass spectrometry. 58 proteins were identified. The accuracy of the mass spectrometry analysis were confirmed by Western blot analysis for two of the identified proteins (FIG. 4B). Among the 58 proteins, FBPA, GAPDH, and PKM2 were identified as being of particular interest as they are key enzymes in the glycolysis pathway, and as TYMP deficiency reduced GAPDH (FIG. 3). These data indicated that TYMP may also affect glycolysis, and thus enhances de novo lipid generation.

Figure 4C:
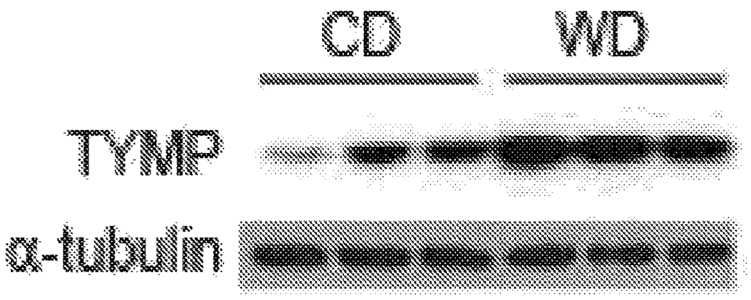
Figure 4D:
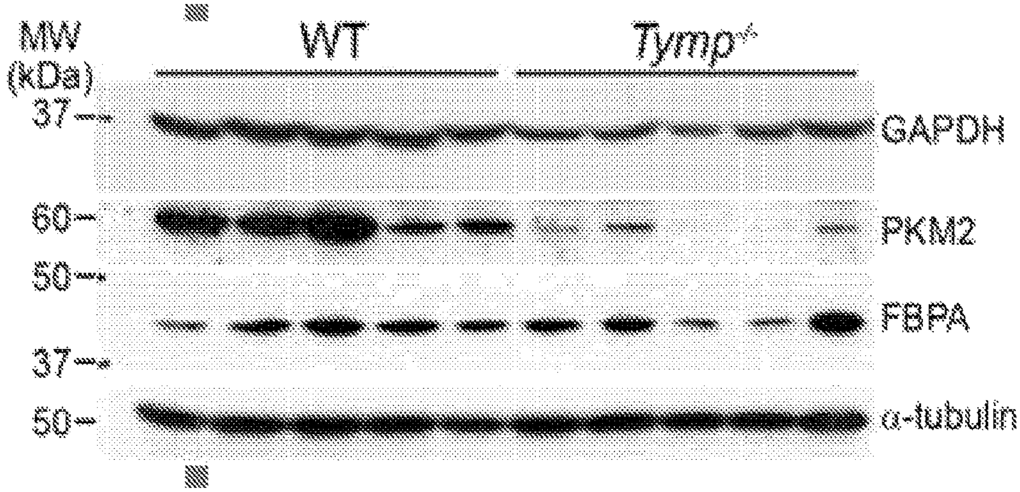
Figure 4E:
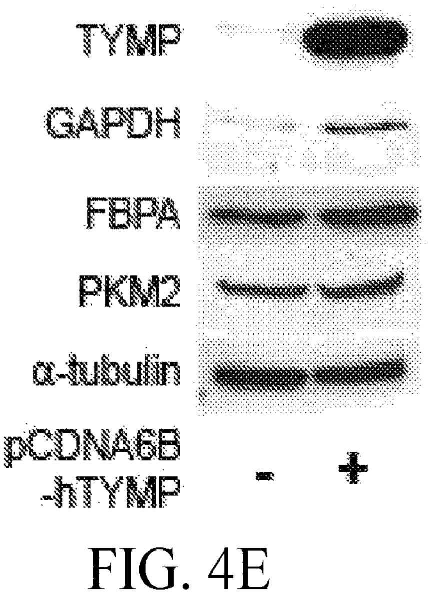

It was also found that WD feeding significantly increased TYMP expression in mouse livers (FIG. 4C). Whether this increase was a complementary response to the chronic elevation of blood glucose and fatty acid levels led by the WD feeding or pathologic was unknown. It was found that TYMP physically forms an association with PKM2 (pyruvate kinase, muscle isoform M2), GAPDH (glyceraldehyde-3-phosphate dehydrogenase), and FBPA (fructose-bisphosphate aldolase, Aldolase A), all of which are enzymes in the glycolysis pathway, and it was further found that TYMP deficiency generally led to a decrease in GAPDH, PKM2, and FBPA (FIG. 4D). By overexpressing TYMP in THLE-3 cells, a primary human liver cell line, it was found that TYMP dramatically increased expression of PKM2, GAPDH, and FBPA (FIG. 4E). These data indicated that TYMP plays a role in regulating expression of enzymes in the glycolytic pathway and may enhance glycolysis.

Example 5—Peritoneal Macrophages do not Express TYMP

Figure 5:
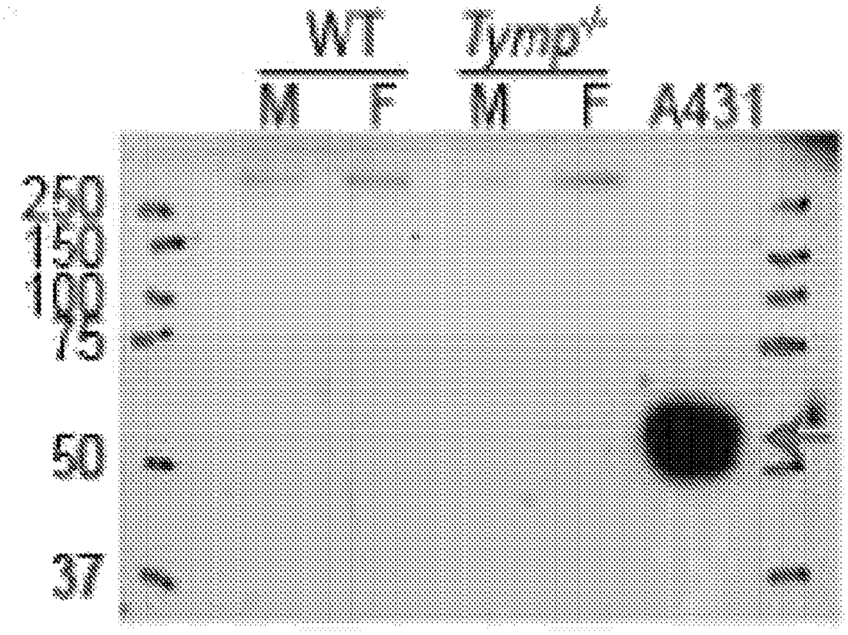
FIG. 5 is an image showing a western blot of TYMP expression in peritoneal macrophages.

While fresh isolated human monocytes express low to undetectable TYMP, TYMP has been reported to be expressed in human atherosclerotic plaques and macrophages, especially tumor-associated macrophages. Macrophages play important roles in all stages of atherosclerosis, and obesity-related inflammation. To clarify if TYMP affects macrophage function, thioglycollate-stimulated peritoneal macrophages were isolated from WT and $Tymp^{-/-}$ mice. By Western blot examination of TYMP expression in these cells and using A431 as a positive control, it was found that peritoneal macrophages do not express TYMP (FIG. 5).

Example 6—TYMP Overexpression Induces Constitutive NF-κB Activation

Figure 6:
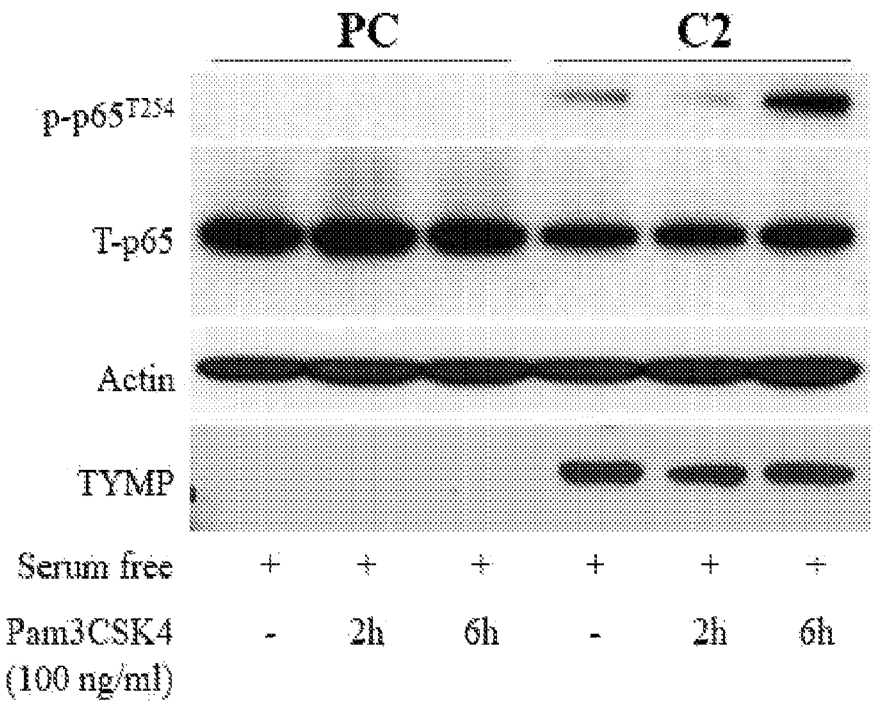
FIG. 6 is an image showing overexpressing TYMP enhances NF-κB and toll-like receptor (TLR) signaling activation in VSMC.

The angiogenic effect of TYMP is mediated by up-regulating the expression of IL-8 and NF-κB as well as their target genes, including fibronectin-1 and IL-6. TLRs recognize pathogen-associated molecular patterns and danger-associated molecular patterns and induce TLR-mediated intracellular signaling cascades activation, especially NF-κB activation, to eliminate the pathogens through the production of proinflammatory cytokines including TNF-α, IL-6, IL-1β, and IL-8. In the previous study, human TYMP gene was transfected into rat VSMC, which does not express TYMP, and a stable TYMP-overexpressing VSMC cell line was established, C2. Empty vector transfected VSMCs, PC, were used as control. By using C2 and PC cells, it was found that TYMP overexpression significantly increased serum-stimulated activation of STAT (signal transducer and activator of transcription) 3, which is known to play a role in inflammation. Scattered studies showed that TLR1 to 9 are expressed by VSMCs or cells in the vessel wall. To understand whether TYMP is involved in TLR-mediated inflammation, C2 and PC cells were synchronized by serum-starvation for 24 hours, and then stimulated with Pam3CSK4, a TLR1/2 signaling agonist, for 2 and 6 hours. Activation of NF-κB was examined by Western blot assay of p65 phosphorylation at T254 (p-p65T254). As shown in FIG. 6, Pam3CSK4 did not induce any NF-κB activation in PC cells. TYMP overexpression per se, however, induced NF-κB p65 phosphorylation even in the serum-free condition, indicating that TYMP plays a role in NF-κB activation. Engagement of TLR1/2 with Pam3CSK4 induced further p65 phosphorylation 6 hours after treatment. These data lead to the hypothesis that TYMP is essential for TLR signaling transduction, and overexpression of TYMP induces a constitutive NF-κB activation. The kinase that phosphorylates p65 at T254 is not yet identified. Phosphorylation of T254 leads to Pin1-dependent prolyl isomerisation of p65, which increases p65 stability, nuclear accumulation, and enhances transcription. These data suggest that TYMP may promote TLR-mediated inflammation through enhancing NF-κB activation.

Example 7—TYMP Deficiency Attenuates WD-Induced Activation of MAPKs

Figure 7:
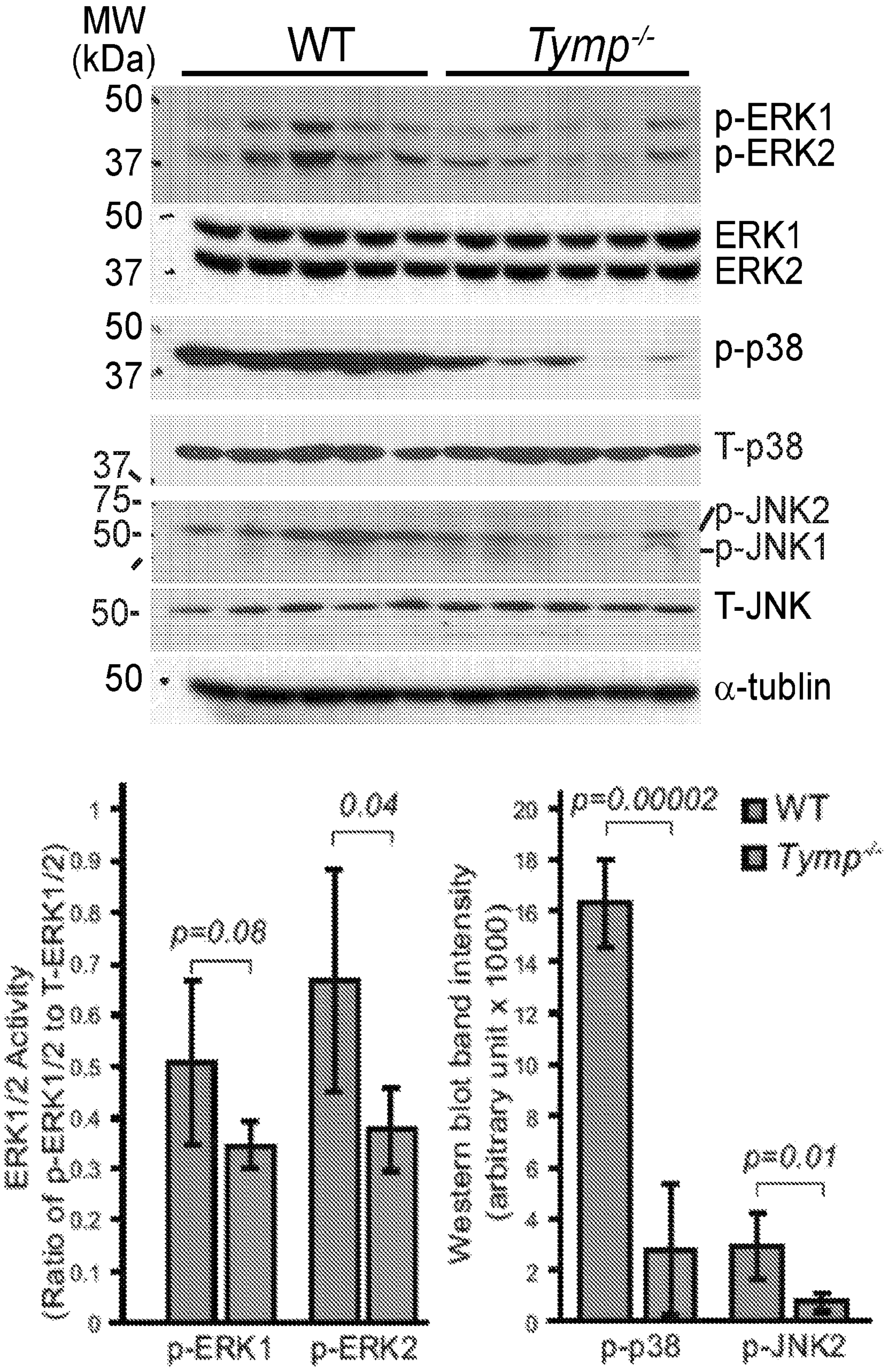
FIG. 7 include images and a graph showing TYMP is essential for WD-induced activation of MAPKs, where liver tissue lysates were used for Western blot assay of active and total ERK1/2, phosphorylated p38 and JNK1/2, where actin was blotted as loading control, where band intensity was analyzed with Image J, where ERK1/2 activation were presented as ratio of the phosphorylated to the total forms, and where raw band intensity data were used for p-p38 and p-JNK comparison.

The c-Jun-N-terminal-kinase (JNK) plays a central role in the cell stress response, obesity, and insulin resistance, and emerging evidences indicate that JNK1 and JNK2 isoforms promote the development of obesity and insulin resistance, and JNK3 protects from excessive adiposity. To test the pathogenesis of TYMP-mediated development of obesity the activation of MAPKs including JNK, ERK and p38 were first examined in the liver of mice fed with WD for 8 weeks. As shown in FIG. 7, TYMP deficiency dramatically reduced phosphorylated ERK2, p38, and JNK2. These MAPKs phosphorylation data indicated that WD-fed mice have increased stress, which is TYMP-dependent.

Example 8—TYMP Deficiency Leads to a Better Glucose Tolerance

Figure 8A:
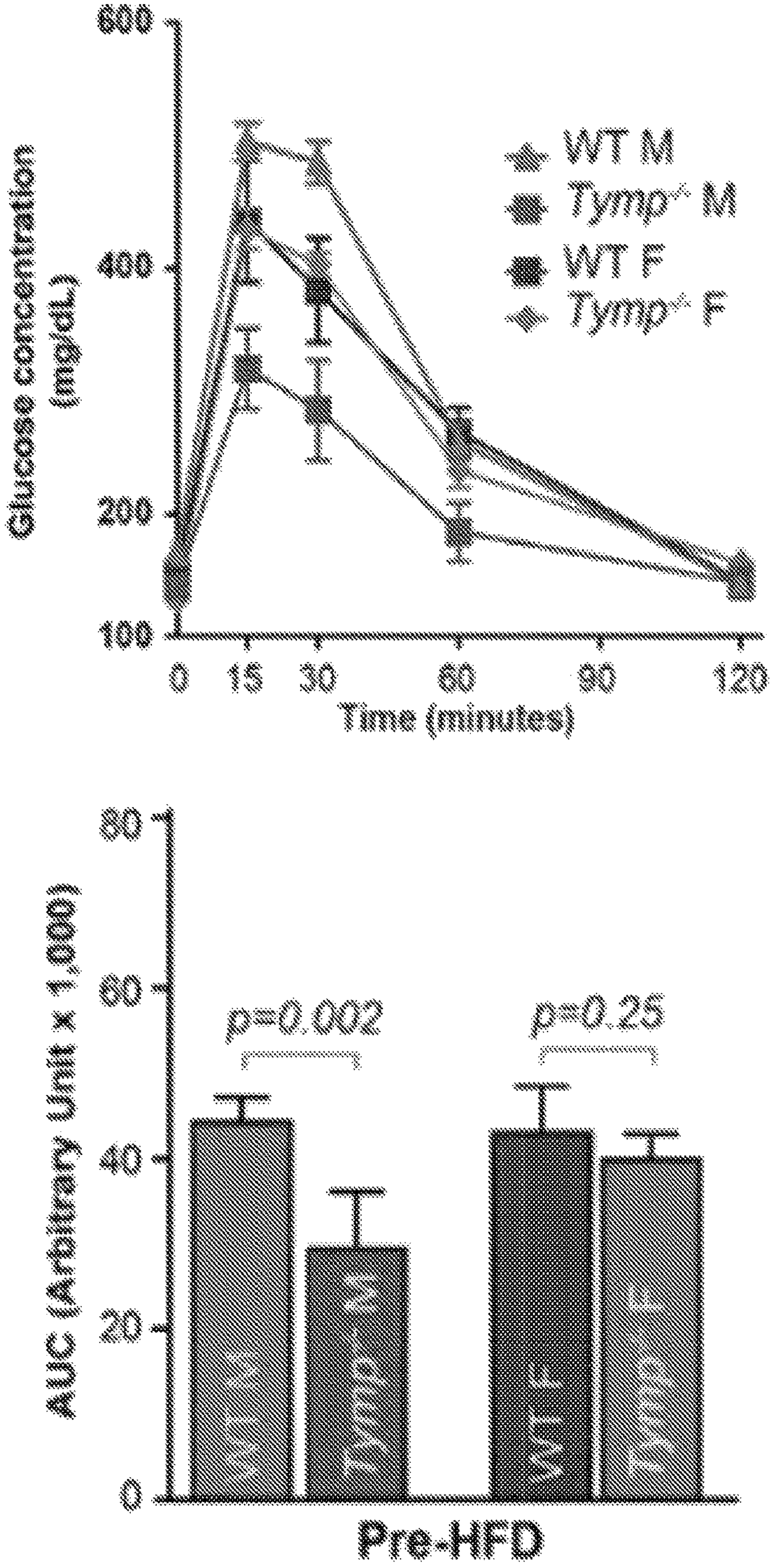
FIGS. 8A-8B include graphs showing TYMP deficiency increased tolerance of mice to glucose loading, where intraperitoneal glucose tolerance test (IPGTT) were performed on WT and $Tymp^{-/-}$ mice before (FIG. 8A) and 16-weeks after (FIG. 8B) being on high fat diet (HFD, D12492, 60% calories from fat, purchased from Research Diets), where bar graphs show statistical analysis of areas under curve (AUC), and where five to seven mice were used in each group (M=male, F=female).
Figure 8B:
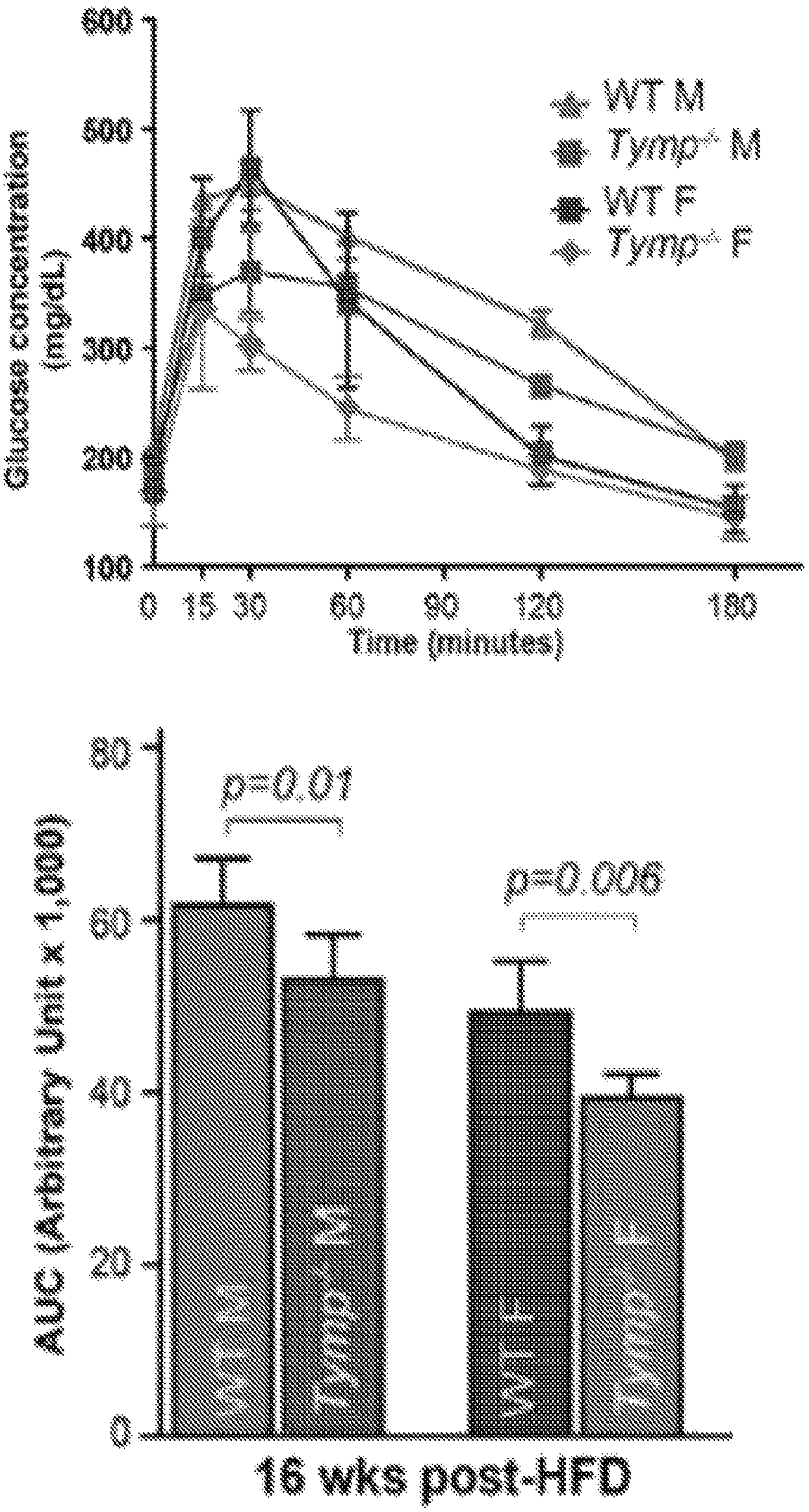

TYMP may participate in obesity-associated systemic inflammation, which plays important roles in insulin resistance. To test the hypothesis that TYMP plays a role in insulin resistance, an intraperitoneal glucose tolerance test (IPGTT) was performed on mice fed with HFD, which were used for studying the role of TYMP on T2DM-associated thrombotic diathesis. Eight weeks old WT and $Tymp^{-/-}$ mice were fasted overnight, and then FBG levels were measured. The mice were then given an intraperitoneal injection of glucose solution at a concentration of 2 mg/g body weight, and blood glucose levels were measured at the scheduled time points using a Roche AccuCheck Active. The mice were then fed with HFD for 16 weeks, and IPGTT data were collected again with a glucose loading dose at 1 mg/g body weight before they were sacrificed. As shown in FIGS. 8A-8B, there was no difference in the levels of FBG between WT and $Tymp^{-/-}$ mice in both genders. Whereas TYMP deficiency did not affect glucose tolerance in the female mice, TYMP null male mice had better glucose tolerance than WT animals at 8 weeks old (still on chow diet). HFD-feeding for 16 weeks dramatically increased FBG in both male and female mice from both strains when compared with their FBG levels before on HFD. There was no difference in FBG between WT and $Tymp^{-/-}$ mice in both gender at 16 weeks after HFD. Although the difference in male mice became smaller than before HFD-feeding, TYMP deficiency still dramatically improved glucose tolerance in both genders.

Figure 9:
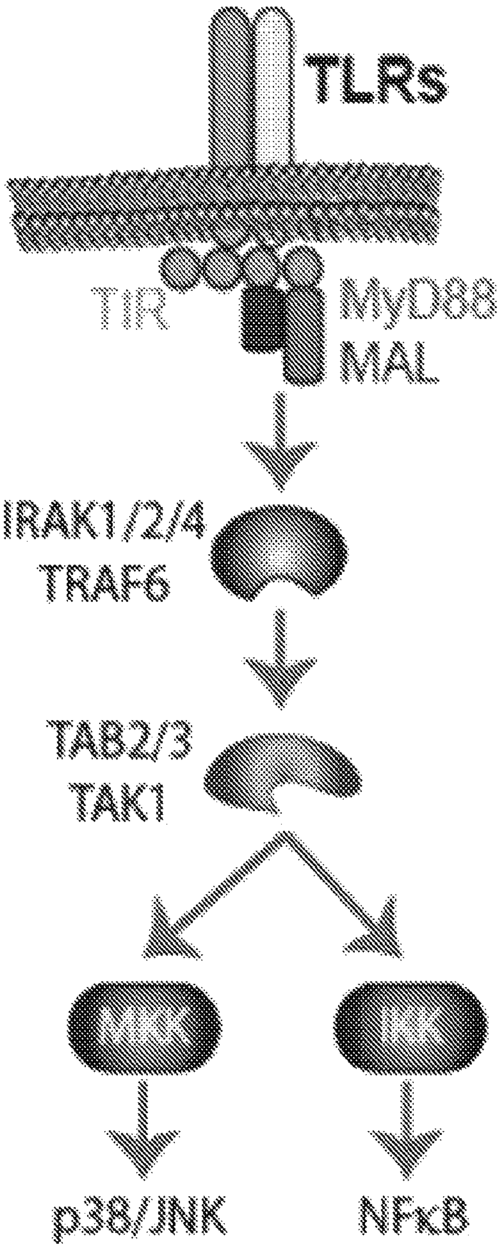
FIG. 9 is a schematic diagram depicting TLR signaling.
Figure 10:
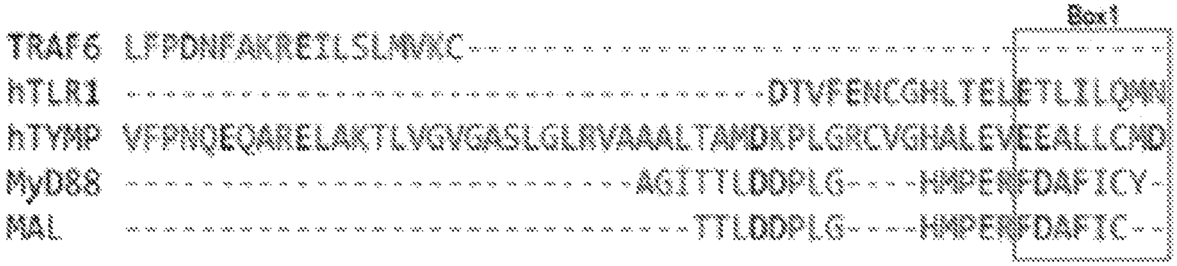
FIG. 10 is a schematic diagram showing alignment of TYMP and TLR-pathway associated proteins.

Each TLR family member recognizes a particular pathogen-specific molecular signature, the various TLRs share a conserved intracellular signaling domain (FIG. 9). Since TYMP is an intracellular protein and it affects both NF-κB and MAPKs activation (FIGS. 6-7), it must present upstream of MKK (MAP kinase kinase) and IKK (inhibitor of NF-κB kinase), which activates p38/JNK and NF-κB, respectively. Namely, TYMP must participate in MyD88 (myeloid differentiation primary-response protein 88) and Mal (MyD88 adaptor-like protein), IRAK (IL-1 receptor-associated kinases) 1/2/4 and TRAF6 (Tumor necrosis factor receptor associated factor 6), or TAK1 (Transforming growth factor β-activated protein kinase 1) and TAB2/3 (TAK1-binding protein 2/3) complex, and through enhancing activity of these complexes to promote activation of MAPKs and NF-κB. TYMP overexpression induced constitutive p65T254 activation, which is independent of Pam3CSK4, the TLR1/2 agonist.

Figure 11A:
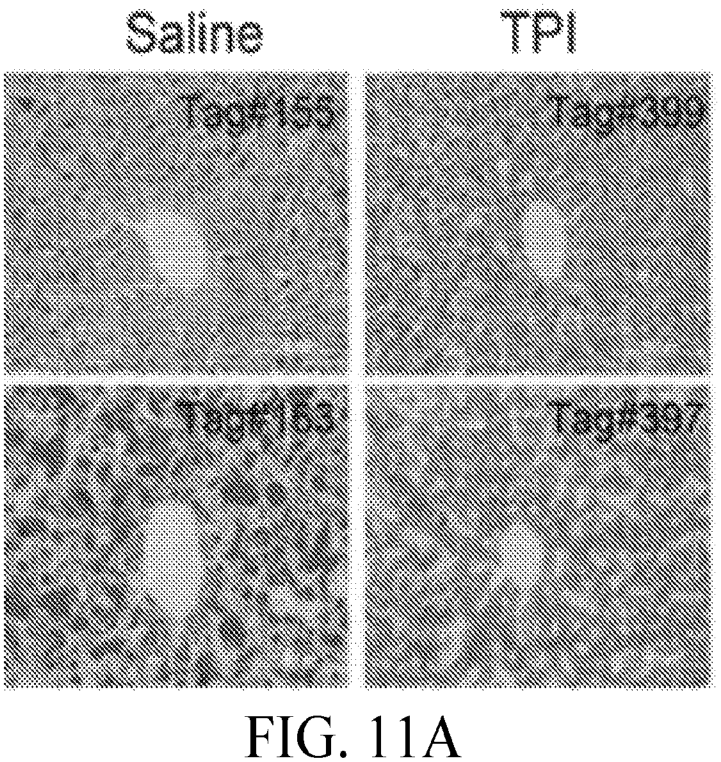
FIGS. 11A-11E are graphs showing that inhibition of TYMP in $Apoe^{-/-}$ mice attenuates liver fat accumulation and atherosclerotic lesion formation, where 6 male and 6 female $Apoe^{-/-}$ mice were randomly divided into two groups with equal number, where one group received saline solution containing tipiracil (TPI) in a dose of 60 μg/Kg/day and another group received saline only for 4 weeks, where liver and aortic root sections as well as aortic tree were stained with Oil Red O and fat accumulation in the liver (FIG. 11A), and plaque formation in the aortic root (FIGS. 11B-11C) as well as on face lesion analysis in the aortic tree (FIGS. 11D-11E) were performed, and where □ indicates female and ○ indicates male animals.
Figure 11B:
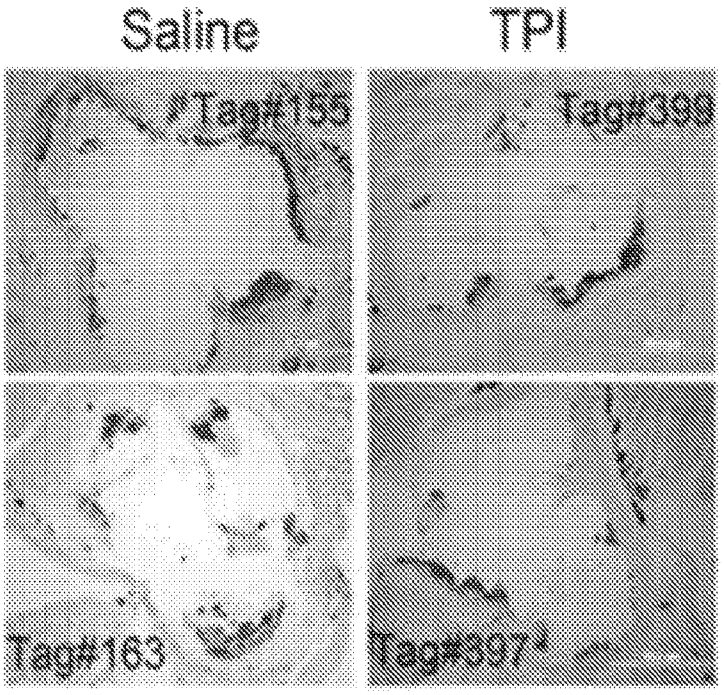
Figure 11C:
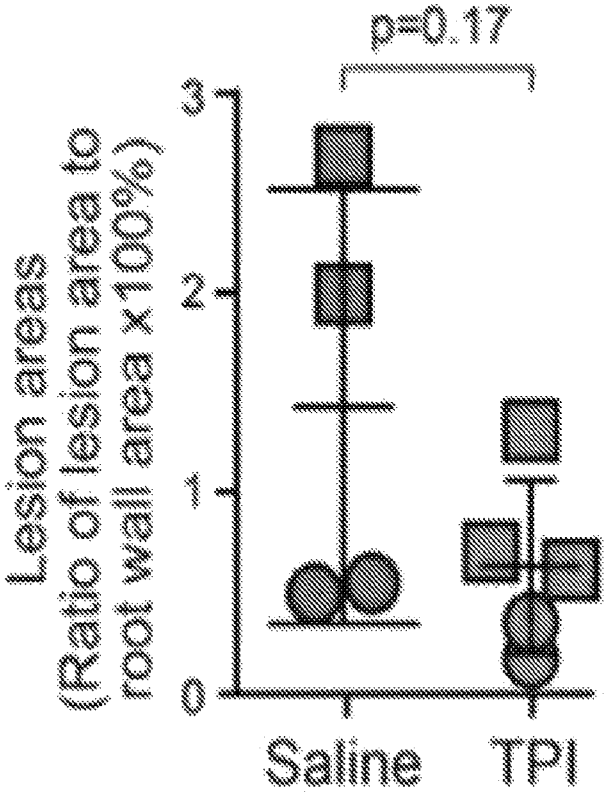
Figure 11D:
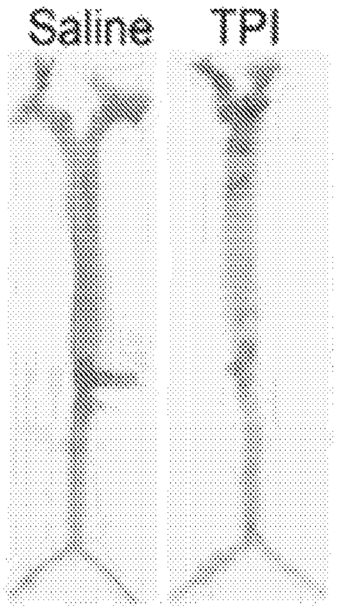
Figure 11E:
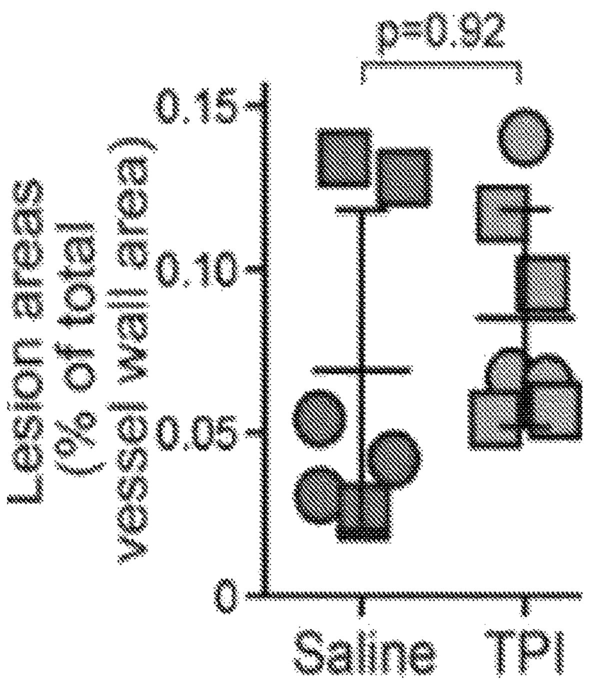

Example 9—Treating $Apoe^{-/-}$ Mice on WD with TPI Attenuates Liver Fat Accumulation and Atherosclerotic Lesions As mentioned above, TYMP enhances platelet activation in vitro and promotes thrombosis in vivo, making TYMP a potential target for antithrombotic therapy. While VSMCs do not express TYMP, as mentioned above, overexpression of TYMP in VSMCs or treatment of VSMCs with TYMP protein inhibits cell proliferation. To test the potential side effect that inhibition of TYMP leads to development of arterial stenosis due to enhancing VSMCs proliferation, 4 months old $Apoe^{-/-}$ mice were fed with WD and at same time, mice were gavage fed with tipiracil (TPI) (60 μg/Kg/day) for 4 weeks. Age-matched $Apoe^{-/-}$ mice on WD fed with saline were used as controls. As shown in FIGS. 11A-11E, TPI attenuated lipid accumulation in livers (FIG. 11A) and atherosclerotic plaque areas formation in aortic root (FIGS. 11B-11C). However, en face analysis of lesion area in the aortic tree was similar in the two groups (FIGS. 11D-11E). Since mouse macrophage do not express TYMP (FIG. 5), these data indicated that TYMP in other cellular players, or its systemic function affects lipid metabolism and atherogenesis.

Figure 12A:
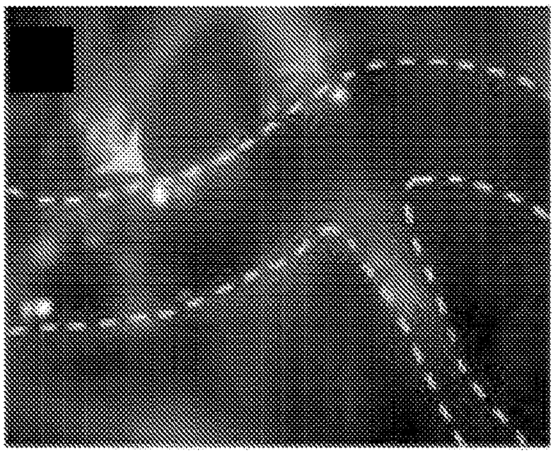
FIGS. 12A-12D are images showing intravital microscopy-based leukocyte adhesion and rolling assay (FIGS. 12A-12B), and platelet/leukocyte adhesion assay (FIGS. 12C-12D), where mice received intra-scrotum injection of Pam3CSK4 (2 ng) and 3 hours later Rhodamine 6G were injected into the mouse via jugular vein to label cells and cell adhesion and rolling were assessed, where the arrows in FIG. 12A and FIG. 12B indicate the initial sites of the two cells, where the arrow heads in FIG. 12B indicate positions 3 seconds after rolling, where the red arrows in FIG. 12B indicate the distance of these two cells rolled, and where, in FIGS. 12C-12D, platelets and leukocytes were labeled with Cell-Tracker Red and Green, respectively, mixed together and then injected into mouse via jugular vein, and the mice were then treated with 500 ng TNF-α by intra-scrotum injection, and platelet-leukocytes interaction and immunothrombi were assessed 3 hours later, where the arrow in FIG. 12C indicates the initial formation of an immunothrombi, and where
Figure 12B:
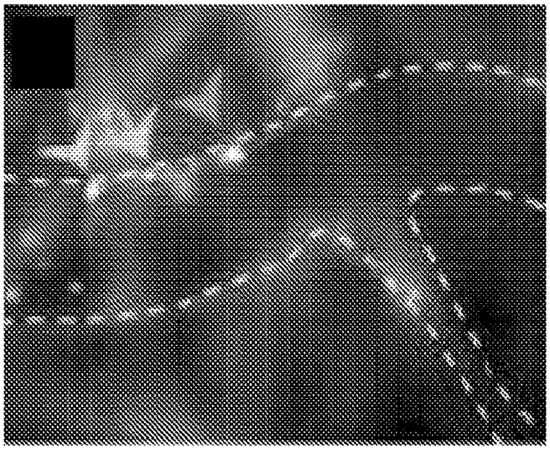
Figure 12C:
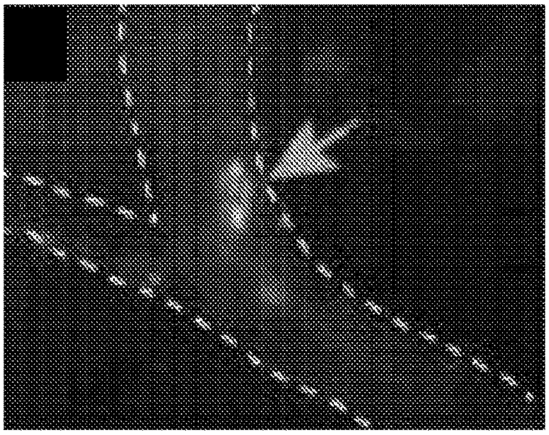
Figure 12D:
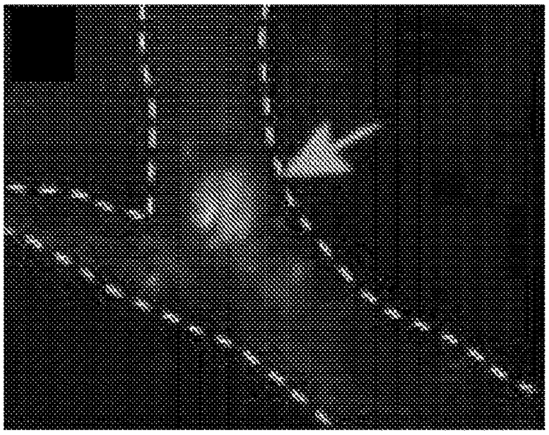

Example 10—Leukocyte Adhesion and Rolling Assay as Well as Platelet/Neutrophil Adhesion Assay At sites of infection, vascular injury, or regional proinflammatory or pathogen-derived stimuli, the luminal vascular endothelial surface can become attractive for leukocytes and platelets, which has been known playing important roles in the development of inflammation and atherosclerosis. Leukocyte adhesion and rolling on the vessel wall can be visualized and quantified by combination of intravital video microscopy with fluorescent-labeled cells in carotid artery, or in cremaster microvascular system (FIGS. 12A-12B), among others. By using this technique, platelet/leukocyte interaction can also be measured by labeling them with different fluorescent dyes (FIGS. 12C-12D). This technique measures the function of platelet, leukocyte, and endothelial cells under various diseased conditions.

Example 11—Effect of Thymidine Phosphorylase Inhibition on Obesity

Figure 13:
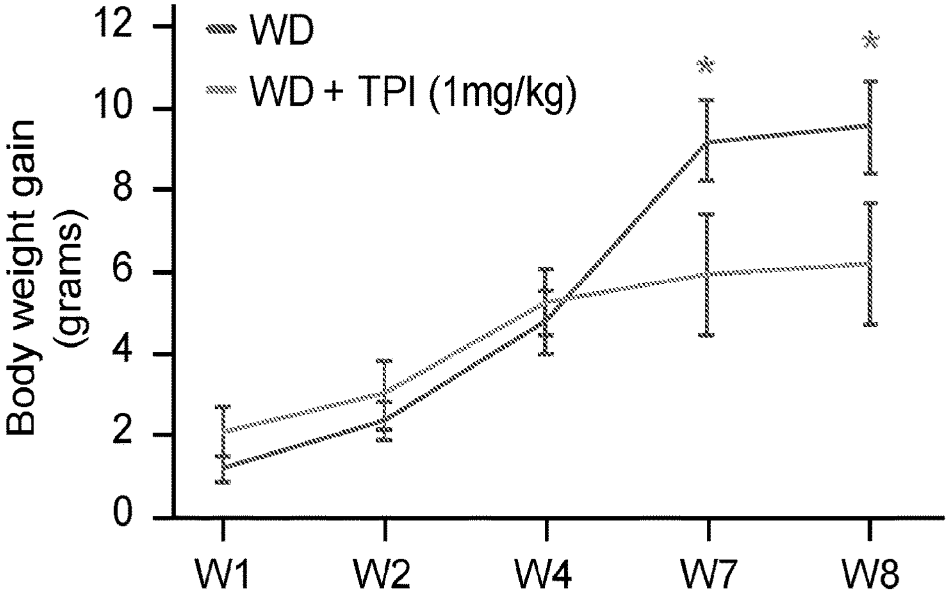
FIG. 13 is a graphs showing tipiracil (TPI) decreases diet induced weight gain.

To determine if inhibition of TYMP could attenuate or inhibit obesity in vivo, C57Bl6 wild type mice were fed with a western diet (TD.88137, 42% calories from fat), started from 6 to 8 weight old, to facilitate their weight gain. At same time, the mice were gavage-fed with tipiracil hydrochloride (TPI, purchased from APExBIO) in 300 μl saline with a dose at 1 mg/kg/day. Mice received the same volume of saline feeding as a control. Body weight gain was monitored weekly, and data were presented as mean of the accumulated weight gain from each mice at each week. N=3 in the saline-feeding group, and 2 in the TPI-feeding group. As shown in FIG. 13, upon the analysis of the results from the experiments, it was observed that TPI, a potent TYMP inhibitor (IC50=34 nM) that is an ancillary component of an anti-cancer drug Lonsurf and is approved by the FDA for clinical use, reduced WD-induced body weight gain.

Example 12-16 Week HFD Induced Obesity

Figure 14:
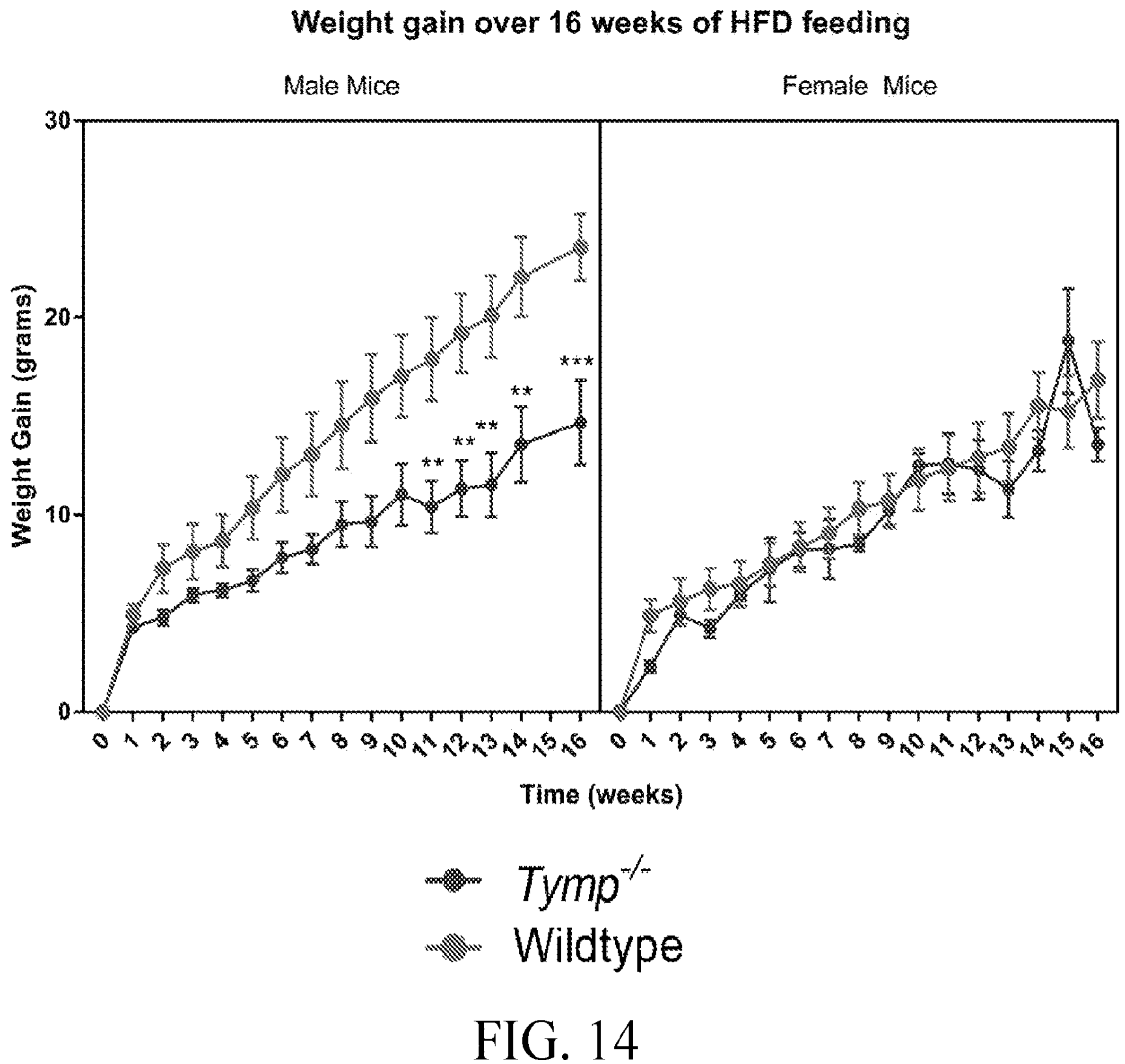
FIG. 14 includes graphs showing body weight gain in wild type (WT) and Tymp (−/−) mice over 16 weeks of high fat diet (HFD, D12492, 60% calories from fat, purchased from Research Diets) feeding.

To further examine the effects of TYMP on weight gain, mice, starting at 8 weeks old, were fed with a high fat diet (HFD, D12492, research diet) and their weight was measured weekly. Body weight gain was then measured in wild type (WT) and $Tymp^{-/-}$ male and female mice. As shown in FIG. 14, TYMP deficiency allowed for decreased weight gain in male but not female mice (line graph shows total weight gained, statistical analysis with 2 way ANOVA and error bars are mean±SEM), further confirming the initial findings shown above in FIG. 2.

Example 13—Targeting Thymidine Phosphorylase with Tipiracil Hydrochloride is a Safe and Effective Antithrombotic Therapy It has been demonstrated that TYMP is a potential signaling protein and it may transfer cell signaling through the binding of its proline-rich N-terminus to the SH3 domain in its partner proteins. TYMP deficiency dramatically inhibited platelet response to the conventional agonists, such as collagen, ADP, and thrombin. Inhibition of TYMP activity with a novel TYMP inhibitor, KIN59, dramatically inhibited platelet activation in vitro and thrombosis in vivo. These data suggest that TYMP is a targetable intracellular protein in platelets and its inhibition is antithrombotic. The potent and specific TYMP inhibitor, tipiracil hydrochloride (TPI), is an auxiliary component of a novel anticancer drug, Lonsurf. Lonsurf was recently approved by the FDA for clinical use, suggesting that TPI could be repositioned as a novel antiplatelet and anti-thrombotic drug. In the study described below, the role of TPI on platelet activation and thrombosis was examined using in vitro and in vivo studies and evidence is provided showing that TPI-mediated TYMP inhibition is a safe and effective antithrombotic therapy. TPI is suitable as both a primary and secondary prevention for patients with high risk of thrombotic cardiovascular diseases.

Methods and Materials.

Experiment animals. $Tymp^{-/-}$ mouse strain was generated by Dr. Hirano's laboratory as mentioned before. Wild type C57BL/6 mice (WT) were purchased from Jackson Laboratory (Bar Harbor, ME). All procedures and manipulations of animals have been approved by the Institutional Animal Care and Use Committee of Marshall University (IACUC #: 1033528).

Murine carotid artery thrombosis model and tail bleeding assay. Detailed ferric chloride ($FeCl_3$) induced carotid artery thrombosis model has been described before. Vessel injury was induced by 7.5% $FeCl_3$ solution to the carotid artery for 1 minute. Thrombi formation was observed in real-time using an intravital microscope. The endpoints were set as follows: 1) blood flow has ceased for >30 seconds; or 2) occlusion is not seen after 30 minutes of $FeCl_3$ injury. In this case, 30 minutes was assigned to that mouse for the statistical analysis. In some experiments, a jugular vein catheter prepared with P-10 tubing was placed for drug administration after 5 minutes of thrombus initiation. Thrombus formation was continually monitored using the endpoints mentioned above. Tail bleeding assay was either conducted on mice immediately after the thrombosis study or on mice that were not used for the in vivo thrombosis study.

Mouse platelet aggregation assay. Mice were anesthetized with ketamine/xylazine (100/10 mg/kg) and whole blood were drawn through inferior vena cava (IVC) puncture using 0.109 M sodium citrate as an anticoagulant. Platelet-rich plasma (PRP) was used for platelet aggregation assay. In some experiments, platelets were pretreated with different concentrations of TPI for 2 min (or indicated times) before adding $CaCl/MgCl_2$ at a final concentration of 1 mM and agonists as indicated in the Results. Same volume of vehicle (DMSO or saline)-treated platelets was used as controls.

Cellix flow chamber-based platelet adhesion and aggregation assay. Cellix flow chambers were coated with collagen 10 μg/mL in PBS. Whole blood was drawn from mouse IVC using 0.109 M sodium citrate as an anticoagulant, stained with Rhodamine 6G, and then used for the flow chamber mediated adhesion and aggregation assay. Some of the whole blood was treated with or without TPI before it was perfused into the chamber.

Comparison of the therapeutic effect of TPI to aspirin and clopidogrel. 8 to 10 week-old male WT mice were gavage fed with either TPI, aspirin, or clopidogrel once daily for one week, then subsequently used in an in vivo thrombosis study. Tail bleeding assay was conducted on these mice immediately after the thrombosis study.

Examination of the effect of TYMP inhibition on thrombosis under hyperlipidemia. WT mice were fed a western diet (WD, TD.88137) for a total of 4 weeks. For a separate group of mice, the diet was changed to a customized diet (TD.190501), which has the same component as TD.88137 with the addition of 10.7 mg/kg TPI, for the last 7 days of feeding. Mice fed with TD.190501 received approximately 1 mg/kg/day of TPI. These mice were then subjected to the thrombosis study using the 7.5% $FeCl_3$ induced thrombosis model.

Evaluation of platelet signaling activation. Platelets in PRP were stimulated with 2.5 μM ADP for 0, 1, 3, and 5 minutes, then lysed with radioimmunoprecipitation assay (RIPA) buffer containing proteinase/phosphatase inhibitor cocktail. The lysates were subsequently used for AKT activation immunoblotting assays. ADP-stimulated p-selectin expression was analyzed by flow cytometry.

Generation of fusion proteins to determine that TYMP binds to LYN through the SH3 binding domain. Human SH3 domain nucleotides (hLynSH3, amino acids 63-123) were amplified by PCR and cloned into a mammalian expression vector pEBG (Addgene, plasmid #22227) with an N-terminal glutathione S-transferase (GST) affinity tag (pEBG-GST-hLynSH3). A pCDNA6B/his-hTYMP plasmid vector was previously constructed. pEBG-GST-hLynSH3 and pCDNA6B/his-hTYMP plasmids were co-transfected into COS-7 cells, lysed in a Pierce™ IP Lysis Buffer (ThermoFisher Scientific), and used for GST pull down assay. Eluates were used for Western blot assay to confirm the presence of TYMP.

pEGFP-N1-human Lyn-GFP and pCDNA6B/his-hTYMP plasmids were also co-transfected into the COS-7 cells. TYMP was pulled down using immobilized Ni-NTA on magnetic sepharose beads (GE Healthcare Life Sciences) for His-tagged protein purification. His-hTYMP eluates were used for western blot assay for Lyn.

Statistics. Data are expressed as mean f SEM. Results were analyzed by 2-tailed Student's t test or 1-way ANOVA with Bonferroni post-hoc test for multiple comparisons using Graphpad Prism (version 8.3.1). $P<0.05$ was considered statistically significant.

Results

Figure 15A:
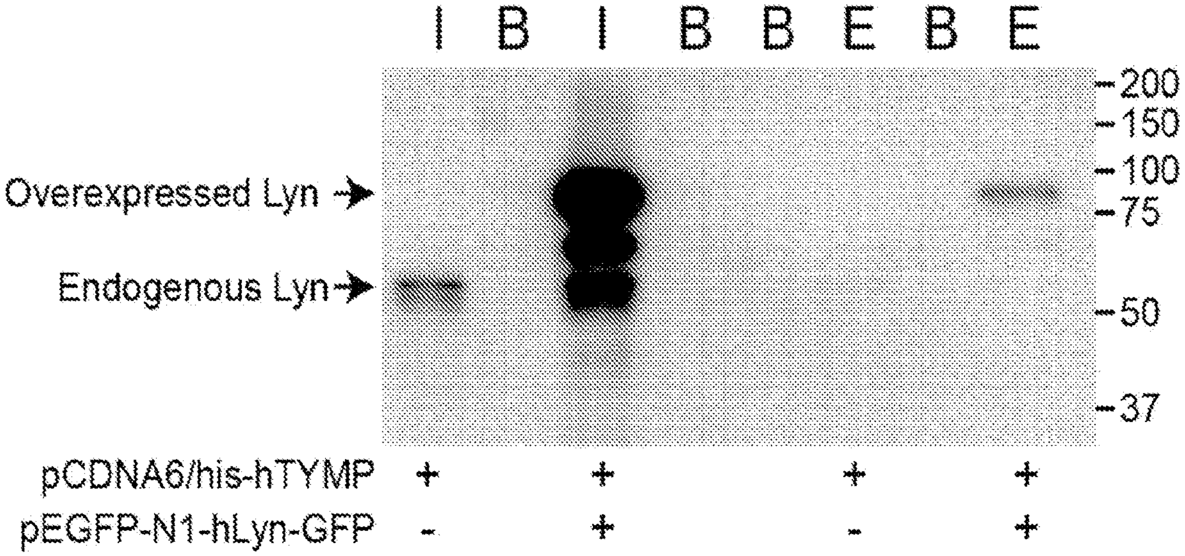
FIGS. 15A-15B include images showing TYMP binds to its partners through their SH3-domain, where (FIG. 15A) pCDNA6/his-hTYMP plasmid vector, either alone or combined with pEGFP-N1-hLyn-GFP vector, was transfected into Cos-7 cells, and His-Tagged TYMP was pulled down using His Mag Sepharose Ni beads with inputs and elutes blotted using anti-Lyn antibody, and where (FIG. 15B) pCDNA6/his-hTYMP and pEBG-GST-SH3(hLyn) were co-transfected into Cos-7 cells and the lysate was used for GST pull-down assay and elute was used for blotting human TYMP (in both panels, I: input; B: blank, E: elute. Blots represents 2-3 repeats).
Figure 15B:
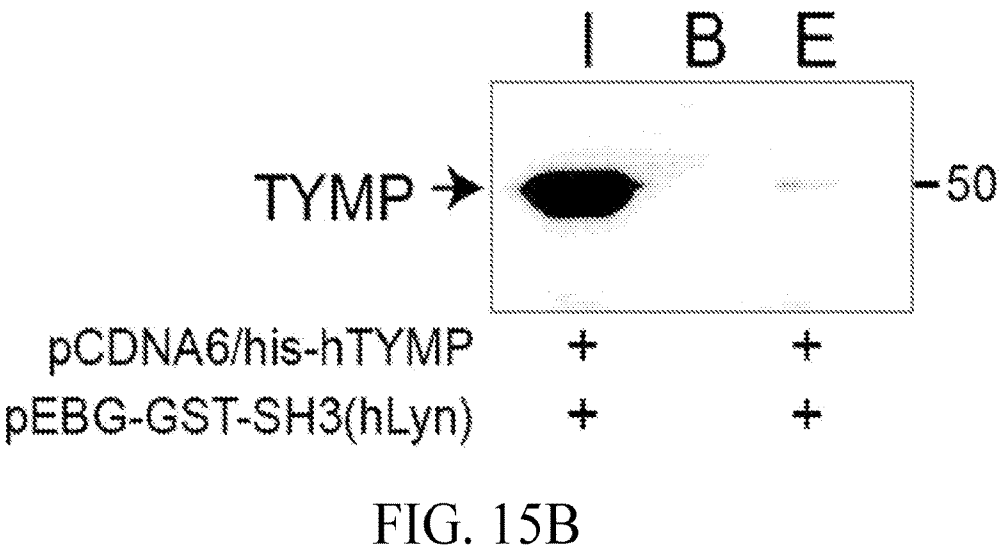

TPI treatment disrupted the associated of TYMP and Lyn. A previous study demonstrated that TYMP is a novel signaling protein and it binds to the SH3 domain-containing proteins, probably through its proline rich N-terminus. This finding was confirmed by overexpressing full length human TYMP and Lyn in Cos-7 cells. By pulling down His-Tagged TYMP using the lysates prepared from the co-transfected cells, both endogenous and overexpressed Lyn was found to be present in the elute (FIG. 15A), which corroborates the previous finding using human and mouse platelet lysates. To show the direct evidence, a GST-SH3 fusion protein was further generated and its binding to human TYMP was examined by GST pull-down assay. As shown in FIG. 15B, pulling down GST-SH3 also pulled down human TYMP. These data showed the direct evidence that TYMP binds to its partner proteins through their SH3 domain.

Figure 16A:
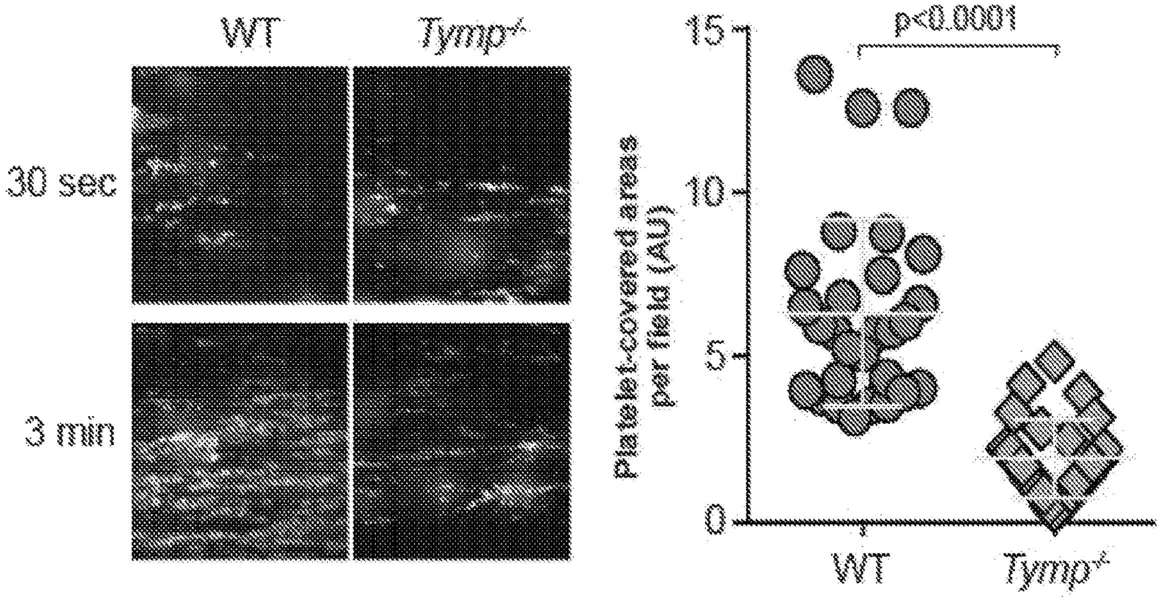
FIGS. 16A-16B include images and graphs showing Cellix Vena8 Fluoro+ chamber-based platelet aggregation assay, where the flow chambers were coated with 10 μg/ml collagen overnight, where (FIG. 16A) whole blood drawn from WT and $Tymp^{-/-}$ mice were perfused into the chamber in a flow shear 65 $dyn/cm^2$, where (FIG. 16B) WT whole blood treated with 50 μM TPI in saline or saline alone were perfused into the chamber at a shear 65 $dyn/cm^2$, and where the graphs show areas covered by platelets at 3 minutes after perfusion.
Figure 16B:
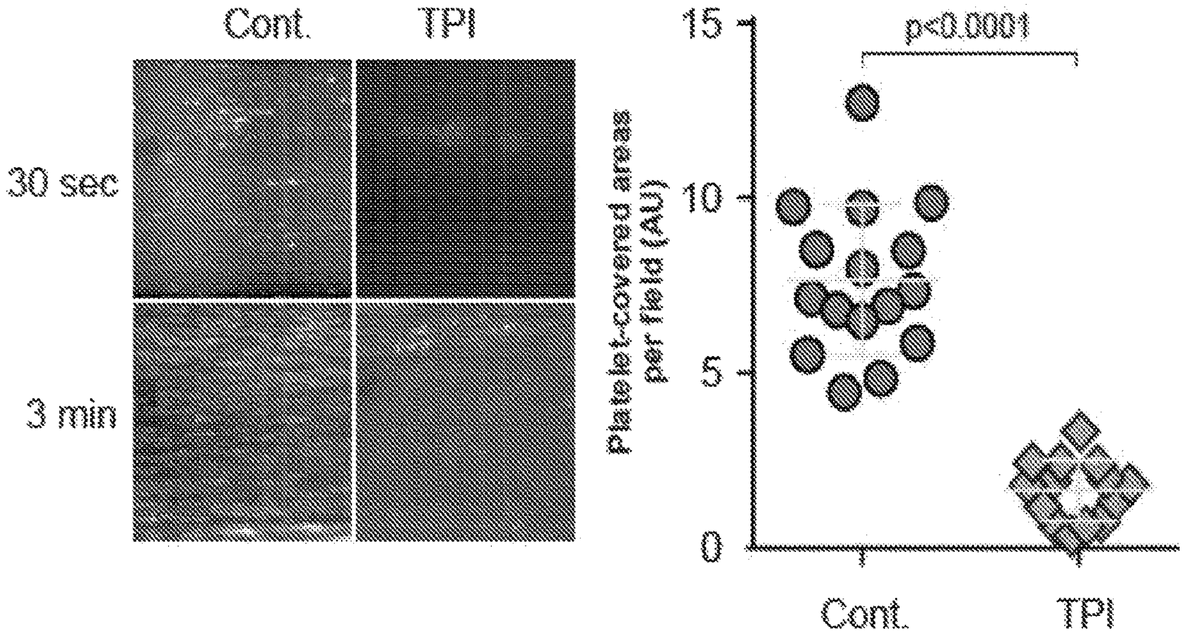

TYMP-deficiency attenuates platelet aggregation to collagen-coated surfaces. Adhesion to the injury site is an essential function for platelets and is generally viewed as the first step of aggregation, during which specific membrane receptors on the platelet surface binds to cellular and constituents of the extracellular matrix and the vessel wall. The initial functional receptors primarily include platelet GPIb-XI-V and GPVI. By using a Cellix Vena8 Fluoro+ chamber system, it was found that TYMP-deficiency did not affect platelet binding to the type I collagen-coated surface (FIG. 16A). However, TYMP-deficiency dramatically decreased platelet aggregation at the end of the three-minute observation (FIG. 16A). Inhibition of TYMP with 50 μM TPI also significantly reduced platelet aggregation to the collagen-coated surface (FIG. 16B). These data indicated that TYMP plays a functional role in GPVI signaling-mediated platelet activation and, thus, aggregation; however, TYMP deficiency or inhibition does not affect platelet adhesion to collagen.

Figure 17A:
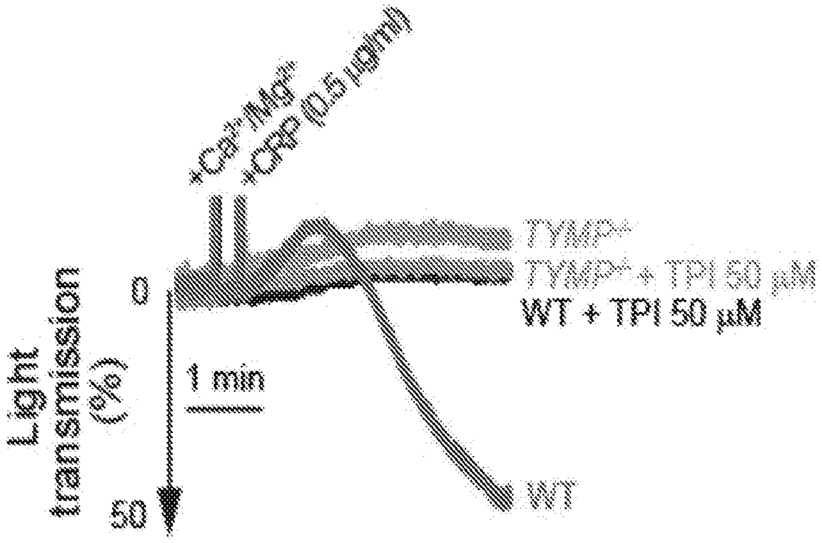
FIGS. 17A-17G include graphs and images showing inhibition of TYMP in vitro inhibits platelet activation, where (FIG. 17A) WT and $Tymp^{-/-}$ platelets in PRP were treated with 50 μM TPI for 2 minutes and then CRP-induced platelet aggregation was assessed, where (FIGS. 17B-17C) WT platelets in PRP were treated with different concentration of TPI for 2 minutes and then collagen (1 μg/ml) induced platelet activation was assessed, where (FIG. 17D) WT and $Tymp^{-/-}$ platelets in PRP were treated with 50 μM TPI for 2 minutes and then 2.5 μM ADP-induced platelet aggregation was assessed, where (FIG. 17E) WT and $Tymp^{-/-}$ platelets in PRP were treated with 2.5 μM ADP for the indicated times and then AKT activation were evaluated (blot represents two repeats), where (FIG. 17F) WT platelets in PRP pooled from 10 mice were divided into 8 parts with four parts treated with 50 μM TPI and another 4 parts treated with saline as controls before they were treated with 2.5 μM ADP for the indicated times, and with platelet lysates used for assessing AKT phosphorylation, and where (FIG. 17G) WT platelet in PRP were divided into 8 groups, treated with saline or 50 μM TPI, and then treated with 2.5 μM ADP for the indicated times, with platelet surface p-selectin expression analyzed by flow cytometry and data shown as ratio of control (0 minute) (N=3).
Figure 17B:
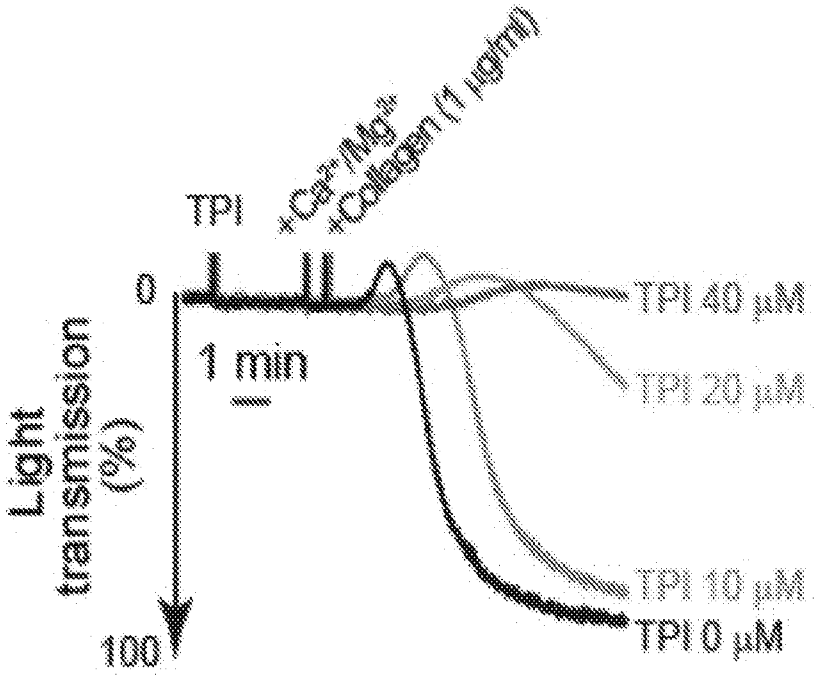
Figure 17C:
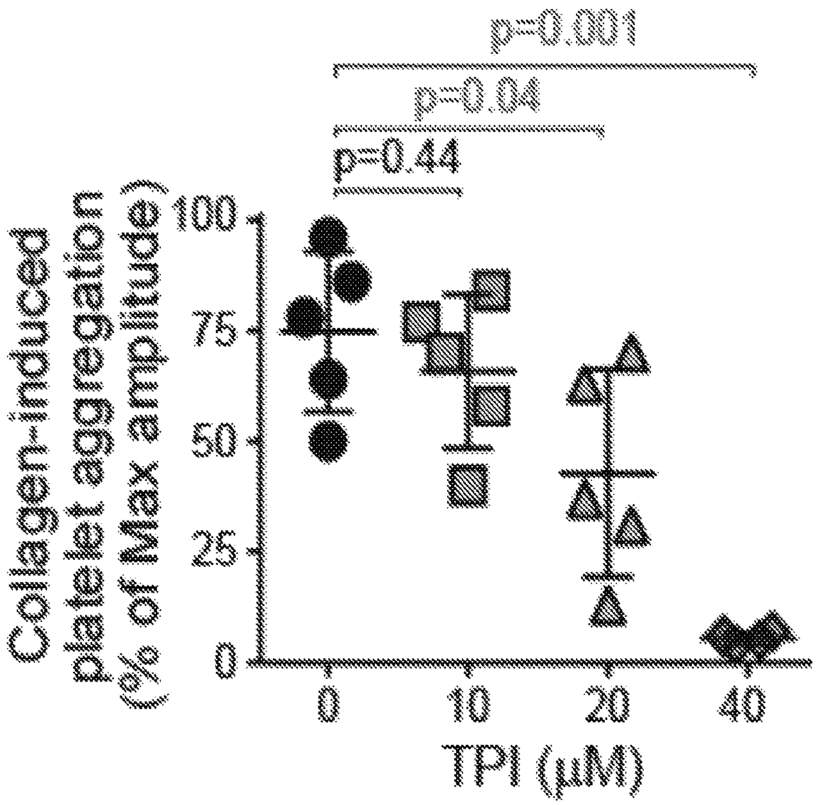
Figure 17D:
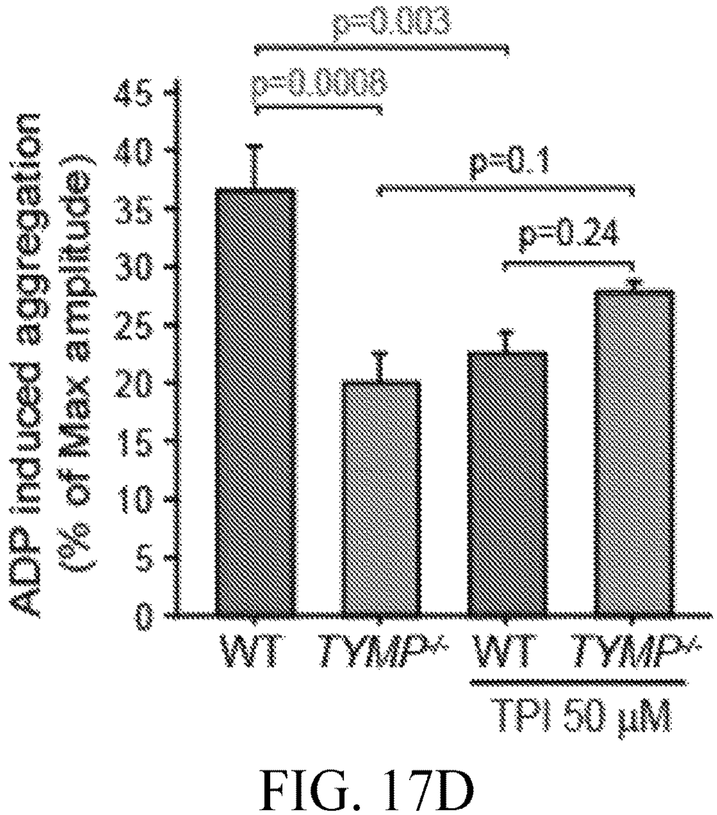
Figure 17E:
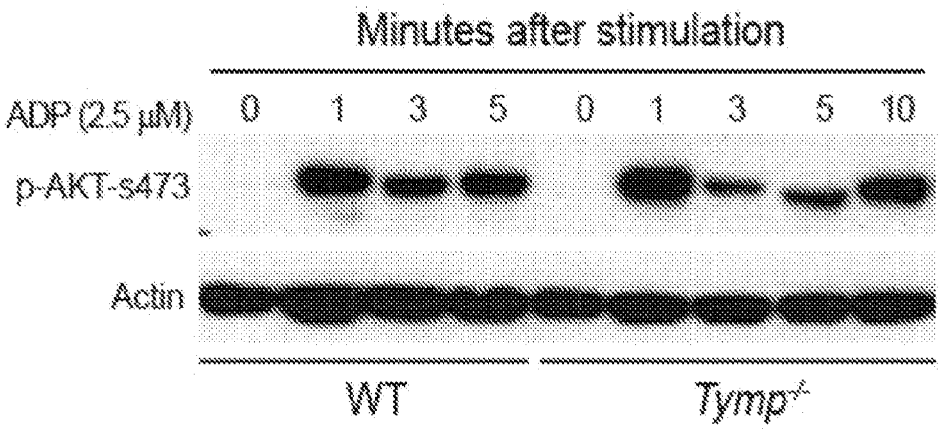
Figure 17F:
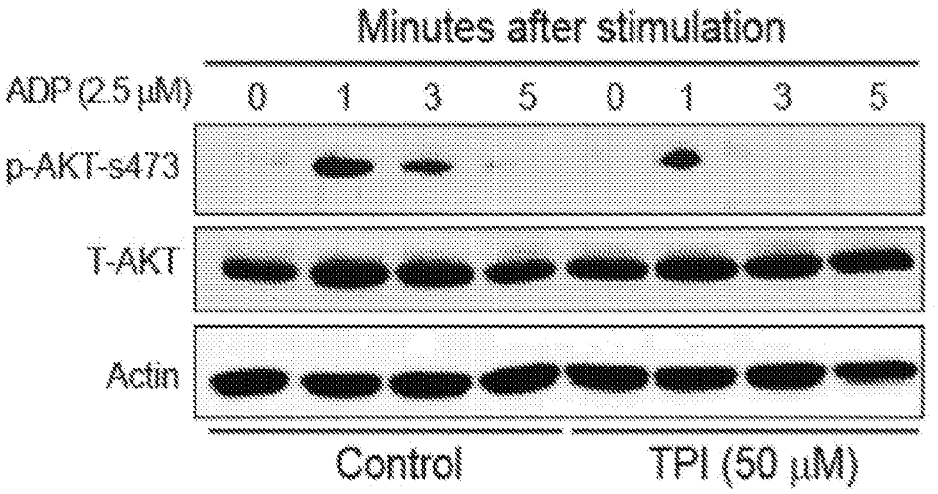
Figure 17G:
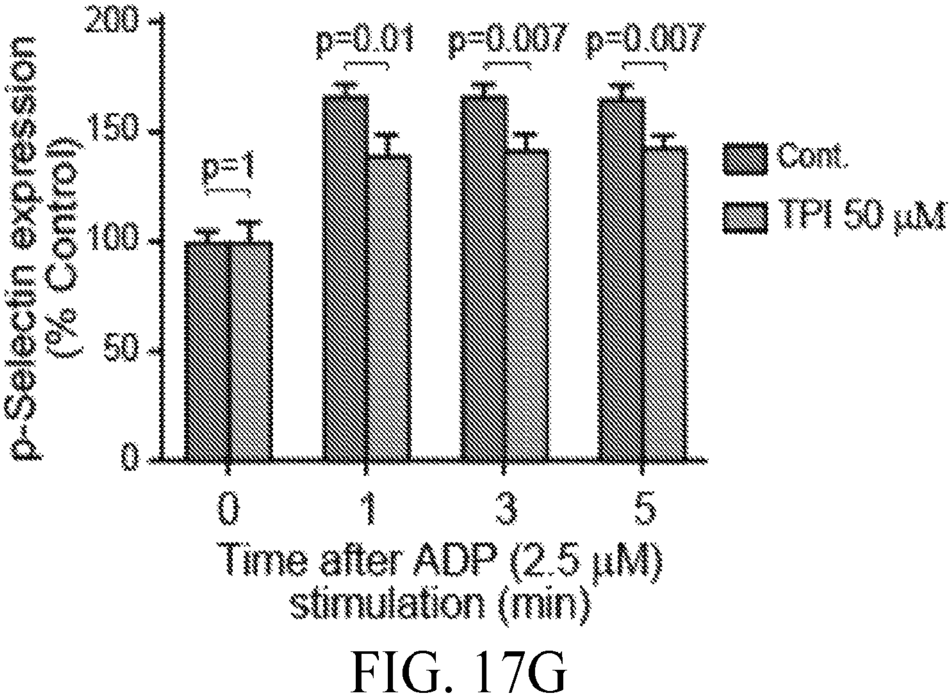

Tipiracil hydrochloride, a potent and specific TYMP inhibitor, attenuates platelet activation. It has been shown that TYMP deficiency significantly attenuated platelet aggregation and P-selectin expression in response to collagen, collagen related peptide (CRP), ADP and thrombin. TPI, an FDA-approved TYMP inhibitor, recently became commercially available. Therefore, its effects on inhibiting platelet activation and preventing thrombosis were examined. TPI dose-dependently (250, 125, and 62.5 μM) inhibited 0.5 μg/ml CRP-induced platelet shape change (not shown) and 50 μM completely blocked CRP-induced platelet aggregation (FIG. 17A). In line with the findings in FIG. 16A, pretreatment of platelets with TPI also dose-dependently inhibited collagen-induced platelet aggregation (FIGS. 17B-17C), which phenocopied the behavior of TYMP-deficient platelets. TPI also attenuated ADP-induced WT platelet aggregation but had no effect on $Tymp^{-/-}$ platelets (FIG. 17D), suggesting that the inhibitory effects of TPI on platelet activation are mediated by TYMP inhibition. This hypothesis is further supported by examination of ADP induced AKT phosphorylation, which has been used as a marker of platelet activation in many studies. As shown in FIG. 17E, it was found that ADP-induced phosphorylation of AKT at S473 was bi-phasic. TYMP deficiency likely had no effect on AKT activation within the first minutes after ADP stimulation, but it dramatically delayed the second phase of AKT phosphorylation. In the second phase of AKT phosphorylation, $Tymp^{-/-}$ platelets took 10 minutes to reach the AKT phosphorylation levels seen in WT platelets after 5 minutes. Inhibition of TYMP with TPI also dramatically reduced ADP-stimulated AKT phosphorylation, especially the second phase (FIG. 17F), and attenuated ADP-stimulated p-selectin expression (FIG. 17G).

Figure 18A:
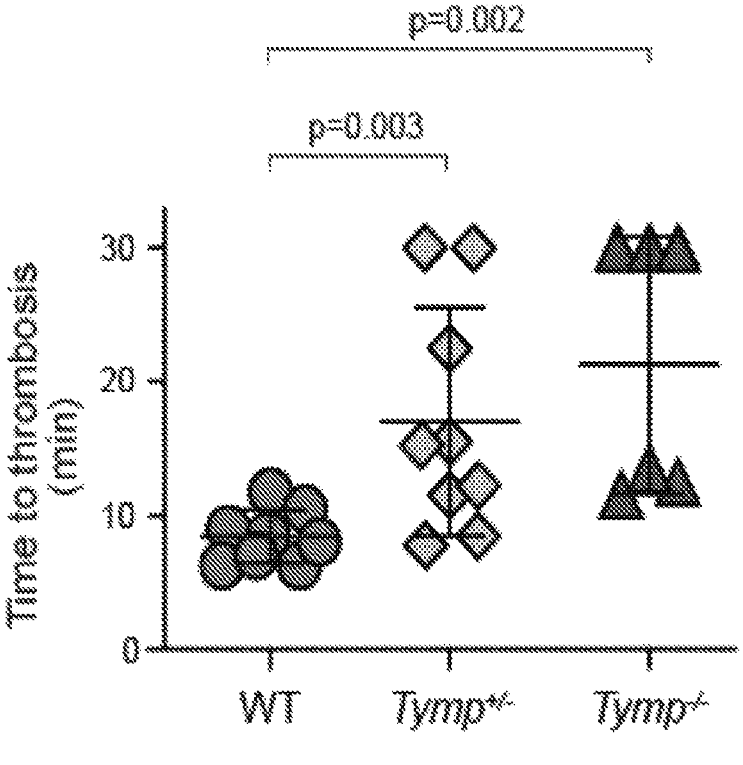
FIGS. 18A-18D include graphs showing TYMP deficiency in vivo inhibits thrombosis in 8-10 weeks WT and $Tymp^{-/-}$ mice in both genders subjected to the 7.5% $FeCl_3$-induced thrombosis model, including (FIGS. 18A-18B) graphs showing the role of TYMP deficiency on thrombosis in female mice, and (FIGS. 18C-18D) graphs showing TYMP deficiency on thrombosis regardless of gender, where the time to thrombosis (FIG. 18A and FIG. 18C) and frequency of vessel opening (FIG. 18B and FIG. 18D) were analyzed in WT, $Tymp^{+/-}$, and $Tymp^{-/-}$ mice.
Figure 18B:
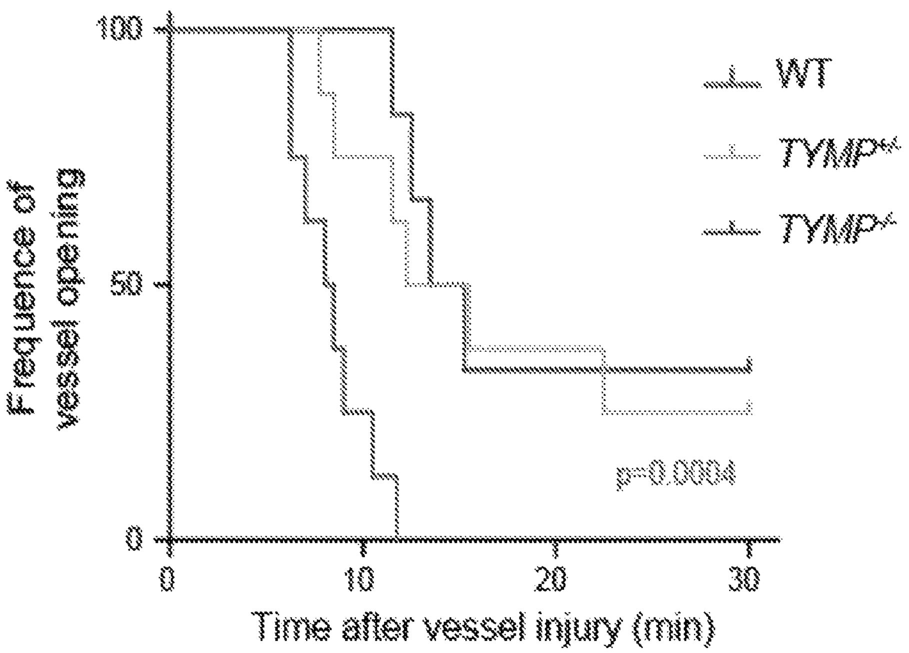
Figure 18C:
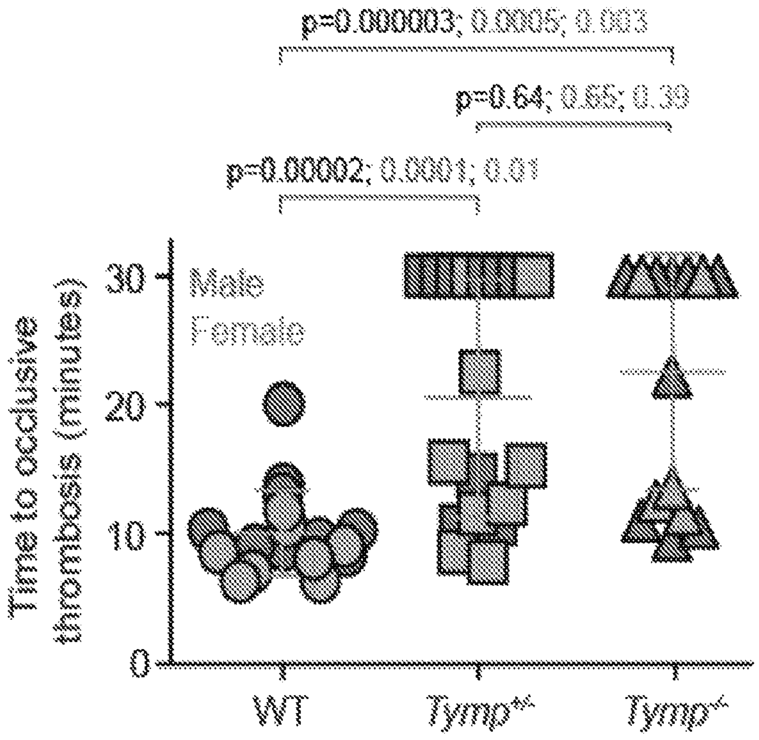
Figure 18D:
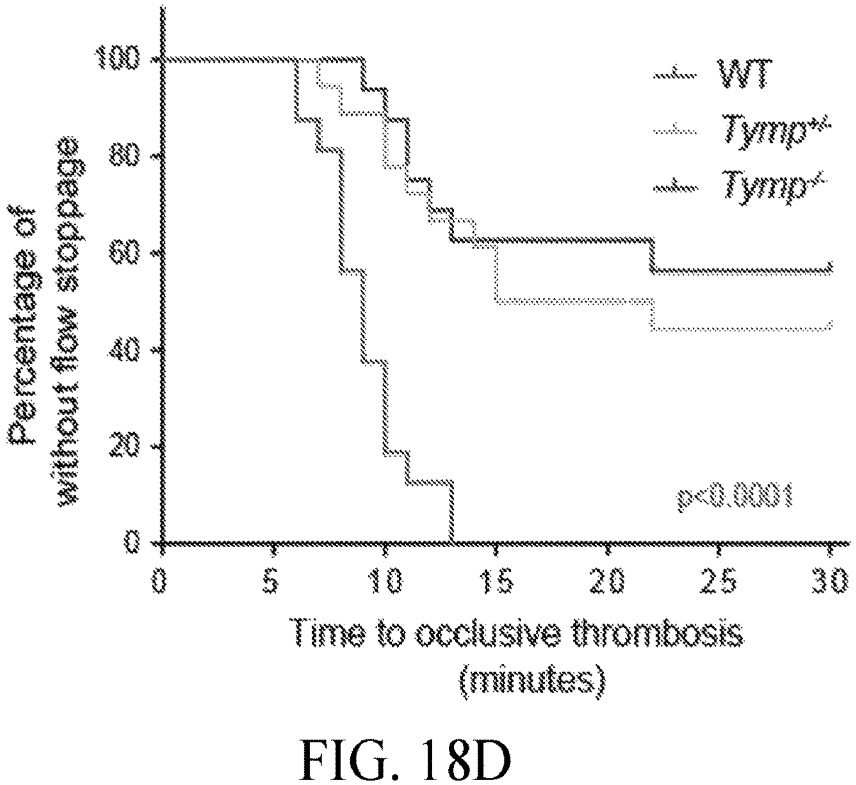

Tymp deficiency results in significant anti-thrombotic effects. It was previously reported that TYMP haploinsufficiency or complete deletion significantly inhibited thrombosis in male mice. It has now been found that TYMP deficiency in female mice also significantly inhibited thrombosis (FIGS. 18A-18B). When combining both male and female mice together, it was found that cessation of blood flow within 30 minutes was seen in all WT mice (n=17) with an average vessel occlusion time of 9.81±2.25 min (FIGS. 18C-18D). 10 of the 18 $Tymp^{-/-}$ mice and 7 of the 16 $Tymp^{-/-}$ mice showed flow cessation within the 30 min observation period, with average occlusion times >20 min. These data indicated that TYMP, a platelet cytosolic protein, plays a mechanistic role in platelet activation and thrombosis, which is independent of gender. Partial deficiency of TYMP is enough to achieve a significant anti-thrombotic effect.

Figure 19A:
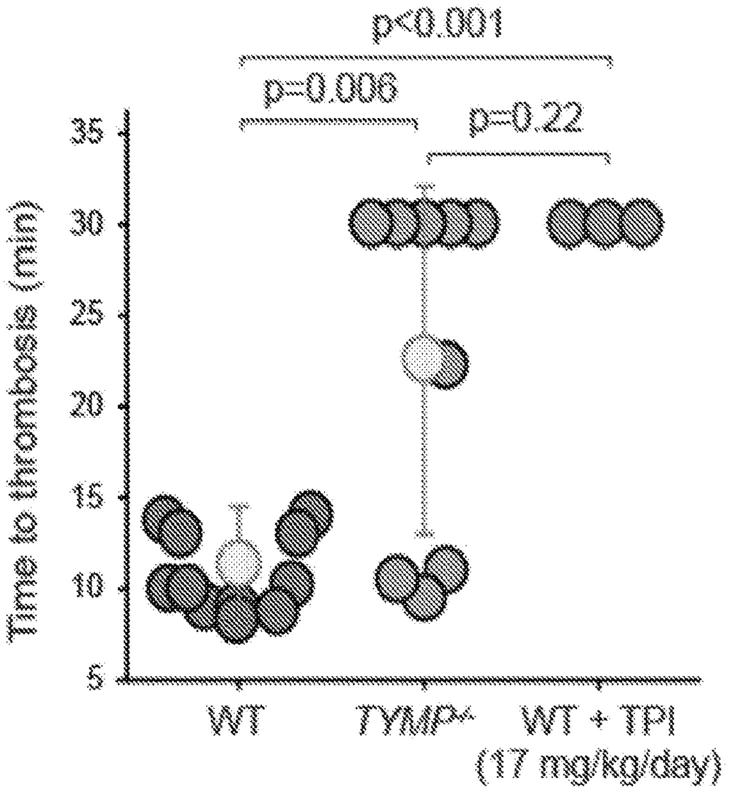
FIGS. 19A-19H include graphs and images showing TPI inhibits thrombosis under both normal and hyperlipidemia conditions without disturbing hemostasis, where WT mice were treated with TPI by intraperitoneal (IP) injection (FIG. 19A) or intravenous injection (FIG. 19C), and oral administration (FIGS. 19D-19E) at the indicated doses and then subjected to the $FeCl_3$ induced thrombosis model, where tail bleeding time was also assessed in mice received TPI IP injection (FIG. 19B), and where (FIGS. 19F-19H) WT mice fed with a western diet (WD, TD.88137) for 4 weeks were subjected to the thrombosis model and thrombosis in age-matched WT mice were used as control (FIG. 19F, representative images from each group, FIG. 19G, mean blood flow cessation time, FIG. 19H, Percentage of mice without flow stoppage).
Figure 19B:
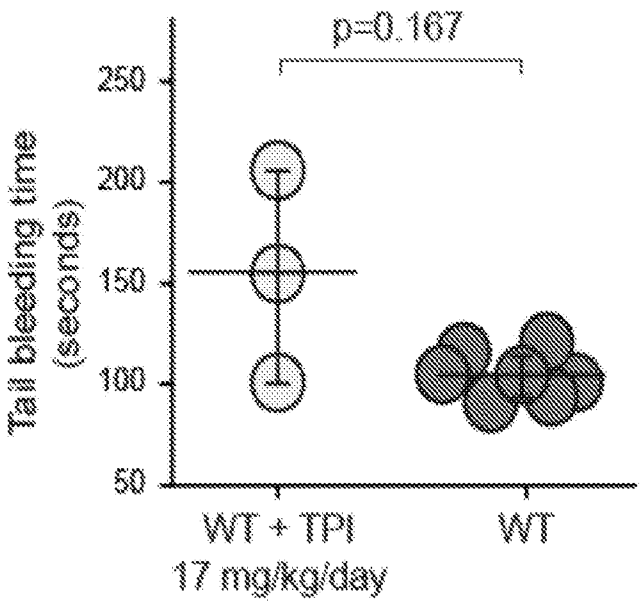
Figure 19C:
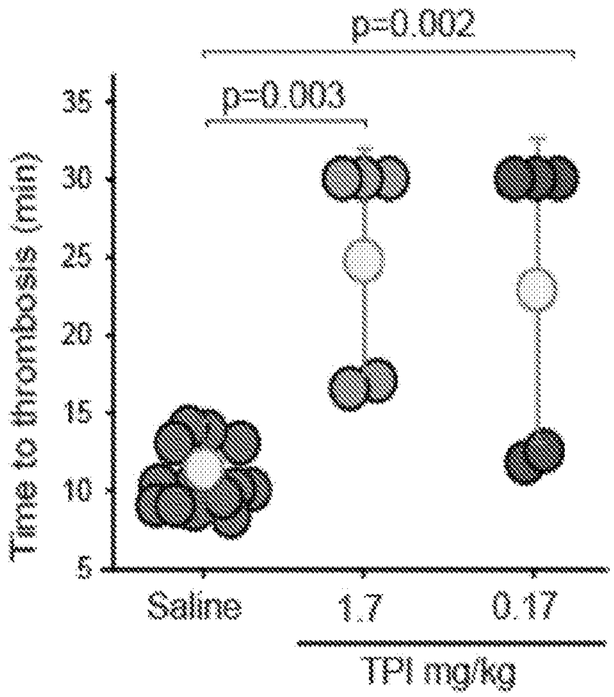
Figure 19D:
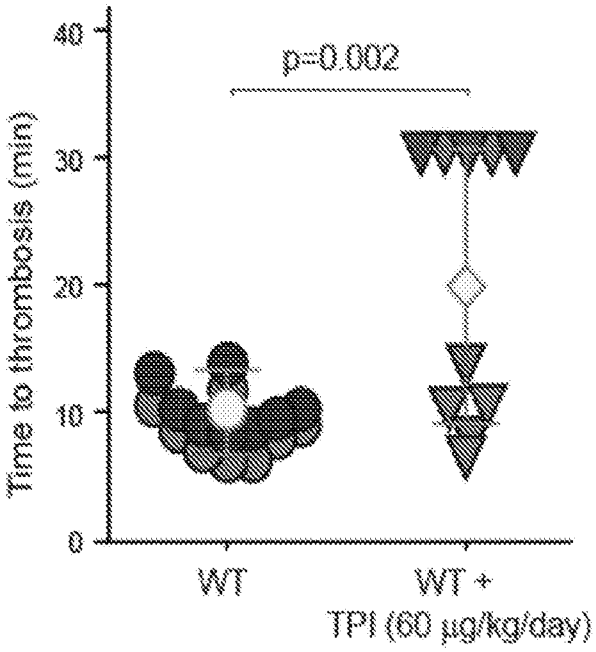
Figure 19E:
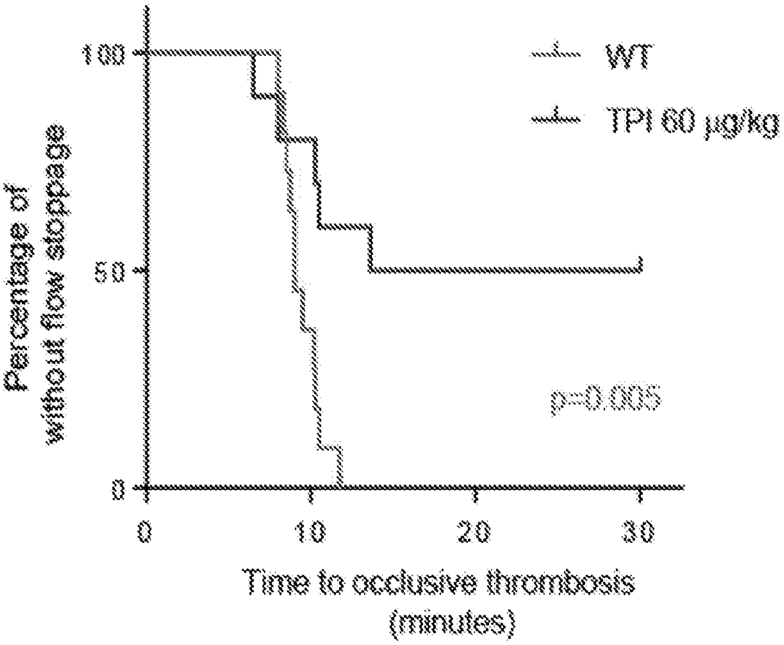

TPI inhibits thrombosis under both normal and hyperlipidemia conditions without disturbing hemostasis. Having shown that inhibition of TYMP with TPI significantly inhibits CRP-, collagen-, and ADP-induced platelet aggregation in vitro, the effects of TPI on in vivo thrombosis were further examined. Intraperitoneal injection of TPI once per day for three days at a dose of 17 mg/kg, which, assuming that total body water is 60% of body weight, equals 100 μM plasma concentration, completely inhibited occlusive thrombus formation in the carotid arteries induced by 7.5% $FeCl_3$ (FIG. 19A). Importantly, this treatment did not significantly affect tail-bleeding time (FIG. 19B). Direct intravenous injection of TPI at doses of 1.7 and 0.17 mg/kg, which equals to 10 and 1 μM plasma concentration based on the calculation mentioned above, also significantly inhibited thrombosis (FIG. 19C) when compared with mice receiving saline injection alone. Interestingly, gavage feeding of TPI at a lower dose of 60 μg/kg/day, which equals a plasma concentration of 340 nM that is 10-fold higher than the TPI IC50 of 34 nM, for 3 days also significantly inhibited in vivo thrombosis (FIGS. 19D-19E). These data strongly indicated that inhibition of TYMP with its specific inhibitor is an effective antithrombotic therapy.

Figure 19F:
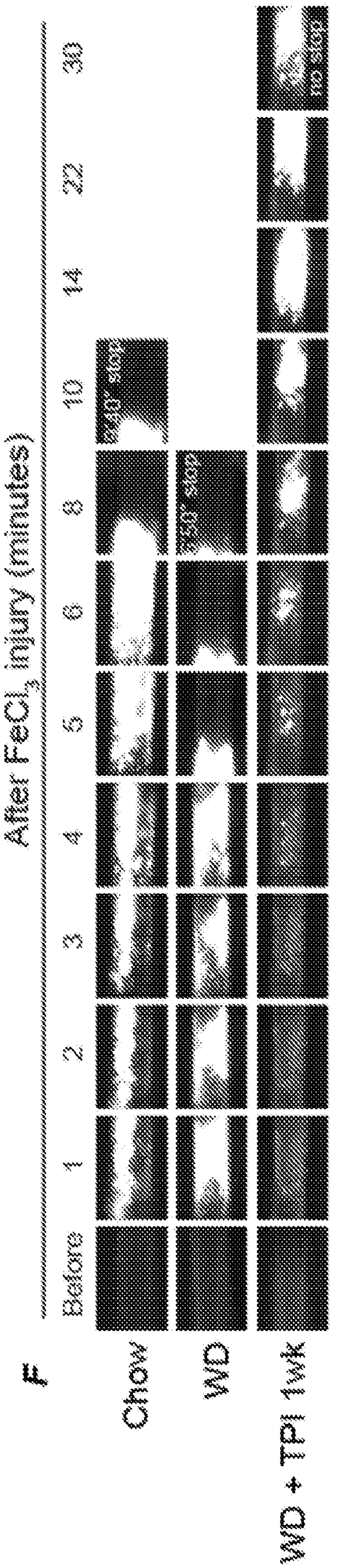
Figure 19G:
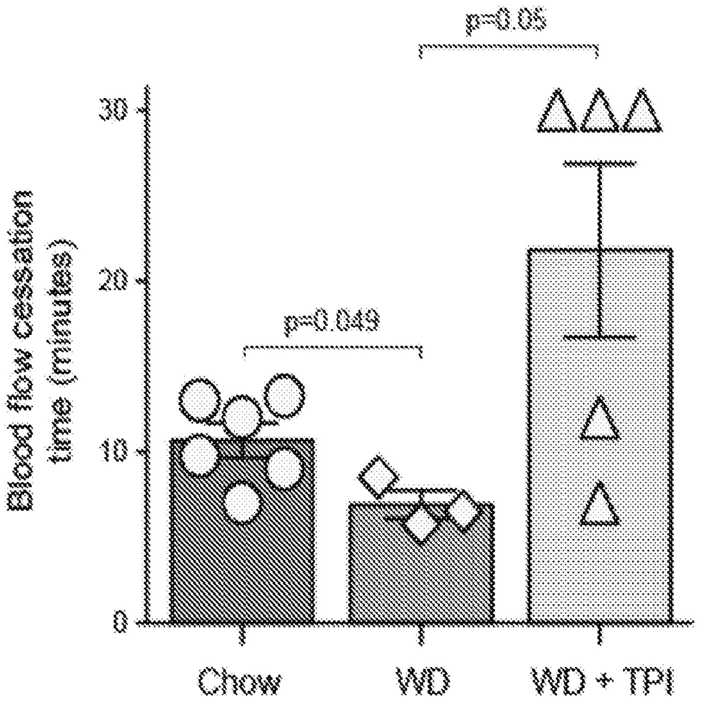
Figure 19H:
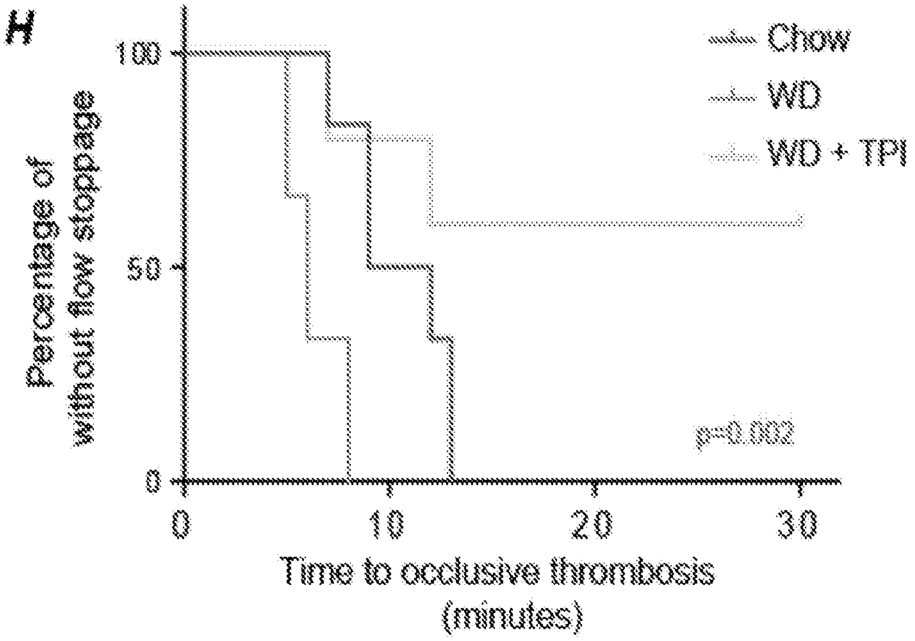

Most of the patients with atherothrombotic vascular diseases have comorbid hyperlipidemia and the associated mortality rates are still unacceptably high. It was previously reported that hyperlipidemia leads to platelet hyperactivity, which may contribute to the development of the pro-thrombotic state. It was discovered that WT mice fed with a WD for 4 weeks is sufficient enough to shorten the thrombosis time when compared to age-matched mice fed with chow. TPI (1 mg/kg) treatment for one week dramatically reduced hyperlipidemia-enhanced thrombosis (FIGS. 19F-19H).

Figure 20A:
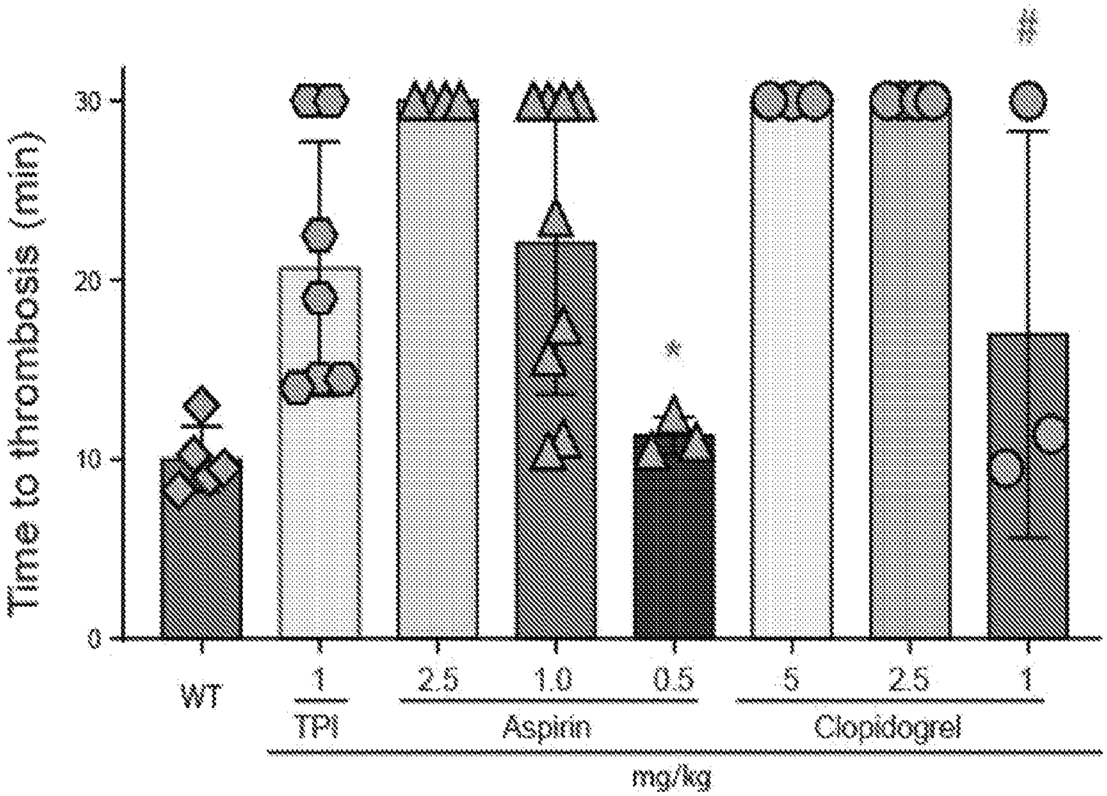
FIGS. 20A-20D include graphs and images showing comparisons of the therapeutic and side effects of TPI with aspirin and clopidogrel, where (FIG. 20A) WT mice were gavage fed with different doses of aspirin and clopidogrel as well as 1 mg/kg TPI in saline and then subjected to the 7.5% $FeCl_3$ induced thrombosis model with WT mice receiving saline used as control, where (FIG. 20B) representative video images were obtained for mice receiving 1 mg/kg TPI, 1 mg/kg aspirin, and 2.5 mg·kg clopidogrel, and where (FIGS. 20C-20D) bleeding time in mice receiving effective doses of aspirin (1.0 mg/kg) and clopidogrel (2.5 mg/kg) was compared with mice that received 1 mg/kg TPI.
Figure 20B:
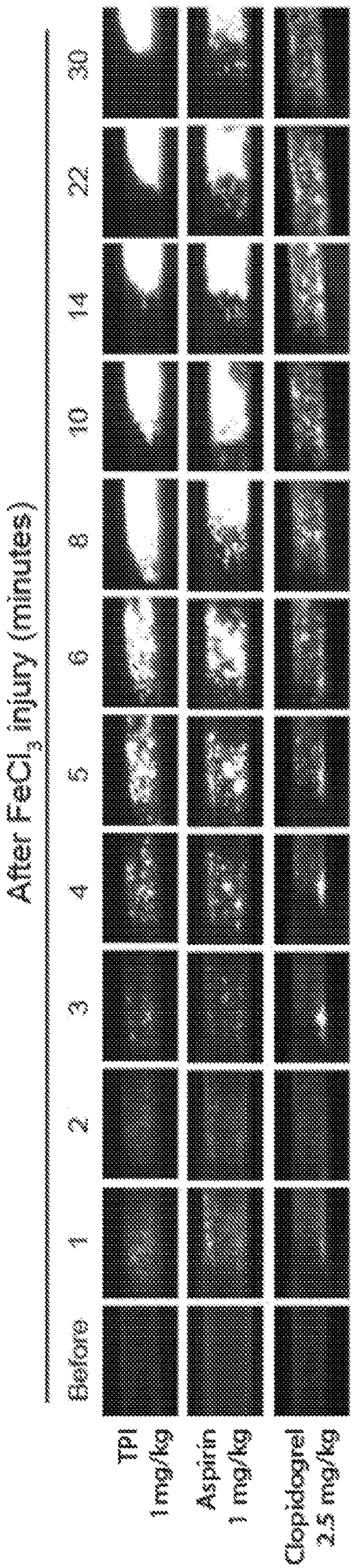
Figure 20C:
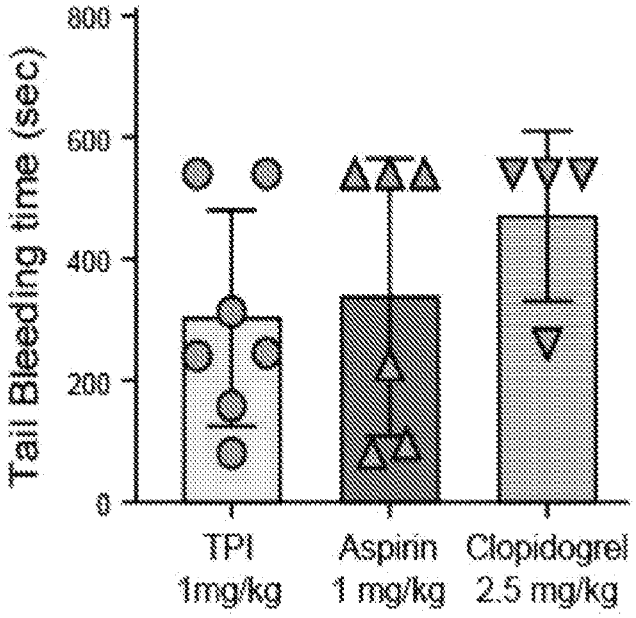
Figure 20D:
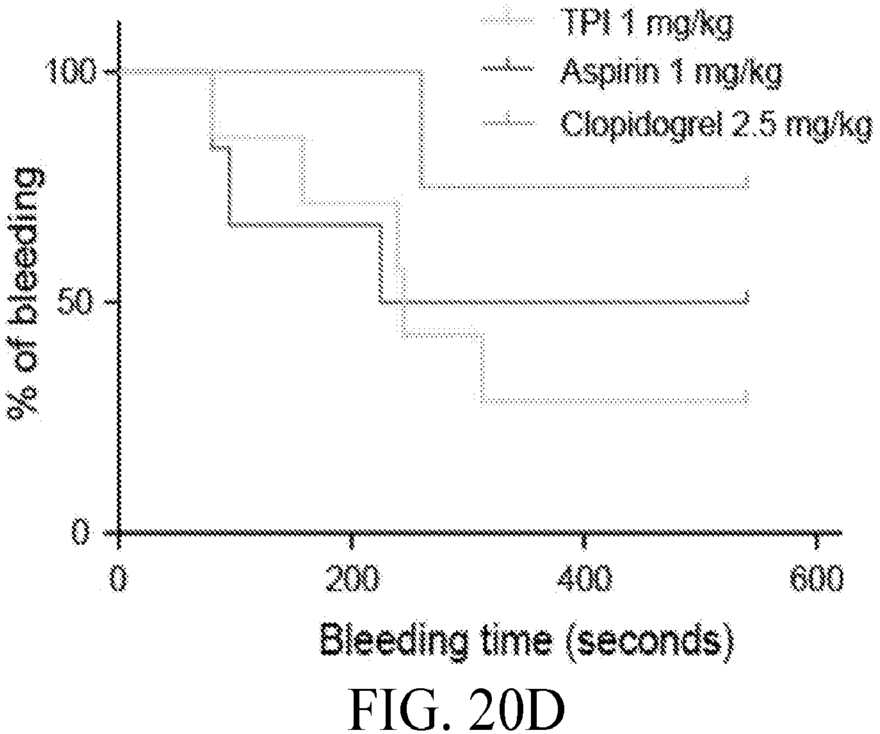

Comparison of the side effects of TPI vs. aspirin and clopidogrel. Current anti-platelet and anti-thrombotic drugs require chronic dosing to be effective and have bleeding side effects. Aspirin and clopidogrel are the most frequently used anti-thrombotic drugs clinically. Their therapeutic and side effects were thus compared with TPI. WT mice were gavage fed with different doses of aspirin and clopidogrel for one week, and then subjected them to the 7.5% $FeCl_3$-induced thrombosis model. It was found that 1 mg/kg/day aspirin and 2.5 mg/kg/day clopidogrel were the lowest effective doses that achieved a significant antithrombotic effect when compared with WT mice without any treatment (FIG. 20A). Although it was found that gavage feeding of TPI, as low as 60 μg/kg/day, significantly inhibited thrombosis in vivo (FIGS. 19D-19E), a higher dose of TPI, 1 mg/kg/day, was chosen in order to explore the potential side effects. The results were then compared to aspirin- and clopidogrel-treated WT mice (FIG. 20B). When comparing the tail bleeding time, although there were no differences found among the three groups, clopidogrel-treated mice had the longest bleeding time (470±70 seconds), the aspirin-treated mice were second (336±93 seconds), and the TPI-treated mice had the shortest bleeding time (302±67 seconds) (FIG. 20C). 75% (3 of the 4) in the clopidogrel group, 50% (3 of the 6) in the aspirin group, and 28.5% (2 of the 7) in the TPI group were considered to have bleeding side effects (FIG. 20D). Mice treated with 1 mg/kg/day of TPI had significantly decreased frequency of bleeding than the clopidogrel-treated mice ($p=0.034$).

Figure 21A:
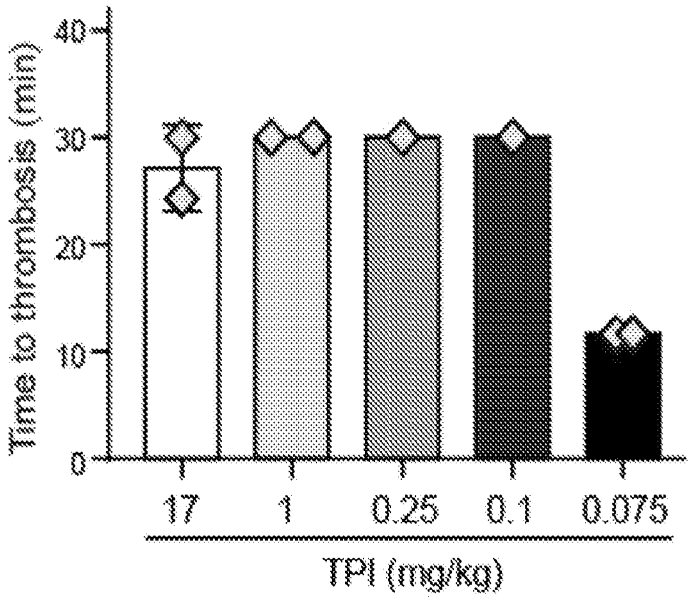
FIGS. 21A-21D include graphs and images showing TPI is a quick-acting anti-thrombotic drug that reduces the effective dose of tPA on preventing occlusive thrombi formation, where thrombosis in WT mice were initiated with 7.5% $FeCl_3$ and 5 minutes later, TPI (FIG. 21A), or tPA (FIG. 21B), or the combination of TPI and tPA (FIG. 21C) in saline at the indicated doses were bolus injected into mice through a jugular vein catheter, and thrombosis times were assessed, and where (FIG. 21D) representative images for mice received 0.25 mg/kg tPA and 75 μg/kg TPI bolus injection are shown.
Figure 21B:
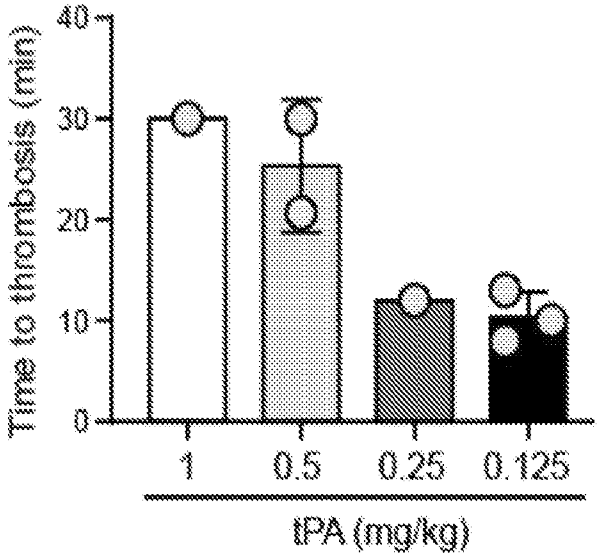
Figure 21C:
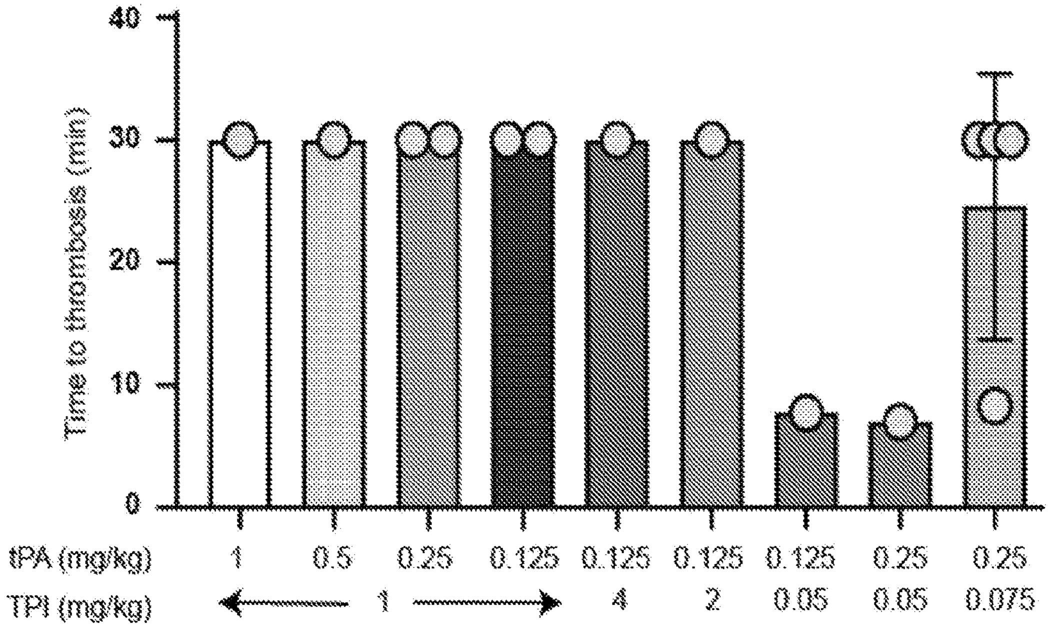
Figure 21D:
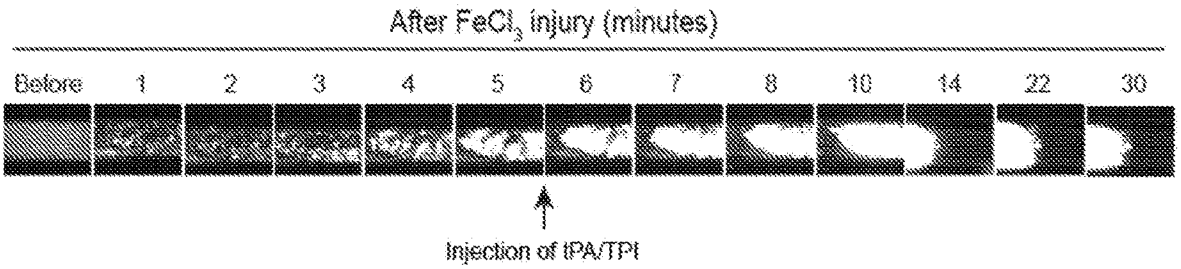

TPI is a quick-acting anti-thrombotic drug and co-administration with tPA reduces the tPA dose needed for effective thrombolysis without disturbing hemostasis. The window for treating patients with acute myocardial infarction or ischemic stroke is narrow and tissue plasminogen activator (tPA) is the only FDA-approved clot-busting drug. Intravenous perfusion of tPA has a high risk of systemic coagulopathies and bleeding complications. By using the $FeCl_3$-induced carotid artery thrombosis model, it was found that bolus injection of tPA (Activase, 1 mg/kg) 5 min after initiation of vascular injury effectively lysed the established thrombi. However, due to de novo platelet activation, persistent formation of new platelet-rich thrombi was also observed after tPA administration; thus, thrombi underwent repeated size variations. By bolus injection of 17 and 1 mg/kg TPI to mice 5 min after 7.5% $FeCl_3$-induced vessel injury, it was found that thrombosis formation was significantly prolonged and there was no blood flow cessation in those WT mice (FIG. 21A). These data indicate that TPI may be a quick-acting anti-thrombotic drug. The minimal effective dose of TPI on inhibiting the growth of the on-site thrombus was further tested and it was found that the lowest effective dose was between 50-100 μg/kg. By using the same thrombosis model, it was also found that the lowest effective dose of tPA on thrombolysis was between 0.25 to 0.5 mg/kg. Lowering the doses of tPA to 0.25 and 0.125 mg/kg had no thrombolytic action (FIG. 21B). Interestingly, when TPI 75 μg/kg and tPA 0.25 mg/kg was co-administered, as shown in FIGS. 21C-21D, a significant inhibition of the growth of the on-site thrombi was found as compared to when each drug was used individually. Increasing doses of either TPI or tPA in combination also significantly prolonged the thrombosis time (FIG. 21C). Most importantly, high doses of TPI (1-4 mg/kg) only slightly prolonged tail-bleeding time to 3.74±0.73 min. These data indicated that co-administration of tPA and TPI reduces the tPA dose required for thrombolysis. TYMP inhibition alone or in combination with a low dose of tPA could be a novel strategy for treating patients with acute myocardial infarction or ischemic stroke without affecting coagulopathy.

DISCUSSION

Vascular thrombosis is the primary event in life threatening diseases, such as myocardial infarction or ischemic stroke, and platelet activation and aggregation are major components of thrombosis. Consequently, various anti-platelet medications are used clinically for the primary or secondary prevention of thrombosis. However, most of these drugs irreversibly block platelet surface receptors involved in platelet activation and aggregation, which results in systemic side effects, including thrombocytopenia and hemorrhage. Therefore, there is a urgent need to elucidate unique molecular mechanisms of platelet-mediated arterial thrombus formation that can be modulated to allow targeted anti-platelet therapy while minimizing systemic risks. In addition, no antiplatelet drugs have been developed to target platelet cytosolic proteins. It was recently discovered that TYMP, a platelet cytoplasmic protein, played important roles in maintaining normal platelet function, and TYMP was also essential for platelet activation induced by multiple agonists, including collagen, ADP, and thrombin. It has now been found that TYMP-enhanced platelet activation is independent of sex and that TYMP deficiency in female mice achieved a similar anti-thrombotic effect to what was seen in male mice. These new data suggest a universal and mechanistic role of TYMP on platelet activation and thrombosis.

In this study, whether TYMP could be inhibited in vivo was thoroughly examined as well as the consequences following TYMP inhibition using the TYMP specific and potent inhibitor, TPI. TPI was delivered to mice using different routes, including intraperitoneal injection, intravenous injection, and oral administration, and the effect was tested using different disease models. The data clearly demonstrated that TPI is an effective and safe anti-thrombotic compound, even under a hyperlipidemic condition. The effective dose of TPI could be as low as 60 μg/kg/day without significantly affecting hemostasis. Most importantly, intravenous injections of TPI, either delivered alone or in combination with tPA, also significantly inhibited the growth of the ongoing thrombi, which makes TYMP inhibition a potential alternative remedy for patients with acute myocardial infarction or stroke. This fast-acting characteristic also indicates that TPI can be used for percutaneous coronary intervention, either alone or combined with other drugs to temporally inhibit platelet function, as TYMP inhibitors rapidly and reversibly inhibit platelet aggregation.

TYMP has a pro-angiogenic effect and previous studies of TYMP are primarily focused on its function on endothelial cells and cancer angiogenesis. Platelets are a major source of TYMP, with each human platelet containing about 5,400 to 11,600 copies of TYMP, but the function of TYMP in platelet physiology and function remains unclear. TYMP has been implicated in diseases that have high risk of thrombosis, such as atherosclerosis, cancer, and diabetes mellitus. In addition, ionizing radiation, which induces significant TYMP expression, has been associated with thrombotic vascular occlusion. In the current study, it was found that TYMP deficiency or inhibition does not affect platelet binding to the collagen-coated surface; however, it dramatically attenuated platelet aggregation on the collagen-coated surface in a flow chamber assay. These data further demonstrated that TYMP likely plays a more important role in the GPVI signaling pathway. GPVI is found exclusively on platelets and megakaryocytes and is the predominant platelet receptor for collagen. Deficiency of GPVI in humans and in mice is not associated with a strong bleeding diathesis. Hitherto, there is no effective and convenient inhibitor targets GPVI. A recent phase I study using Revacept, a dimeric GPVI-Fc fusion protein that blocks collagen/GPVI binding mediated platelet activation, demonstrated that targeting the GPVI signaling is a safe intervention. However, Revacept is delivered by intravenous injection, therefore has limited situational use, such as percutaneous coronary intervention. Revacept has no effects on circulating resting platelets, which indicates that it may have no effect on hyperactive platelets under certain diseased conditions. In contrast, the above data indicated that TPI may have more broad indications than the other anti-platelet drugs.

In addition to GPVI signaling, TYMP also participates in GPCR-mediated platelet activation. In a previous study, it was shown that TYMP deficiency reduced ADP-induced platelet p-selectin expression. Here, it was further demonstrated that TYMP deficiency or inhibition attenuated ADP-induced AKT phosphorylation in platelets. ADP-induced platelet activation requires concomitant signaling from both P2Y1 and P2Y12 receptors that couple to $G_{\alpha q}$ and $G_{\alpha i}$, respectively. However, ADP-induced AKT activation is predominantly mediated by the platelet P2Y12 receptor. While we still do not know how TYMP deficiency increases AKT phosphorylation within one minute, TYMP deficiency may put a "brake" on autocrine or paracrine mechanisms of platelet GPCR activation.

These data provide a strong rationale that TPI can be repositioned as a potential anti-thrombotic medicine. To this end, the prophylactic therapeutic effects and side effects of TPI were compared with aspirin and clopidogrel using the murine $FeCl_3$ induced thrombosis model. It was found that the lowest dose for aspirin and clopidogrel in inhibiting mouse thrombosis is 1 mg/kg and 2.5 mg/kg, respectively. As predicted, these doses of aspirin and clopidogrel dramatically prolonged bleeding time. Although a high dose of TPI (1 mg/kg) occasionally prolonged bleeding time in some mice, mice that received doses of TPI (60 μg/kg) showed no prolonged bleeding time in all cases. As an auxiliary component of the anti-cancer drug, Lonsurf (TAS-102), TPI has been evaluated in clinical trials and has been shown to be systemically safe. Neither systemic bleeding nor mitochondrial neurogastrointestinal encephalomyopathy, an extremely rare autosomal recessive disease that is reportedly associated with TYMP gene loss-of-function mutations, was observed. TYMP deficiency does not affect high dose thrombin-stimulated platelet activation. These data indicate that TPI may be safer and more beneficial than the current anti-platelet drugs. Clinical trial studies are necessary to demonstrate this hypothesis.

In summary, the above-described study demonstrated that TYMP, a platelet cytosolic protein, plays an important role in platelet activation and thrombosis. TYMP can be safely and rapidly inhibited by TPI. TPI-mediated TYMP inhibition dramatically inhibited platelet activation and thrombosis in both normal and hyperlipidemic conditions, as well as in different disease models. Under effective anti-thrombotic doses, TPI does not cause bleeding disorders, as found in patients treated with other anti-platelet drugs.

Example 14—Co-Administration of TPI and Aspirin

Figure 22A:
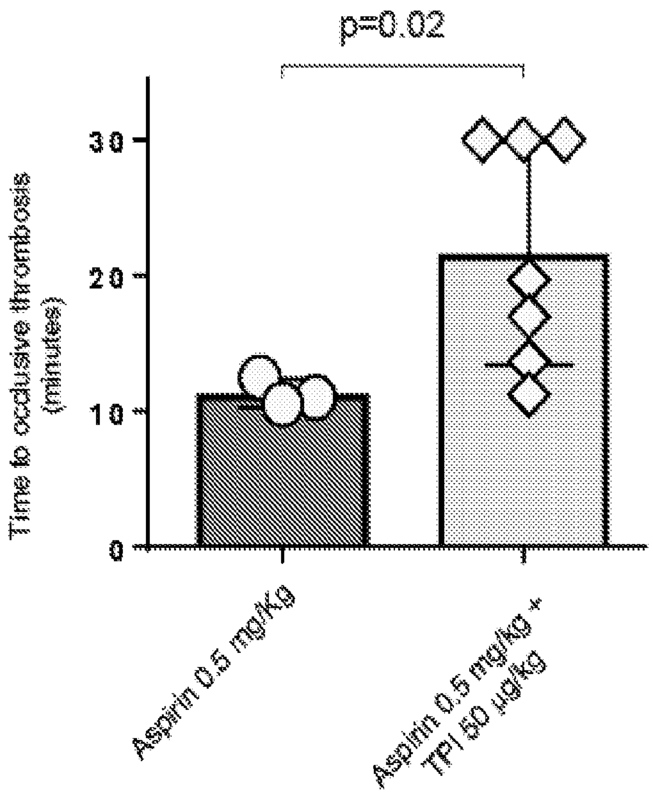
FIGS. 22A-22C are graphs showing the effects of aspirin and a combination of aspirin and TPI in a $FeCl_3$ induced carotid artery injury thrombosis model, including a graph showing (FIG. 22A) the time to occlusive thrombosis for each experimental group, (FIG. 22B) the percent of mice without flow stoppage as a function of time for each experimental group, and (FIG. 22C) the tail bleeding time in WT mice and those receiving a combination of aspirin and TPI.
Figure 22B:
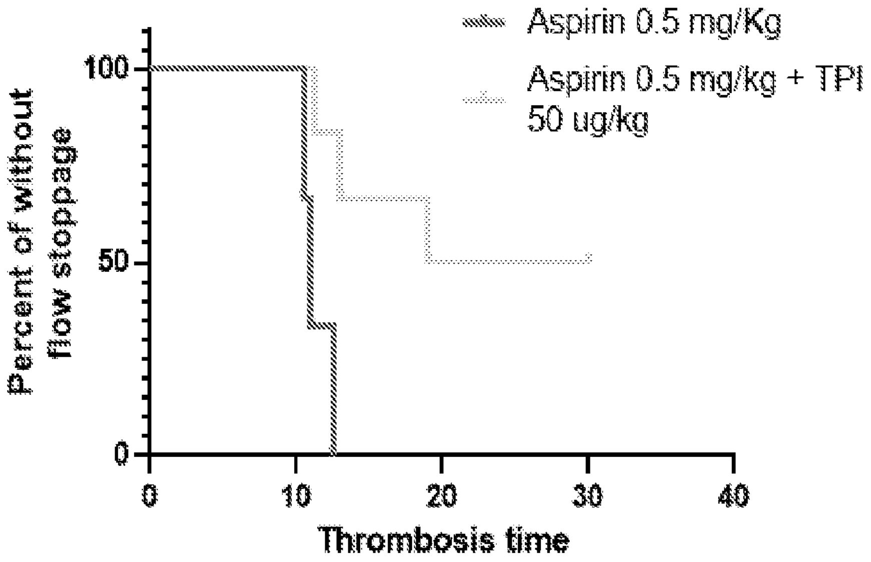
Figure 22C:
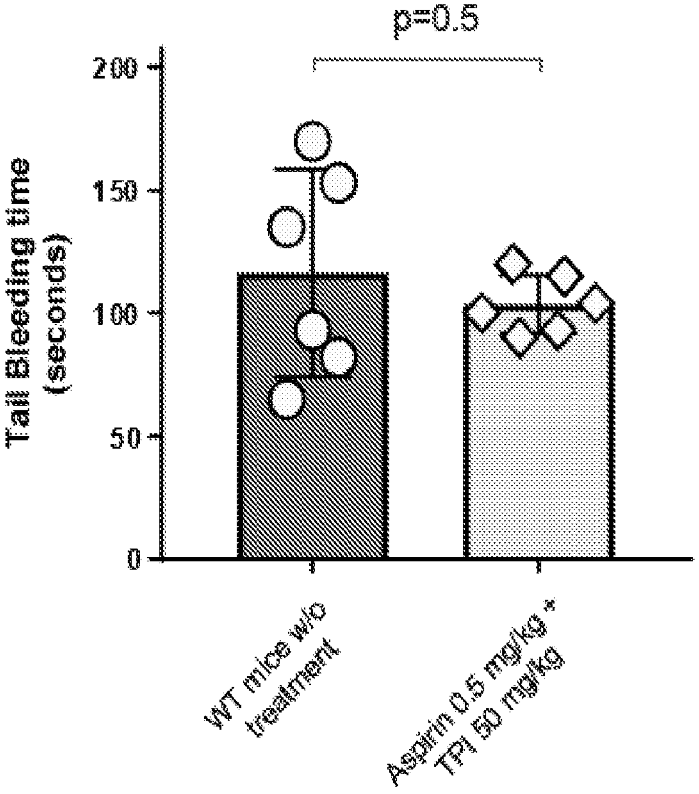

TPI 50 μg/kg intravenous injection did not inhibit the occlusive thrombus formation (see FIG. 21C). As such, C57BL/6 WT mice were gavage fed with Aspirin 0.5 mg/kg/day or Aspirin 0.5 mg/kg/day+TPI 50 μg/kg/day in saline for 7 days and then the mice were subjected to the 7.5% $FeCl_3$ induced carotid artery injury thrombosis model. Upon analysis of the results, it was observed that aspirin 0.5 mg/kg/day had no effect on inhibiting thrombosis (FIG. 22A-22B). However, a combination of Aspirin and TPI in low doses that have no anti-thrombotic effect if used alone, significantly prolonged time to form occlusive thrombosis (FIGS. 22A-22B). In this regard, in comparing with WT mice without any treatment, it was further found that the combination of low dose aspirin and TPI, which significantly prolonged time to form occlusive thrombosis, did not cause bleeding (FIG. 22C). These data thus indicated that combination of low dose Aspirin and TPI is a novel safe dual antiplatelet therapy.

Example 15—TYMP Deficiency Attenuates Type 2 Diabetes Mellitus Associated High Risk of Thrombosis Studies were further undertaken to determine whether TYMP deficiency attenuates the type 2 diabetes mellitus associated high risk of thrombosis. Briefly, WT and $Tymp^{-/-}$ mice were fed with a high fat diet (HFD, D12492, research diet) for 16 weeks to induce obesity and diabetes as described above. These mice were subjected to 7.5% $FeCl_3$ induced carotid artery thrombosis after 16 weeks on HFD.

Figure 23A:
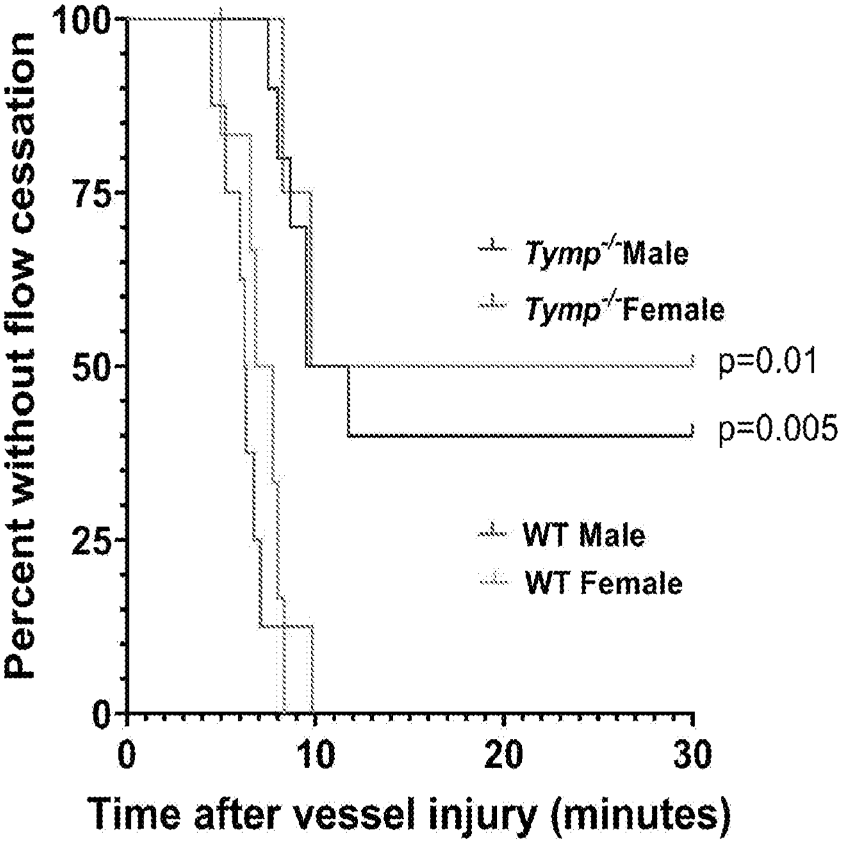
FIGS. 23A-23B include graphs showing TYMP deficiency significantly reduced thrombosis in both male and female mice after 16 weeks of high fat diet feeding as measured by the percent of mice without flow cessation after vessel injury (FIG. 23A) and the time to flow cessation (FIG. 23B).
Figure 23B:
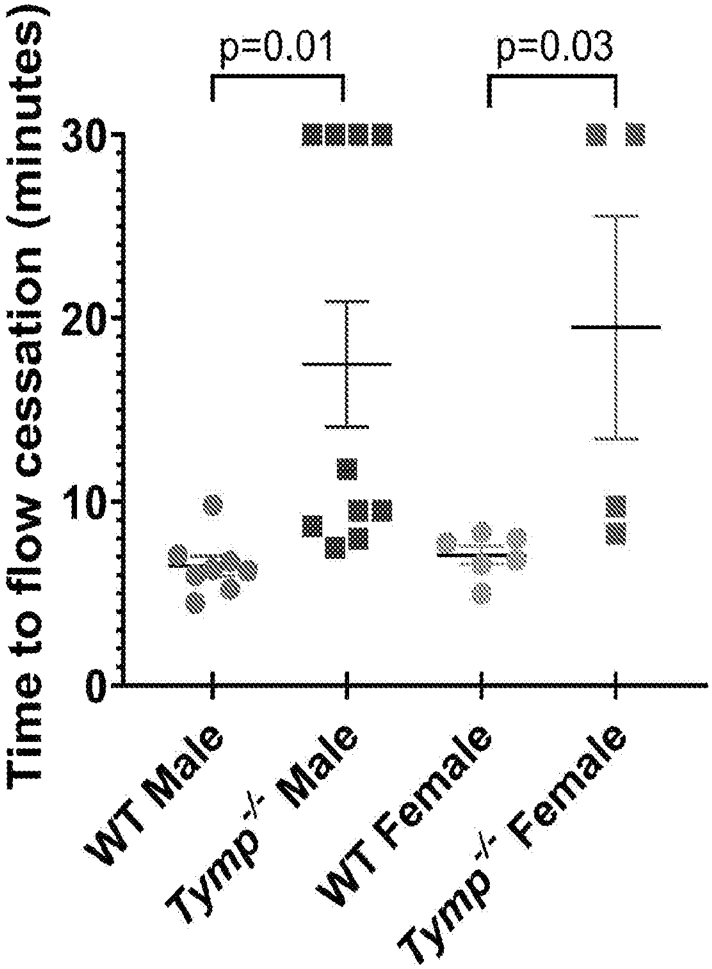
Figure 24:
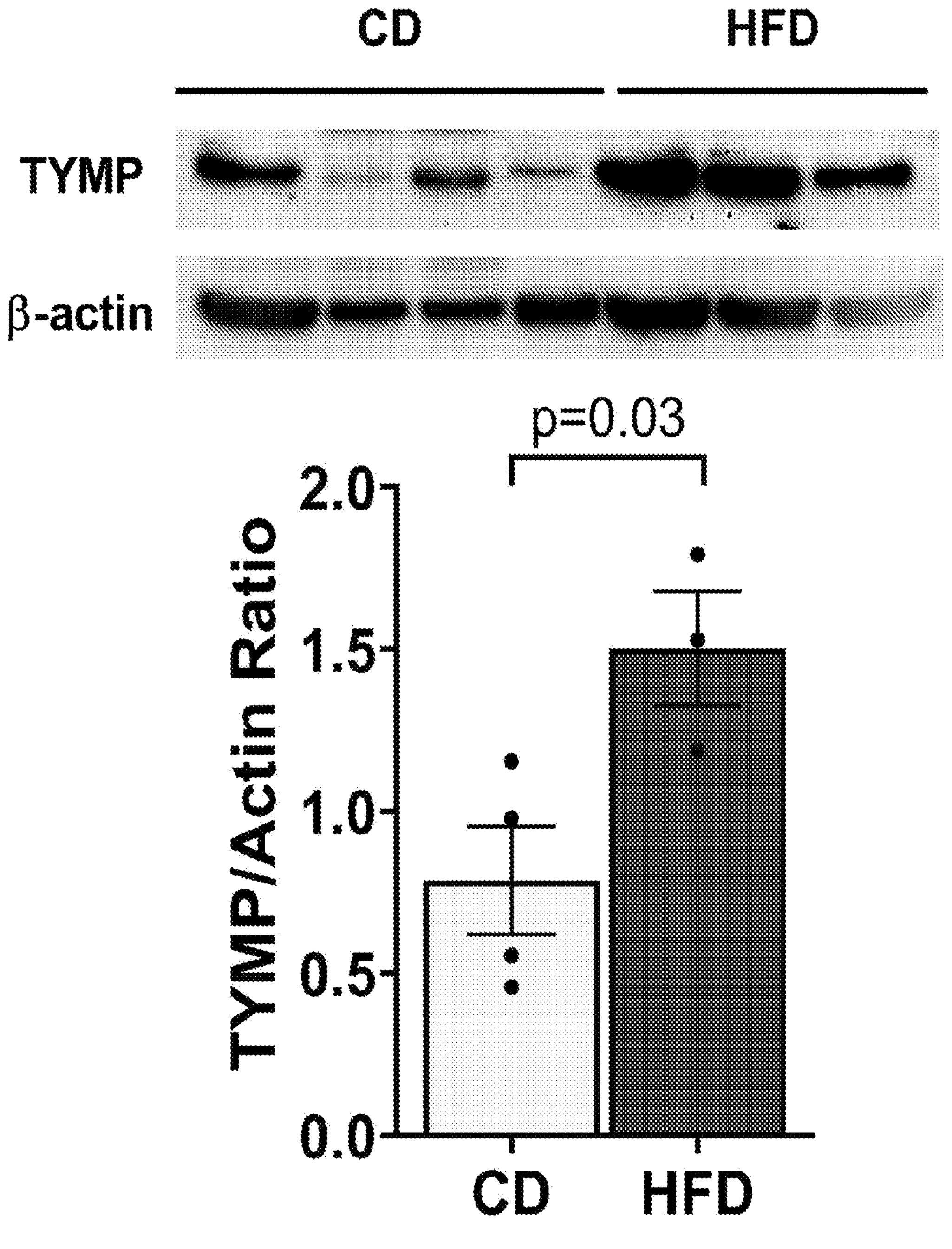
FIG. 24 includes an image and a graph showing TYMP expression in platelets in mice fed a high fat diet.
Figure 25A:
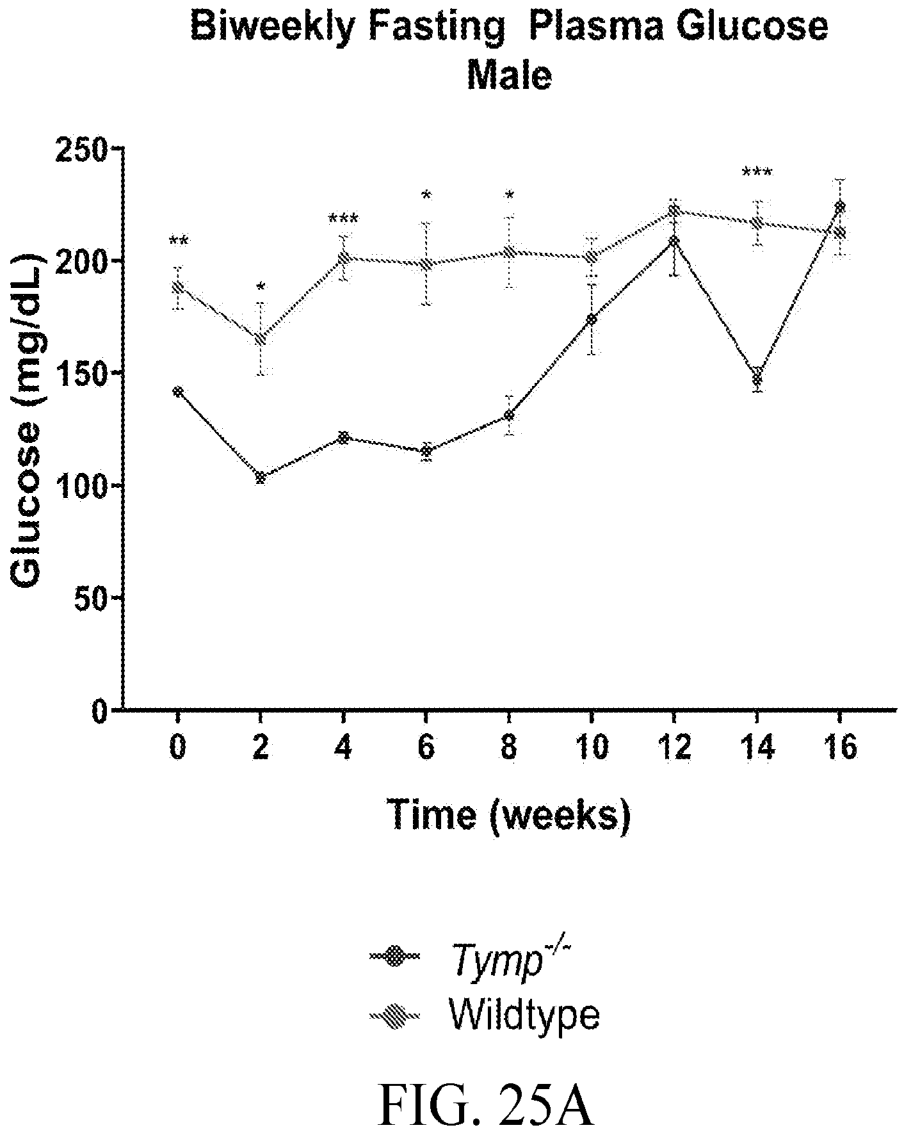
FIGS. 25A-25B include graphs showing biweekly measurement of plasma fasting glucose in male (FIG. 25A) and female (FIG. 25B) mice fed a high fat diet.
Figure 25B:
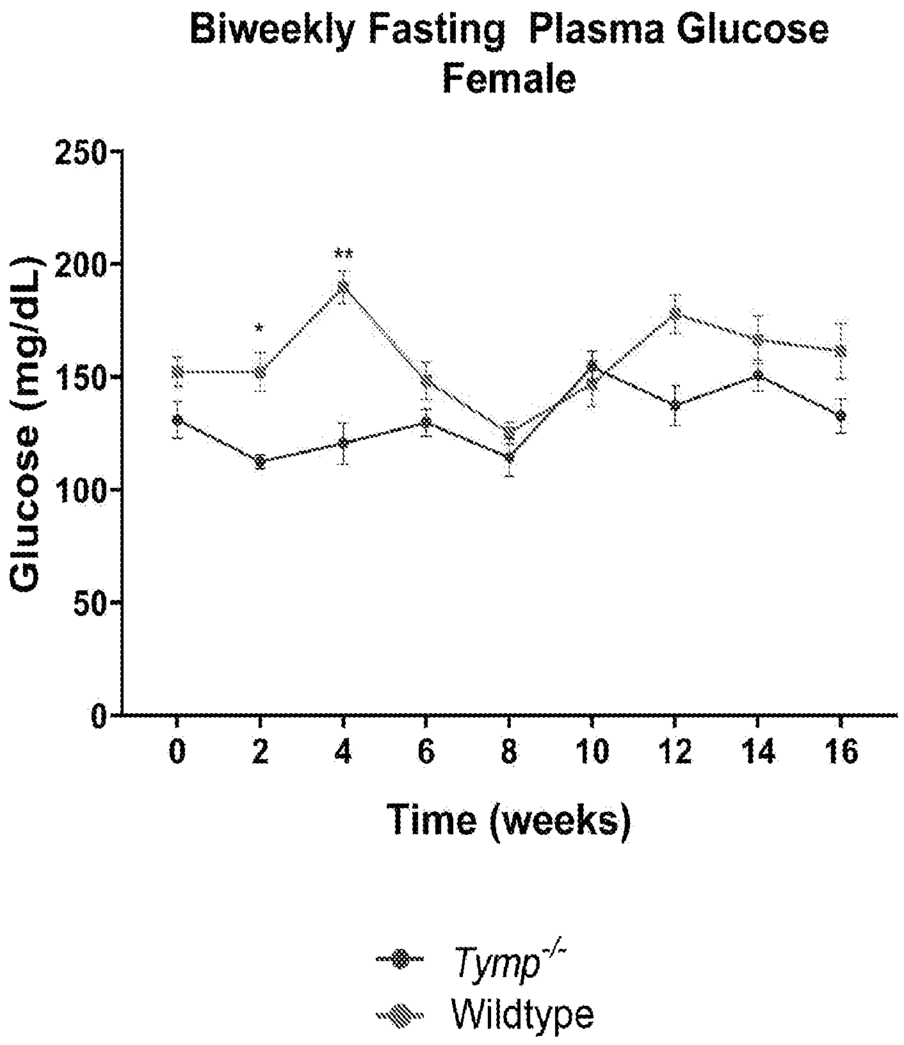
Figure 26A:
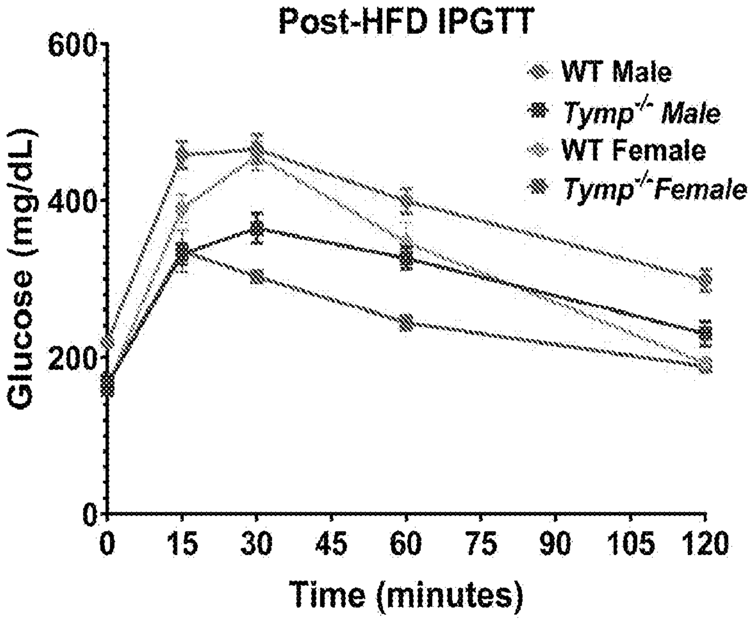
FIGS. 26A-26B include graphs showing the results of an intraperitoneal glucose tolerance test (IPGTT) in mice fed a high fat diet for 16 weeks, including a graph showing glucose levels (FIG. 26A) and a graph showing the area under the curve for each experimental group (FIG. 26B).
Figure 26B:
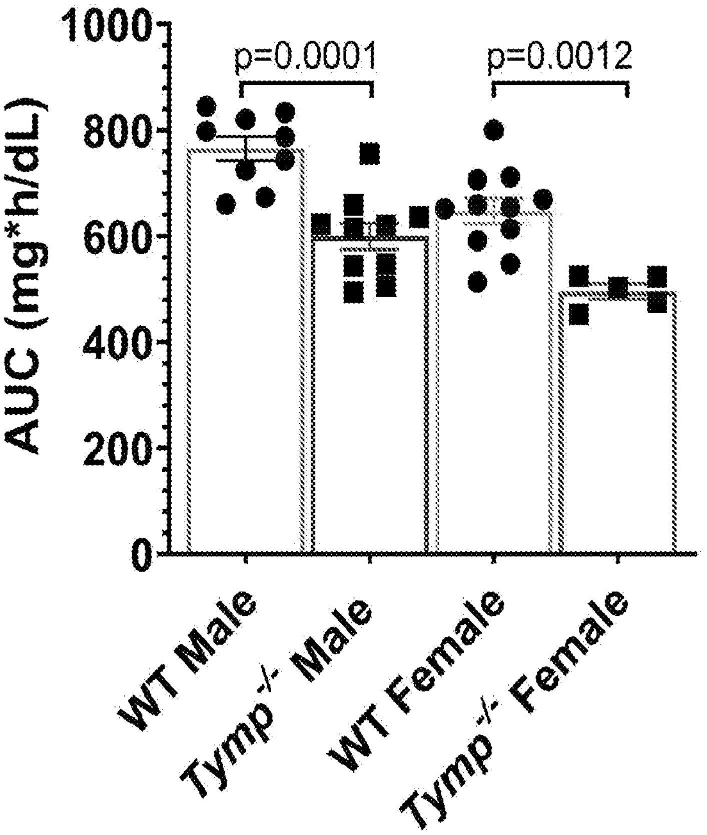

Upon analysis of the results from these further experiments, it was observed that TYMP deficiency significantly reduced thrombosis in both male and female mice after 16 weeks high fat diet feeding (FIGS. 23A-23B). Platelets were also harvested from WT mice fed with HFD or chow. TYMP expression in platelets were then examined by western blot, and it was observed that TYMP expression was significantly increased in the HFD group (FIG. 24). Additionally, in analyzing the biweekly fasting plasma glucose and post-diet glucose tolerance, it was observed that TYMP deficiency resulted in a decrease in fasting plasma glucose levels and glucose tolerance in both males and females (FIGS. 25A-25B and FIGS. 26A-26B, respectively).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Weber C, Noels H. Atherosclerosis: Current pathogenesis and therapeutic options. *Nat Med.* 2011; 17:1410-1422
2. Li W, Yue H. Thymidine phosphorylase: A potential new target for treating cardiovascular disease. *Trends Cardiovasc Med.* 2017
3. Boyle J J, Wilson B, Bicknell R, Harrower S, Weissberg P L, Fan T P. Expression of angiogenic factor thymidine phosphorylase and angiogenesis in human atherosclerosis. *J Pathol.* 2000; 192:234-242
4. Li W, Gigante A, Perez-Perez M J, Yue H, Hirano M, McIntyre T M, Silverstein R L. Thymidine phosphorylase participates in platelet signaling and promotes thrombosis. *Circulation research.* 2014; 115:997-1006
5. Li W, McIntyre T M. Platelet-activating factor receptor affects food intake and body weight. *Genes Dis.* 2015; 2:255-260
6. Piedrahita J A, Zhang S H, Hagaman J R, Oliver P M, Maeda N. Generation of mice carrying a mutant apolipoprotein e gene inactivated by gene targeting in embryonic stem cells. *Proc Natl Acad Sci USA.* 1992; 89:4471-4475
7. Bragg R, Crannage E. Review of pharmacotherapy options for the management of obesity. *J Am Assoc Nurse Pract.* 2016; 28:107-115
8. Flegal K M, Kruszon-Moran D, Carroll M D, Fryar C D, Ogden C L. Trends in obesity among adults in the united states, 2005 to 2014. *JAMA.* 2016; 315:2284-2291

9. Franks P W, Poveda A. Gene-lifestyle and gene-pharmacotherapy interactions in obesity and its cardiovascular consequences. *Current vascular pharmacology.* 2011; 9:401-456

10. Silverstein R L, Febbraio M. Cd36, a scavenger receptor involved in immunity, metabolism, angiogenesis, and behavior. *Sci Signal.* 2009; 2:re3

11. Steinberg D. Atherogenesis in perspective: Hypercholesterolemia and inflammation as partners in crime. *Nat Med.* 2002; 8:1211-1217

12. Blum A. The possible role of red blood cell microvesicles in atherosclerosis. *Eur J Intern Med.* 2009; 20:101-105

13. Muller F, Mutch N J, Schenk W A, Smith S A, Esterl L, Spronk H M, Schmidbauer S, Gahl W A, Morrissey J H, Renne T. Platelet polyphosphates are proinflammatory and procoagulant mediators in vivo. *Cell.* 2009; 139: 1143-1156

14. Barry O P, Pratico D, Savani R C, FitzGerald G A. Modulation of monocyte-endothelial cell interactions by platelet microparticles. *The Journal of clinical investigation.* 1998; 102:136-144

15. Li W, Yue H. Thymidine phosphorylase: A potential new target for treating cardiovascular disease. *Trends Cardiovasc Med.* 2018; 28:157-171

16. Desgranges C, Razaka G, Rabaud M, Bricaud H. Catabolism of thymidine in human blood platelets: Purification and properties of thymidine phosphorylase. *Biochimica et biophysica acta.* 1981; 654:211-218

17. Fox S B, Moghaddam A, Westwood M, Turley H, Bicknell R, Gatter K C, Harris A L. Platelet-derived endothelial cell growth factor/thymidine phosphorylase expression in normal tissues: An immunohistochemical study. *J Pathol.* 1995; 176:183-190

18. van Kuilenburg A B, Zoetekouw L. Determination of thymidine phosphorylase activity in human blood cells and fibroblasts by a nonradiochemical assay using reversed-phase high-performance liquid chromatography. *Nucleosides Nucleotides Nucleic Acids.* 2006; 25:1261-1264

19. Ignatescu M C, Gharehbaghi-Schnell E, Hassan A, Rezaie-Majd S, Korschineck I, Schleef R R, Glogar H D, Lang I M. Expression of the angiogenic protein, platelet-derived endothelial cell growth factor, in coronary atherosclerotic plaques: In vivo correlation of lesional microvessel density and constrictive vascular remodeling. *Arteriosclerosis, thrombosis, and vascular biology.* 1999; 19:2340-2347

20. Li W, Tanaka K, Morioka K, Uesaka T, Yamada N, Takamori A, Handa M, Tanabe S, Ihaya A. Thymidine phosphorylase gene transfer inhibits vascular smooth muscle cell proliferation by upregulating heme oxygenase-1 and p27kip1. *Arteriosclerosis, thrombosis, and vascular biology.* 2005; 25:1370-1375

21. Yue H, Tanaka K, Furukawa T, Karnik S S, Li W. Thymidine phosphorylase inhibits vascular smooth muscle cell proliferation via upregulation of stat3. *Biochimica et biophysica acta.* 2012; 1823:1316-1323

22. Somjen D, Jaffe A, Knoll E, Kohen F, Amir-Zaltsman Y, Stern N. Platelet-derived endothelial cell growth factor inhibits DNA synthesis in vascular smooth muscle cells. *Am J Hypertens.* 1999; 12:882-889

23. Handa M, Li W, Morioka K, Takamori A, Yamada N, Ihaya A. Adventitial delivery of platelet-derived endothelial cell growth factor gene prevented intimal hyperplasia of vein graft. *J Vasc Surg.* 2008; 48:1566-1574

24. Cizek S M, Bedri S, Talusan P, Silva N, Lee H, Stone J R. Risk factors for atherosclerosis and the development of preatherosclerotic intimal hyperplasia. *Cardiovascular pathology: the official journal of the Society for Cardiovascular Pathology.* 2007; 16:344-350

25. Hamed E A, Zakary M M, Abdelal R M, Abdel Moneim E M. Vasculopathy in type 2 diabetes mellitus: Role of specific angiogenic modulators. *J Physiol Biochem.* 2011; 67:339-349

26. Toyoda Y, Tabata S, Kishi J, et al. Thymidine phosphorylase regulates the expression of cxcl10 in rheumatoid arthritis fibroblast-like synoviocytes. *Arthritis and rheumatism.* 2013

27. Moore K J, Sheedy F J, Fisher E A. Macrophages in atherosclerosis: A dynamic balance. Nature reviews. *Immunology.* 2013; 13:709-721

28. Skeoch S, Bruce I N. Atherosclerosis in rheumatoid arthritis: Is it all about inflammation? *Nat Rev Rheumatol.* 2015; 11:390-400

29. Mayer R J, Van Cutsem E, Falcone A, et al. Randomized trial of tas-102 for refractory metastatic colorectal cancer. *N Engl J Med.* 2015; 372:1909-1919

30. Yoshino T, Mizunuma N, Yamazaki K, et al. Tas-102 monotherapy for pretreated metastatic colorectal cancer: A double-blind, randomised, placebo-controlled phase 2 trial. *The lancet oncology.* 2012; 13:993-1001

31. Doi T, Ohtsu A, Yoshino T, Boku N, Onozawa Y, Fukutomi A, Hironaka S, Koizumi W, Sasaki T. Phase i study of tas-102 treatment in japanese patients with advanced solid tumours. *British journal of cancer.* 2012; 107:429-434

32. Hong D S, Abbruzzese J L, Bogaard K, Lassere Y, Fukushima M, Mita A, Kuwata K, Hoff P M. Phase i study to determine the safety and pharmacokinetics of oral administration of tas-102 in patients with solid tumors. *Cancer.* 2006; 107:1383-1390

33. Johansson M. Identification of a novel human uridine phosphorylase. *Biochem Biophys Res Commun.* 2003; 307:41-46

34. Roosild T P, Castronovo S, Villoso A, Ziemba A, Pizzorno G. A novel structural mechanism for redox regulation of uridine phosphorylase 2 activity. *J Struct Biol.* 2011; 176:229-237

35. Kubilus J, Lee L D, Baden H P. Purification of thymidine phosphorylase from human amniochorion. *Biochimica et Biophysica Acta (BBA)—Enzymology.* 1978; 527:221-228

36. Miyazono K, Okabe T, Urabe A, Takaku F, Heldin C H. Purification and properties of an endothelial cell growth factor from human platelets. *The Journal of biological chemistry.* 1987; 262:4098-4103

37. Li W, Chiba Y, Kimura T, Morioka K, Uesaka T, Ihaya A, Muraoka R. Transmyocardial laser revascularization induced angiogenesis correlated with the expression of matrix metalloproteinases and platelet-derived endothelial cell growth factor. *Eur J Cardiothorac Surg.* 2001; 19:156-163

38. Li P G, Xu J W, Ikeda K, Kobayakawa A, Kayano Y, Mitani T, Ikami T, Yamori Y. Caffeic acid inhibits vascular smooth muscle cell proliferation induced by angiotensin ii in stroke-prone spontaneously hypertensive rats. *Hypertens Res.* 2005; 28:369-377

39. Li W, Tanaka K, Morioka K, Takamori A, Handa M, Yamada N, Ihaya A. Long-term effect of gene therapy for chronic ischemic myocardium using platelet-derived endothelial cell growth factor in dogs. *J Gene Med.* 2008; 10:412-420

40. Koukourakis M I, Giatromanolaki A, O'Byrne K J, Comley M, Whitehouse R M, Talbot D C, Gatter K C, Harris A L. Platelet-derived endothelial cell growth factor expression correlates with tumour angiogenesis and prognosis in non-small-cell lung cancer. *Br J Cancer.* 1997; 75:477-481

41. Akiyama S, Furukawa T, Sumizawa T, Takebayashi Y, Nakajima Y, Shimaoka S, Haraguchi M. The role of thymidine phosphorylase, an angiogenic enzyme, in tumor progression. *Cancer Sci.* 2004; 95:851-857

42. Nakajima Y, Madhyastha R, Maruyama M. 2-deoxy-d-ribose, a downstream mediator of thymidine phosphorylase, regulates tumor angiogenesis and progression. *Anticancer Agents Med Chem.* 2009; 9:239-245

43. Yamada N, Li W, Ihaya A, Kimura T, Morioka K, Uesaka T, Takamori A, Handa M, Tanabe S, Tanaka K. Platelet-derived endothelial cell growth factor gene therapy for limb ischemia. *J Vasc Surg.* 2006; 44:1322-1328

44. Souza S J, Luzia L A, Santos S S, Rondo P H. Lipid profile of hiv-infected patients in relation to antiretroviral therapy: A review. *Revista da Associacao Medica Brasileira.* 2013; 59:186-198

45. de Almeida E R, Reiche E M, Kallaur A P, Flauzino T, Watanabe M A. The roles of genetic polymorphisms and human immunodeficiency virus infection in lipid metabolism. *BioMed research international.* 2013; 2013:836790

46. Pujari S N, Dravid A, Naik E, Bhagat S, Tash K, Nadler J P, Sinnott J T. Lipodystrophy and dyslipidemia among patients taking first-line, world health organization-recommended highly active antiretroviral therapy regimens in western india. *Journal of acquired immune deficiency syndromes.* 2005; 39:199-202

47. Longenecker C T, Funderburg N T, Jiang Y, Debanne S, Storer N, Labbato D E, Lederman M M, McComsey G A. Markers of inflammation and cd8 t-cell activation, but not monocyte activation, are associated with subclinical carotid artery disease in hiv-infected individuals. *HIV medicine.* 2013; 14:385-390

48. Asmann Y W, Necela B M, Kalari K R, et al. Detection of redundant fusion transcripts as biomarkers or disease-specific therapeutic targets in breast cancer. *Cancer research.* 2012; 72:1921-1928

49. Derrien T, Johnson R, Bussotti G, et al. The gencode v7 catalog of human long noncoding rnas: Analysis of their gene structure, evolution, and expression. *Genome Res.* 2012; 22:1775-1789

50. Lee Y H, Nair S, Rousseau E, Allison D B, Page G P, Tataranni P A, Bogardus C, Permana P A. Microarray profiling of isolated abdominal subcutaneous adipocytes from obese vs non-obese pima indians: Increased expression of inflammation-related genes. *Diabetologia.* 2005; 48:1776-1783

51. Lopez L C, Akman H O, Garcia-Cazorla A, Dorado B, Marti R, Nishino I, Tadesse S, Pizzorno G, Shungu D, Bonilla E, Tanji K, Hirano M. Unbalanced deoxynucleotide pools cause mitochondrial DNA instability in thymidine phosphorylase-deficient mice. *Human molecular genetics.* 2009; 18:714-722

52. Yu S, Matsusue K, Kashireddy P, Cao W Q, Yeldandi V, Yeldandi A V, Rao M S, Gonzalez F J, Reddy J K. Adipocyte-specific gene expression and adipogenic steatosis in the mouse liver due to peroxisome proliferator-activated receptor gamma1 (ppargamma1) overexpression. *The Journal of biological chemistry.* 2003; 278:498-505

53. Inoue M, Ohtake T, Motomura W, Takahashi N, Hosoki Y, Miyoshi S, Suzuki Y, Saito H, Kohgo Y, Okumura T. Increased expression of ppargamma in high fat diet-induced liver steatosis in mice. *Biochemical and biophysical research communications.* 2005; 336:215-222

54. Iltzsch M H, el Kouni M H, Cha S. Kinetic studies of thymidine phosphorylase from mouse liver. *Biochemistry.* 1985; 24:6799-6807

55. Ikeguchi M, Sakatani T, Ueda T, Hirooka Y, Kaibara N. Thymidine phosphorylase activity in liver tissue and its correlation with multifocal occurrence of hepatocellular carcinomas. In vivo. 2001; 15:265-270

56. Ryden M, Amer P. Subcutaneous adipocyte lipolysis contributes to circulating lipid levels. *Arteriosclerosis, thrombosis, and vascular biology.* 2017; 37:1782-1787

57. Li W, Nieman, M., Sen Gupta, A. Ferric chloride-induced murine thrombosis models. *J. Vis. Exp.* 2016; 115:e54479

58. Li W, McIntyre T M, Silverstein R L. Ferric chloride-induced murine carotid arterial injury: A model of redox pathology. *Redox Biol.* 2013; 1:50-55

59. Zhang F, Zarkada G, Han J, et al. Lacteal junction zippering protects against diet-induced obesity. *Science.* 2018; 361:599-603

60. Li W, Febbraio M, Reddy S P, Yu D Y, Yamamoto M, Silverstein R L. Cd36 participates in a signaling pathway that regulates ros formation in murine vsmcs. *J Clin Invest.* 2010; 120:3996-4006

61. Sztalryd C, Brasaemle D L. The perilipin family of lipid droplet proteins: Gatekeepers of intracellular lipolysis. *Biochim Biophys Acta Mol Cell Biol Lipids.* 2017; 1862:1221-1232

62. Boukouris A E, Zervopoulos S D, Michelakis E D. Metabolic enzymes moonlighting in the nucleus: Metabolic regulation of gene transcription. *Trends Biochem Sci.* 2016; 41:712-730

63. Huang X, Holden H M, Raushel F M. Channeling of substrates and intermediates in enzyme-catalyzed reactions. *Annu Rev Biochem.* 2001; 70:149-180

64. Matsuda S, Adachi J, Ihara M, Tanuma N, Shima H, Kakizuka A, Ikura M, Ikura T, Matsuda T. Nuclear pyruvate kinase m2 complex serves as a transcriptional coactivator of arylhydrocarbon receptor. *Nucleic Acids Res.* 2016; 44:636-647

65. Bell C G. The epigenomic analysis of human obesity. *Obesity* (*Silver Spring*). 2017; 25:1471-1481

66. Yu X, Li S. Non-metabolic functions of glycolytic enzymes in tumorigenesis. *Oncogene.* 2017; 36:2629-2636

67. Liu H, Liu Z, Du J, He J, Lin P, Amini B, Starbuck M W, Novane N, Shah J J, Davis R E, Hou J, Gagel R F, Yang J. Thymidine phosphorylase exerts complex effects on bone resorption and formation in myeloma. *Sci Transl Med.* 2016; 8:353ra113

68. Li W, Tanaka K, Ihaya A, Fujibayashi Y, Takamatsu S, Morioka K, Sasaki M, Uesaka T, Kimura T, Yamada N, Tsuda T, Chiba Y. Gene therapy for chronic myocardial ischemia using platelet-derived endothelial cell growth factor in dogs. *Am J Physiol Heart Circ Physiol.* 2005; 288:H408-415

69. Yue H, Febbraio M, Klenotic P A, Kennedy D J, Wu Y, Chen S, Gohara A F, Li O, Belcher A, Kuang B, McIntyre T M, Silverstein R L, Li W. Cd36 enhances vascular smooth muscle cell proliferation and development of neointimal hyperplasia. *Arteriosclerosis, thrombosis, and vascular biology.* 2018:ATVBAHA118312186

70. Visser M, Bouter L M, McQuillan G M, Wener M H, Harris T B. Elevated c-reactive protein levels in overweight and obese adults. *JAMA.* 1999; 282:2131-2135

71. Hotamisligil G S. Inflammation, metaflammation and immunometabolic disorders. *Nature.* 2017; 542:177-185
72. Hotamisligil G S, Erbay E. Nutrient sensing and inflammation in metabolic diseases. *Nat Rev Immunol.* 2008; 8:923-934
73. Tsimikas S, Brilakis E S, Miller E R, McConnell J P, Lennon R J, Kornman K S, Witztum J L, Berger P B. Oxidized phospholipids, lp(a) lipoprotein, and coronary artery disease. *N Engl J Med.* 2005; 353:46-57
74. Holvoet P, Vanhaecke J, Janssens S, Van de Werf F, Collen D. Oxidized ldl and malondialdehyde-modified ldl in patients with acute coronary syndromes and stable coronary artery disease. *Circulation.* 1998; 98:1487-1494
75. Upston J M, Niu X, Brown A J, Mashima R, Wang H, Senthilmohan R, Kettle A J, Dean R T, Stocker R. Disease stage-dependent accumulation of lipid and protein oxidation products in human atherosclerosis. *The American journal of pathology.* 2002; 160:701-710
76. Steinberg D, Witztum J L. Is the oxidative modification hypothesis relevant to human atherosclerosis? Do the antioxidant trials conducted to date refute the hypothesis-?*Circulation.* 2002; 105:2107-2111
77. Otsuka F, Yasuda S, Noguchi T, Ishibashi-Ueda H. Pathology of coronary atherosclerosis and thrombosis. *Cardiovasc Diagn Ther.* 2016; 6:396-408
78. Waguri Y, Otsuka T, Sugimura I, Matsui N, Asai K, Moriyama A, Kato T. Gliostatin/platelet-derived endothelial cell growth factor as a clinical marker of rheumatoid arthritis and its regulation in fibroblast-like synoviocytes. *Br J Rheumatol.* 1997; 36:315-321
79. Toyoda Y, Tabata S, Kishi J, et al. Thymidine phosphorylase regulates the expression of cxcl10 in rheumatoid arthritis fibroblast-like synoviocytes. *Arthritis Rheumatol.* 2014; 66:560-568
80. Rahmati M, Petitbarat M, Dubanchet S, Bensussan A, Chaouat G, Ledee N. Granulocyte-colony stimulating factor related pathways tested on an endometrial ex-vivo model. *PloS one.* 2014; 9:e102286
81. Eda H, Fujimoto K, Watanabe S, Ura M, Hino A, Tanaka Y, Wada K, Ishitsuka H. Cytokines induce thymidine phosphorylase expression in tumor cells and make them more susceptible to 5'-deoxy-5-fluorouridine. *Cancer chemotherapy and pharmacology.* 1993; 32:333-338
82. Griffiths L, Dachs G U, Bicknell R, Harris A L, Stratford U. The influence of oxygen tension and ph on the expression of platelet-derived endothelial cell growth factor/thymidine phosphorylase in human breast tumor cells grown in vitro and in vivo. *Cancer research.* 1997; 57:570-572
83. Sawada N, Ishikawa T, Fukase Y, Nishida M, Yoshikubo T, Ishitsuka H. Induction of thymidine phosphorylase activity and enhancement of capecitabine efficacy by taxol/taxotere in human cancer xenografts. *Clinical cancer research: an official journal of the American Association for Cancer Research.* 1998; 4:1013-1019
84. Endo M, Shinbori N, Fukase Y, Sawada N, Ishikawa T, Ishitsuka H, Tanaka Y. Induction of thymidine phosphorylase expression and enhancement of efficacy of capecitabine or 5'-deoxy-5-fluorouridine by cyclophosphamide in mammary tumor models. *International journal of cancer. Journal international du cancer.* 1999; 83:127-134
85. Sawada N, Ishikawa T, Sekiguchi F, Tanaka Y, Ishitsuka H. X-ray irradiation induces thymidine phosphorylase and enhances the efficacy of capecitabine (xeloda) in human cancer xenografts. *Clinical cancer research: an official journal of the American Association for Cancer Research.* 1999; 5:2948-2953
86. Gatsiou A, Boeckel J N, Randriamboavonjy V, Stellos K. Micrornas in platelet biogenesis and function: Implications in vascular homeostasis and inflammation. *Curr Vasc Pharmacol.* 2012; 10:524-531
87. Coppinger J A, Maguire P B. Insights into the platelet releasate. *Curr Pharm Des.* 2007; 13:2640-2646
88. Gawaz M, Langer H, May A E. Platelets in inflammation and atherogenesis. *The Journal of clinical investigation.* 2005; 115:3378-3384
89. Tedgui A, Mallat Z. Cytokines in atherosclerosis: Pathogenic and regulatory pathways. *Physiol Rev.* 2006; 86:515-581
90. Lievens D, von Hundelshausen P. Platelets in atherosclerosis. *Thromb Haemost.* 2011; 106:827-838
91. Triques K, Stevenson M. Characterization of restrictions to human immunodeficiency virus type 1 infection of monocytes. *J Virol.* 2004; 78:5523-5527
92. Boyle J J, Wilson B, Bicknell R, Harrower S, Weissberg P L, Fan T P. Expression of angiogenic factor thymidine phosphorylase and angiogenesis in human atherosclerosis. *The Journal of pathology.* 2000; 192:234-242
93. Bijnsdorp I V, de Bruin M, Laan A C, Fukushima M, Peters G J. The role of platelet-derived endothelial cell growth factor/thymidine phosphorylase in tumor behavior. *Nucleosides, nucleotides & nucleic acids.* 2008; 27:681-691
94. Fox S B, Moghaddam A, Westwood M, Turley H, Bicknell R, Gatter K C, Harris A L. Platelet-derived endothelial cell growth factor/thymidine phosphorylase expression in normal tissues: An immunohistochemical study. *The Journal of pathology.* 1995; 176:183-190
95. Tabas I, Bornfeldt K E. Macrophage phenotype and function in different stages of atherosclerosis. *Circulation research.* 2016; 118:653-667
96. Russo L, Lumeng C N. Properties and functions of adipose tissue macrophages in obesity. *Immunology.* 2018; 155:407-417
97. Lumeng C N, Bodzin J L, Saltiel A R. Obesity induces a phenotypic switch in adipose tissue macrophage polarization. *The Journal of clinical investigation.* 2007; 117: 175-184
98. Shi L, Chowdhury S M, Smallwood H S, Yoon H, Mottaz-Brewer H M, Norbeck A D, McDermott J E, Clauss T R, Heffron F, Smith R D, Adkins J N. Proteomic investigation of the time course responses of raw 264.7 macrophages to infection with *Salmonella enterica. Infect Immun.* 2009; 77:3227-3233
99. Martinez R, de Villavicencio-Diaz T N, Sanchez A, et al. Comparative proteomic analysis of growth hormone secretagogue a233 treatment of murine macrophage cells j774a.2 indicates it has a role in antiviral innate response. *Biochem Biophys Rep.* 2016; 5:379-387
100. Bijnen M, van de Gaar J, Vroomen M, Gijbels M J, de Winther M, Schalkwijk C G, Wouters K. Adipose tissue macrophages do not affect atherosclerosis development in mice. *Atherosclerosis.* 2018; 281:31-37
101. Tabata S, Ikeda R, Yamamoto M, Shimaoka S, Mukaida N, Takeda Y, Yamada K, Soga T, Furukawa T, Akiyama S. Thymidine phosphorylase activates nfkappab and stimulates the expression of angiogenic and metastatic factors in human cancer cells. *Oncotarget.* 2014; 5:10473-10485
102. Gao W, Xiong Y, Li Q, Yang H. Inhibition of toll-like receptor signaling as a promising therapy for inflammatory diseases: A journey from molecular to nano therapeutics. *Front Physiol.* 2017; 8:508

103. Kim S, Joe Y, Surh Y J, Chung H T. Differential regulation of toll-like receptor-mediated cytokine production by unfolded protein response. *Oxid Med Cell Longev.* 2018; 2018:9827312

104. Zimmers T A, Fishel M L, Bonetto A. Stat3 in the systemic inflammation of cancer cachexia. *Semin Cell Dev Biol.* 2016; 54:28-41

105. Yang X, Murthy V, Schultz K, Tatro J B, Fitzgerald K A, Beasley D. Toll-like receptor 3 signaling evokes a proinflammatory and proliferative phenotype in human vascular smooth muscle cells. *Am J Physiol Heart Circ Physiol.* 2006; 291:H2334-2343

106. McCarthy C G, Wenceslau C F, Ogbi S, Szasz T, Webb R C. Toll-like receptor 9-dependent ampkalpha activation occurs via tak1 and contributes to rhoa/rock signaling and actin polymerization in vascular smooth muscle cells. *The Journal of pharmacology and experimental therapeutics.* 2018; 365:60-71

107. Kapelouzou A, Giaglis S, Peroulis M, Katsimpoulas M, Moustardas P, Aravanis C V, Kostakis A, Karayannakos P E, Cokkinos D V. Overexpression of toll-like receptors 2, 3, 4, and 8 is correlated to the vascular atherosclerotic process in the hyperlipidemic rabbit model: The effect of statin treatment. *J Vasc Res.* 2017; 54:156-169

108. Cartwright N, McMaster S K, Sorrentino R, Paul-Clark M, Sriskandan S, Ryffel B, Quesniaux V F, Evans T W, Mitchell J A. Elucidation of toll-like receptor and adapter protein signaling in vascular dysfunction induced by gram-positive *Staphylococcus aureus* or gram-negative *Escherichia coli. Shock.* 2007; 27:40-47

109. Christian F, Smith E L, Carmody R J. The regulation of nf-kappab subunits by phosphorylation. *Cells.* 2016; 5

110. Solinas G, Becattini B. Jnk at the crossroad of obesity, insulin resistance, and cell stress response. *Mol Metab.* 2017; 6:174-184

111. Li H, Yu X. Emerging role of jnk in insulin resistance. *Curr Diabetes Rev.* 2013; 9:422-428

112. Lee Y H, Giraud J, Davis R J, White M F. C-jun n-terminal kinase (jnk) mediates feedback inhibition of the insulin signaling cascade. *The Journal of biological chemistry.* 2003; 278:2896-2902

113. O'Neill L A, Golenbock D, Bowie A G. The history of toll-like receptors—redefining innate immunity. *Nat Rev Immunol.* 2013; 13:453-460

114. Brown V, Brown R A, Ozinsky A, Hesselberth J R, Fields S. Binding specificity of toll-like receptor cytoplasmic domains. *Eur J Immunol.* 2006; 36:742-753

115. Dallari S, Macal M, Loureiro M E, Jo Y, Swanson L, Hesser C, Ghosh P, Zuniga E I. Src family kinases fyn and lyn are constitutively activated and mediate plasmacytoid dendritic cell responses. *Nat Commun.* 2017; 8:14830

116. Wang K Z, Wara-Aswapati N, Boch J A, Yoshida Y, Hu C D, Galson D L, Auron P E. Traf6 activation of pi 3-kinase-dependent cytoskeletal changes is cooperative with ras and is mediated by an interaction with cytoplasmic src. *J Cell Sci.* 2006; 119:1579-1591

117. Chen K, Febbraio M, Li W, Silverstein R L. A specific cd36-dependent signaling pathway is required for platelet activation by oxidized low-density lipoprotein. *Circulation research.* 2008; 102:1512-1519

118. Anto Michel N, Colberg C, Buscher K, et al. Inflammatory pathways regulated by tumor necrosis receptor-associated factor 1 protect from metabolic consequences in diet-induced obesity. *Circulation research.* 2018; 122:693-700

119. Fujieda S, Sunaga H, Tsuzuki H, Fan G K, Saito H. Il-10 expression is associated with the expression of platelet-derived endothelial cell growth factor and prognosis in oral and oropharyngeal carcinoma. *Cancer letters.* 1999; 136:1-9

120. Schmidt C, Peng B, Li Z, Sclabas G M, Fujioka S, Niu J, Schmidt-Supprian M, Evans D B, Abbruzzese J L, Chiao P J. Mechanisms of proinflammatory cytokine-induced biphasic nf-kappab activation. *Mol Cell.* 2003; 12:1287-1300

121. White M F. The irs-signalling system: A network of docking proteins that mediate insulin action. *Mol Cell Biochem.* 1998; 182:3-11

122. Pessin J E, Saltiel A R. Signaling pathways in insulin action: Molecular targets of insulin resistance. *J Clin Invest.* 2000; 106:165-169

123. Copps K D, White M F. Regulation of insulin sensitivity by serine/threonine phosphorylation of insulin receptor substrate proteins irs1 and irs2. *Diabetologia.* 2012; 55:2565-2582

124. Peters G J, Bijnsdorp I V, Fukushima M. Thymidine phoshorylase as a target for antiangiogenesis treatment. *Nucleic acids symposium series.* 2008:629

125. Lee T W, Kwon H, Zong H, Yamada E, Vatish M, Pessin J E, Bastie C C. Fyn deficiency promotes a preferential increase in subcutaneous adipose tissue mass and decreased visceral adipose tissue inflammation. *Diabetes.* 2013; 62:1537-1546

126. Kim Y J, Sano T, Nabetani T, Asano Y, Hirabayashi Y. Gprc5b activates obesity-associated inflammatory signaling in adipocytes. *Sci Signal.* 2012; 5:ra85

127. Guo L, Akahori H, Harari E, et al. Cd163+ macrophages promote angiogenesis and vascular permeability accompanied by inflammation in atherosclerosis. *The Journal of clinical investigation.* 2018; 128:1106-1124

128. Huo Y, Schober A, Forlow S B, Smith D F, Hyman M C, Jung S, Littman D R, Weber C, Ley K. Circulating activated platelets exacerbate atherosclerosis in mice deficient in apolipoprotein e. *Nat Med.* 2003; 9:61-67

129. Carlucci P M, Purmalek M M, Dey A K, et al. Neutrophil subsets and their gene signature associate with vascular inflammation and coronary atherosclerosis in lupus. *JCI Insight.* 2018; 3

130. Gimbrone M A, Jr., Garcia-Cardena G. Endothelial cell dysfunction and the pathobiology of atherosclerosis. *Circulation research.* 2016; 118:620-636

131. Bennett M R, Sinha S, Owens G K. Vascular smooth muscle cells in atherosclerosis. *Circulation research.* 2016; 118:692-702

132. Cleary J M, Rosen L S, Yoshida K, Rasco D, Shapiro G I, Sun W. A phase 1 study of the pharmacokinetics of nucleoside analog trifluridine and thymidine phosphorylase inhibitor tipiracil (components of tas-102) vs trifluridine alone. *Invest New Drugs.* 2017; 35:189-197

133. Ali L, Schnitzler J G, Kroon J. Metabolism: The road to inflammation and atherosclerosis. *Curr Opin Lipidol.* 2018; 29:474-480

134. Tomas L, Edsfeldt A, Mollet I G, Perisic Matic L, Prehn C, Adamski J, Paulsson-Berne G, Hedin U, Nilsson J, Bengtsson E, Goncalves I, Bjorkbacka H. Altered metabolism distinguishes high-risk from stable carotid atherosclerotic plaques. *Eur Heart J.* 2018; 39:2301-2310

135. Langer H F, Chavakis T. Leukocyte-endothelial interactions in inflammation. *Journal of cellular and molecular medicine.* 2009; 13:1211-1220

136. Chen M B, Hajal C, Benjamin D C, Yu C, Azizgolshani H, Hynes R O, Kamm R D. Inflamed neutrophils sequestered at entrapped tumor cells via chemotactic confinement promote tumor cell extravasation. *Proceedings of*

*the National Academy of Sciences of the United States of America.* 2018; 115:7022-7027

137. Lester E A, Babensee J E. Proinflammatory phenotype of endothelial cells after coculture with biomaterial-treated blood cells. *J Biomed Mater Res A.* 2003; 64:397-410

138. Scotland R S, Cohen M, Foster P, Lovell M, Mathur A, Ahluwalia A, Hobbs A J. C-type natriuretic peptide inhibits leukocyte recruitment and platelet-leukocyte interactions via suppression of p-selectin expression. *Proceedings of the National Academy of Sciences of the United States of America.* 2005; 102:14452-14457

139. Sehnert B, Burkhardt H, Wessels J T, Schroder A, May M J, Vestweber D, Zwerina J, Warnatz K, Nimmerjahn F, Schett G, Dubel S, Voll R E. Nf-kappab inhibitor targeted to activated endothelium demonstrates a critical role of endothelial nf-kappab in immune-mediated diseases. *Proceedings of the National Academy of Sciences of the United States of America.* 2013; 110:16556-16561

140. Rahaman S O, Li W, Silverstein R L. Vav guanine nucleotide exchange factors regulate atherosclerotic lesion development in mice. *Arteriosclerosis, thrombosis, and vascular biology.* 2013; 33:2053-2057

141. Robinet P, Milewicz D M, Cassis L A, Leeper N J, Lu H S, Smith J D. Consideration of sex differences in design and reporting of experimental arterial pathology studies-statement from atvb council. *Arteriosclerosis, thrombosis, and vascular biology.* 2018; 38:292-303

142. Titterington J S, Sukhanov S, Higashi Y, Vaughn C, Bowers C, Delafontaine P. Growth hormone-releasing peptide-2 suppresses vascular oxidative stress in apoe−/− mice but does not reduce atherosclerosis. *Endocrinology.* 2009; 150:5478-5487

143. Laursen J B, Somers M, Kurz S, McCann L, Warnholtz A, Freeman B A, Tarpey M, Fukai T, Harrison D G. Endothelial regulation of vasomotion in apoe-deficient mice: Implications for interactions between peroxynitrite and tetrahydrobiopterin. *Circulation.* 2001; 103:1282-1288

144. Sussan T E, Jun J, Thimmulappa R, Bedja D, Antero M, Gabrielson K L, Polotsky V Y, Biswal S. Disruption of nrf2, a key inducer of antioxidant defenses, attenuates apoe-mediated atherosclerosis in mice. *PLoS One.* 2008; 3:e3791

145. Kuchibhotla S, Vanegas D, Kennedy D J, Guy E, Nimako G, Morton R E, Febbraio M. Absence of cd36 protects against atherosclerosis in apoe knock-out mice with no additional protection provided by absence of scavenger receptor a i/ii. *Cardiovasc Res.* 2008; 78:185-196

146. Boschetti E, D'Alessandro R, Bianco F, Carelli V, Cenacchi G, Pinna A D, Del Gaudio M, Rinaldi R, Stanghellini V, Pironi L, Rhoden K, Tugnoli V, Casali C, De Giorgio R. Liver as a source for thymidinephosphorylase replacement in mitochondrial neurogastrointestinal encephalomyopathy. *PloS one.* 2014; 9:e96692

147. Finkenstedt A, Schranz M, Bosch S, Karall D, Burgi S S, Ensinger C, Drach M, Mayr J A, Janecke A R, Vogel W, Nachbaur D, Zoller H. Mngie syndrome: Liver cirrhosis should be ruled out prior to bone marrow transplantation. *JMD Rep.* 2013; 10:41-44

148. Farrell G C, Haczeyni F, Chitturi S. Pathogenesis of nash: How metabolic complications of overnutrition favour lipotoxicity and pro-inflammatory fatty liver disease. *Advances in experimental medicine and biology.* 2018; 1061:19-44

149. Saponaro C, Gaggini M, Carli F, Gastaldelli A. The subtle balance between lipolysis and lipogenesis: A critical point in metabolic homeostasis. *Nutrients.* 2015; 7:9453-9474

150. Hotchkiss K A, Ashton A W, Schwartz E L. Thymidine phosphorylase and 2-deoxyribose stimulate human endothelial cell migration by specific activation of the integrins alpha 5 beta 1 and alpha v beta 3. *The Journal of biological chemistry.* 2003; 278:19272-19279

151. Zhou J, Xiao Y S, Tang Z Y, Fan J, Wu Z Q, Zhao Y, Xue Q, Shen Z Z, Liu Y K, Ye S L. Transfection of thymidine phosphorylase cdna to human hepatocellular carcinoma cells enhances sensitivity to fluoropyrimidine but augments endothelial cell migration. *Journal of cancer research and clinical oncology.* 2005; 131:547-551

152. Bijnsdorp I V, Vrijland K, Vroling L, Fukushima M, Peters G J. Increased migration by stimulation of thymidine phosphorylase in endothelial cells of different origin. *Nucleosides, nucleotides & nucleic acids.* 2010; 29:482-487

153. Chen K, Li W, Major J, Rahaman S O, Febbraio M, Silverstein R L. Vav guanine nucleotide exchange factors link hyperlipidemia and a prothrombotic state. *Blood.* 2011

154. Ghosh A, Li W, Febbraio M, Espinola R G, McCrae K R, Cockrell E, Silverstein R L. Platelet cd36 mediates interactions with endothelial cell-derived microparticles and contributes to thrombosis in mice. *J Clin Invest.* 2008; 118:1934-1943

155. Klenotic P A, Page R C, Li W, Amick J, Misra S, Silverstein R L. Molecular basis of antiangiogenic thrombospondin-1 type 1 repeat domain interactions with cd36. *Arteriosclerosis, thrombosis, and vascular biology.* 2013; 33:1655-1662

156. Yue H, Li W, Desnoyer R, Karnik S S. Role of nuclear unphosphorylated stat3 in angiotensin ii type 1 receptor-induced cardiac hypertrophy. *Cardiovasc Res.* 2010; 85:90-99.

157. Li W, Chiba Y, Kimura T, Morioka K, Uesaka T, Ihaya A, Muraoka R. Transmyocardial laser revascularization induced angiogenesis correlated with the expression of matrix metalloproteinases and platelet-derived endothelial cell growth factor. *Eur J Cardiothorac Surg.* 2001; 19:156-163.

158. Day ISCfWT. Thrombosis: a major contributor to the global disease burden. J Thromb Haemost. 2014; 12(10): 1580-1590.

159. Murray C J, Vos T, Lozano R, et al. Disability-adjusted life years (DALYs) for 291 diseases and injuries in 21 regions, 1990-2010: a systematic analysis for the Global Burden of Disease Study 2010. Lancet. 2012; 380(9859): 2197-2223.

160. Jackson S P. Arterial thrombosis-insidious, unpredictable and deadly. Nat Med. 2011; 17(11):1423-1436.

161. Ezumi Y, Shindoh K, Tsuji M, Takayama H. Physical and functional association of the Src family kinases Fyn and Lyn with the collagen receptor glycoprotein V I-Fc receptor gamma chain complex on human platelets. J Exp Med. 1998; 188(2):267-276.

162. Furie B C, Furie B. Tissue factor pathway vs. collagen pathway for in vivo platelet activation. Blood Cells Mol Dis. 2006; 36(2):135-138.

163. Stegner D, Nieswandt B. Platelet receptor signaling in thrombus formation. J Mol Med (Berl). 2011; 89(2):109-121.

164. Smyth S S, Woulfe D S, Weitz J I, et al. G-protein-coupled receptors as signaling targets for antiplatelet therapy. Arteriosclerosis, thrombosis, and vascular biology. 2009; 29(4):449-457.
165. Depta J P, Bhatt D L. New approaches to inhibiting platelets and coagulation. Annual review of pharmacology and toxicology. 2015; 55:373-397.
166. Franchi F, Angiolillo D J. Novel antiplatelet agents in acute coronary syndrome. Nature reviews Cardiology. 2015; 12(1):30-47.
167. Desai N R, Bhatt D L. The state of periprocedural antiplatelet therapy after recent trials. JACC Cardiovascular interventions. 2010; 3(6):571-583.
168. de Souza Brito F, Tricoci P. Novel anti-platelet agents: focus on thrombin receptor antagonists. Journal of cardiovascular translational research. 2013; 6(3):415-424.
169. Chassot P G, Delabays A, Spahn D R. Perioperative antiplatelet therapy: the case for continuing therapy in patients at risk of myocardial infarction. Br J Anaesth. 2007; 99(3):316-328.
170. Capodanno D, Ferreiro J L, Angiolillo D J. Antiplatelet therapy: new pharmacological agents and changing paradigms. J Thromb Haemost. 2013; 11 Suppl 1:316-329.
171. Kubilus J, Lee L D, Baden H P. Purification of thymidine phosphorylase from human amniochorion. Biochimica et biophysica acta. 1978; 527(1):221-228.
172. Desgranges C, Razaka G, Rabaud M, Bricaud H. Catabolism of thymidine in human blood platelets: purification and properties of thymidine phosphorylase. Biochimica et biophysica acta. 1981; 654(2):211-218.
173. Miyazono K, Okabe T, Urabe A, Takaku F, Heldin C H. Purification and properties of an endothelial cell growth factor from human platelets. The Journal of biological chemistry. 1987; 262(9):4098-4103.
174. Desgranges C, Razaka G, Rabaud M, Bricaud H. Catabolism of thymidine in human blood platelets: purification and properties of thymidine phosphorylase. Biochimica et biophysica acta. 1981; 654(2):211-218.
175. Bronckaers A, Aguado L, Negri A, et al. Identification of aspartic acid-203 in human thymidine phosphorylase as an important residue for both catalysis and non-competitive inhibition by the small molecule “crystallization chaperone” 5'-O-tritylinosine (KIN59). Biochemical pharmacology. 2009; 78(3):231-240.
176. Liekens S, Bronckaers A, Perez-Perez M J, Balzarini J. Targeting platelet-derived endothelial cell growth factor/thymidine phosphorylase for cancer therapy. Biochemical pharmacology. 2007; 74(11):1555-1567.
177. Li W, Yue H. Thymidine phosphorylase: A potential new target for treating cardiovascular disease. Trends Cardiovasc Med. 2018; 28(3):157-171.
178. Norman R A, Barry S T, Bate M, et al. Crystal structure of human thymidine phosphorylase in complex with a small molecule inhibitor. Structure. 2004; 12(1):75-84.
179. Schwartz M. Thymidine phosphorylase from *Escherichia coli*. Properties and kinetics. European journal of biochemistry/FEBS. 1971; 21(2):191-198.
180. Li W, Gigante A, Perez-Perez M J, et al. Thymidine phosphorylase participates in platelet signaling and promotes thrombosis. Circulation research. 2014; 115(12):997-1006.
181. Liekens S, Balzarini J, Hernandez A, et al. Thymidine phosphorylase is noncompetitively inhibited by 5'-O-trityl-inosine (KIN59) and related compounds. Nucleosides, nucleotides & nucleic acids. 2006; 25(9-11):975-980.
182. Lopez L C, Akman H O, Garcia-Cazorla A, et al. Unbalanced deoxynucleotide pools cause mitochondrial DNA instability in thymidine phosphorylase-deficient mice. Hum Mol Genet. 2009; 18(4):714-722.
183. Li W, McIntyre T, Silverstein R. Ferric chloride-induced murine carotid arterial injury: a model of redox pathology. Redox Biology. 2013; 1(1):50-55.
184. Li W, Nieman, M., Sen Gupta, A. Ferric Chloride-induced Murine Thrombosis Models. J Vis Exp. 2016; 115:e54479.
185. Pawlowski C L, Li W, Sun M, et al. Platelet microparticle-inspired clot-responsive nanomedicine for targeted fibrinolysis. Biomaterials. 2017; 128:94-108.
186. Chen K, Li W, Major J, Rahaman S O, Febbraio M, Silverstein R L. Vav guanine nucleotide exchange factors link hyperlipidemia and a prothrombotic state. Blood. 2011.
187. Yue H, Tanaka K, Furukawa T, Karnik S S, Li W. Thymidine phosphorylase inhibits vascular smooth muscle cell proliferation via upregulation of STAT3. Biochimica et biophysica acta. 2012; 1823(8):1316-1323.
188. Ruggeri Z M, Mendolicchio G L. Adhesion mechanisms in platelet function. Circulation research. 2007; 100(12):1673-1685.
189. Gupta N, Li W, Willard B, Silverstein R L, McIntyre T M. Proteasome proteolysis supports stimulated platelet function and thrombosis. Arteriosclerosis, thrombosis, and vascular biology. 2014; 34(1):160-168.
190. Srikanthan S, Li W, Silverstein R L, McIntyre T M. Exosome poly-ubiquitin inhibits platelet activation, downregulates CD36 and inhibits pro-atherothombotic cellular functions. J Thromb Haemost. 2014; 12(11):1906-1917.
191. Woulfe D S. Akt signaling in platelets and thrombosis. ExpertRev Hematol. 2010; 3(1):81-91.
192. Chen K, Febbraio M, Li W, Silverstein R L. A specific CD36-dependent signaling pathway is required for platelet activation by oxidized low-density lipoprotein. Circulation research. 2008; 102(12):1512-1519.
193. Surin W R, Prakash P, Barthwal M K, Dikshit M. Optimization of ferric chloride induced thrombosis model in rats: effect of anti-platelet and anti-coagulant drugs. Journal of pharmacological and toxicological methods. 2010; 61(3):287-291.
194. Adams H P, Jr., Adams R J, Brott T, et al. Guidelines for the early management of patients with ischemic stroke: A scientific statement from the Stroke Council of the American Stroke Association. Stroke; a journal of cerebral circulation. 2003; 34(4):1056-1083.
195. Li W, Nieman M, Sen Gupta A. Ferric Chloride-induced Murine Thrombosis Models. Journal of visualized experiments: JoVE. 2016(115).
196. Li W, Chiba Y, Kimura T, et al. Transmyocardial laser revascularization induced angiogenesis correlated with the expression of matrix metalloproteinases and platelet-derived endothelial cell growth factor. Eur J Cardiothorac Surg. 2001; 19(2):156-163.
197. Li W, Tanaka K, Morioka K, et al. Long-term effect of gene therapy for chronic ischemic myocardium using platelet-derived endothelial cell growth factor in dogs. J Gene Med. 2008; 10(4):412-420.
198. Yamada N, Li W, Ihaya A, et al. Platelet-derived endothelial cell growth factor gene therapy for limb ischemia. J Vasc Surg. 2006; 44(6):1322-1328.
199. Koukourakis M I, Giatromanolaki A, O’Byrne K J, et al. Platelet-derived endothelial cell growth factor expression correlates with tumour angiogenesis and prognosis in non-small-cell lung cancer. British journal of cancer. 1997; 75(4):477-481.
200. Akiyama S, Furukawa T, Sumizawa T, et al. The role of thymidine phosphorylase, an angiogenic enzyme, in tumor progression. Cancer Sci. 2004; 95(11):851-857.
201. Nakajima Y, Madhyastha R, Maruyama M. 2-Deoxy-D-ribose, a downstream mediator of thymidine phosphorylase, regulates tumor angiogenesis and progression. Anticancer Agents Med Chem. 2009; 9(2):239-245.
202. Burkhart J M, Vaudel M, Gambaryan S, et al. The first comprehensive and quantitative analysis of human platelet protein composition allows the comparative analysis of structural and functional pathways. Blood. 2012; 120(15): e73-82.
203. Wijten P, van Holten T, Woo L L, et al. High precision platelet releasate definition by quantitative reversed protein profiling-brief report. Arteriosclerosis, thrombosis, and vascular biology. 2013; 33(7):1635-1638.
204. Ignatescu M C, Gharehbaghi-Schnell E, Hassan A, et al. Expression of the angiogenic protein, platelet-derived endothelial cell growth factor, in coronary atherosclerotic plaques: In vivo correlation of lesional microvessel density and constrictive vascular remodeling. Arteriosclerosis, thrombosis, and vascular biology. 1999; 19(10):2340-2347.
205. Boyle J J, Wilson B, Bicknell R, Harrower S, Weissberg P L, Fan T P. Expression of angiogenic factor thymidine phosphorylase and angiogenesis in human atherosclerosis. J Pathol. 2000; 192(2):234-242.
206. Connolly G C, Khorana A A. Emerging risk stratification approaches to cancer-associated thrombosis: risk factors, biomarkers and a risk score. Thromb Res. 2010; 125 Suppl 2:S1-7.
207. Demers M, Krause D S, Schatzberg D, et al. Cancers predispose neutrophils to release extracellular DNA traps that contribute to cancer-associated thrombosis. Proceedings of the National Academy of Sciences of the United States of America. 2012; 109(32):13076-13081.
208. Hamed E A, Zakary M M, Abdelal R M, Abdel Moneim E M. Vasculopathy in type 2 diabetes mellitus: role of specific angiogenic modulators. J Physiol Biochem. 2011; 67(3):339-349.
209. Goldin-Lang P, Pels K, Tran Q V, et al. Effect of ionizing radiation on cellular procoagulability and coordinated gene alterations. Haematologica. 2007; 92(8): 1091-1098.
210. Nieswandt B, Watson S P. Platelet-collagen interaction: is GPVI the central receptor? Blood. 2003; 102(2):449-461.
211. Kato K, Kanaji T, Russell S, et al. The contribution of glycoprotein VI to stable platelet adhesion and thrombus formation illustrated by targeted gene deletion. Blood. 2003; 102(5):1701-1707.
212. Ungerer M, Rosport K, Bultmann A, et al. Novel antiplatelet drug revacept (Dimeric Glycoprotein V I-Fc) specifically and efficiently inhibited collagen-induced platelet aggregation without affecting general hemostasis in humans. Circulation. 2011; 123(17):1891-1899.
213. Schupke S, Hein-Rothweiler R, Mayer K, et al. Revacept, a Novel Inhibitor of Platelet Adhesion, in Patients Undergoing Elective PCI-Design and Rationale of the Randomized ISAR-PLASTER Trial. Thromb Haemost. 2019; 119(9):1539-1545.
214. Kim S, Jin J, Kunapuli S P. Akt activation in platelets depends on Gi signaling pathways. J Biol Chem. 2004; 279(6):4186-4195.
215. Mayer R J, Van Cutsem E, Falcone A, et al. Randomized trial of TAS-102 for refractory metastatic colorectal cancer. N Engl J Med. 2015; 372(20):1909-1919.
216. Yoshino T, Mizunuma N, Yamazaki K, et al. TAS-102 monotherapy for pretreated metastatic colorectal cancer: a double-blind, randomised, placebo-controlled phase 2 trial. The lancet oncology. 2012; 13(10):993-1001.
217. Doi T, Ohtsu A, Yoshino T, et al. Phase I study of TAS-102 treatment in Japanese patients with advanced solid tumours. British journal of cancer. 2012; 107(3): 429-434.
218. Hong D S, Abbruzzese J L, Bogaard K, et al. Phase I study to determine the safety and pharmacokinetics of oral administration of TAS-102 in patients with solid tumors. Cancer. 2006; 107(6):1383-1390.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating obesity, comprising administering to a subject in need thereof an effective amount of a thymidine phosphorylase inhibitor sufficient to directly inhibit and reduce an activity of thymidine phosphorylase in the subject, wherein the thymidine phosphorylase inhibitor is tipiracil.

2. The method of claim 1, wherein administering the thymidine phosphorylase inhibitor reduces an expression level of lipogenesis markers.

3. The method of claim 2, wherein the lipogenesis markers are selected from the group consisting of acetyl co-A carboxylase, peroxisome proliferator-activated receptor gamma, and a combination thereof.

4. The method of claim 1, wherein administering the thymidine phosphorylase inhibitor reduces an expression level or activity of a mitogen activated protein kinase (MAPK).

5. The method of claim 4, wherein the mitogen activated protein kinase is selected from the group consisting of p38, ERK1/2, and JNK2.

6. The method of claim 1, wherein administering the thymidine phosphorylase inhibitor increases an expression level of a lipolysis protein, an adipose triglyceride lipase, or combinations thereof.

7. The method of claim 1, wherein administering the thymidine phosphorylase inhibitor reduces an activity level of NF-κB.

8. The method of claim 1, wherein administering the thymidine phosphorylase inhibitor reduces an expression level of an inflammatory cytokine.

9. The method of claim 8, wherein the inflammatory cytokine is selected from the group consisting of TNFα, IL-1, IL-6, IL-8, IL-17, interferon-γ, granulocyte-colony stimulating factor, Toll-like receptor, and combinations thereof.

10. The method of claim 1, wherein administering the thymidine phosphorylase inhibitor reduces an expression level or activity of a glycolysis-associated protein.

11. The method of claim 10, wherein the glycolysis-associated protein is selected from fructosebisphosphate aldolase (FBPA), glyceraldehyde-3-phosphate dehydrogenase (GAPDH), and pyruvate kinase muscle isoform M2 (PKM2).

12. The method of claim 1, wherein administering the thymidine phosphorylase inhibitor increases an amount of glucose tolerance in the subject.

13. The method of claim 1, wherein administering the thymidine phosphorylase inhibitor decreases body weight of the subject, reduces lipid accumulation in a liver of the subject, and/or reduces an amount of atherosclerotic plaques in one or more blood vessels of the subject.

14. The method of claim 1, wherein the subject is a male subject.

* * * * *